United States Patent
Ellington et al.

(10) Patent No.: US 11,419,909 B2
(45) Date of Patent: *Aug. 23, 2022

(54) COMPOSITIONS AND METHODS FOR MAINTAINING OR ENHANCING HOMEOSTASIS OR FUNCTION OF FEMALE LOWER REPRODUCTIVE TRACT

(71) Applicant: FAIRHAVEN HEALTH, LLC, Bellingham, WA (US)

(72) Inventors: Joanna E. Ellington, Valleyford, WA (US); G. Dennis Clifton, Valleyford, WA (US)

(73) Assignee: FAIRHAVEN HEALTH, LLC, Bellingham, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/436,504

(22) Filed: Jun. 10, 2019

(65) Prior Publication Data

US 2020/0129578 A1    Apr. 30, 2020

Related U.S. Application Data

(63) Continuation of application No. 15/894,739, filed on Feb. 12, 2018, now Pat. No. 10,357,527, which is a continuation of application No. 15/351,097, filed on Nov. 14, 2016, now Pat. No. 9,919,018, which is a continuation of application No. 15/207,307, filed on Jul. 11, 2016, now Pat. No. 9,913,871.

(60) Provisional application No. 62/323,516, filed on Apr. 15, 2016.

(51) Int. Cl.

| | |
|---|---|
| *A61K 36/537* | (2006.01) |
| *A61K 9/00* | (2006.01) |
| *A61K 31/7004* | (2006.01) |
| *A61K 9/06* | (2006.01) |
| *A61K 47/02* | (2006.01) |
| *A61K 47/22* | (2006.01) |
| *A61K 47/32* | (2006.01) |
| *A61K 47/38* | (2006.01) |
| *A61K 47/12* | (2006.01) |
| *A61K 47/10* | (2017.01) |
| *A61Q 19/10* | (2006.01) |
| *A61K 8/60* | (2006.01) |
| *A61K 8/97* | (2017.01) |
| *A61K 8/04* | (2006.01) |
| *A61K 47/06* | (2006.01) |
| *A61K 47/26* | (2006.01) |

(52) U.S. Cl.
CPC .......... *A61K 36/537* (2013.01); *A61K 8/042* (2013.01); *A61K 8/60* (2013.01); *A61K 8/97* (2013.01); *A61K 9/0014* (2013.01); *A61K 9/0034* (2013.01); *A61K 9/06* (2013.01); *A61K 31/7004* (2013.01); *A61K 47/02* (2013.01); *A61K 47/06* (2013.01); *A61K 47/10* (2013.01); *A61K 47/12* (2013.01); *A61K 47/22* (2013.01); *A61K 47/26* (2013.01); *A61K 47/32* (2013.01); *A61K 47/38* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 6,159,491 A | 12/2000 | Durrani | |
| 6,440,949 B1 | 8/2002 | Zeng | |
| 6,495,147 B1 | 12/2002 | Dumas et al. | |
| 6,593,309 B2 | 7/2003 | Ellington et al. | |
| 6,632,796 B1 | 10/2003 | Zeng | |
| 6,953,775 B2 | 10/2005 | Burruano et al. | |
| 7,786,176 B2* | 8/2010 | Martin | A61K 47/36 514/738 |
| 7,964,582 B2 | 6/2011 | Stone et al. | |
| 8,586,549 B2 | 11/2013 | Zhou et al. | |
| 8,609,156 B2 | 12/2013 | Roberts | |
| 8,642,080 B2 | 2/2014 | Bender et al. | |
| 8,686,040 B2 | 4/2014 | Ehrenpreis | |
| 8,703,171 B2 | 4/2014 | Schaub et al. | |
| 8,709,385 B2 | 4/2014 | Tamarkin et al. | |
| 8,784,906 B2 | 7/2014 | Gaynor-Krupnick | |
| 8,883,224 B2 | 11/2014 | Florence et al. | |

(Continued)

FOREIGN PATENT DOCUMENTS

| | | |
|---|---|---|
| CA | 2 766 482 | 1/2011 |
| CA | 2 824 471 | 5/2012 |

(Continued)

OTHER PUBLICATIONS

Jenks Aaron A; et al, "Medicinal plant complexes of *Salvia* subgenus *Calosphace*: An ethnobotanical study of new world sages", Journal of Ethnopharmacology, Elsevier Ireland Ltd, IE,vol. 146, No. 1, Jan. 3, 2013 (Jan. 3, 2013), p. 214-224.

(Continued)

*Primary Examiner* — Russell G Fiebig
(74) *Attorney, Agent, or Firm* — ParkerHighlander, PLLC

(57) ABSTRACT

The present disclosure provides compositions and methods for making and using topical compositions comprised of an isotonic, biome-friendly solution containing xylose and/or a *Salvia* extract. The compositions are useful for, for example, maintaining or enhancing female lower reproductive tract (LRT) homeostasis and physiological function. In particular, topical compositions of this disclosure can be formulated for use as a freshening, menopausal, fertility, and/or perineal composition.

34 Claims, 9 Drawing Sheets

(56) References Cited

U.S. PATENT DOCUMENTS

| | | | |
|---|---|---|---|
| 8,906,958 | B2 | 12/2014 | Reichelt et al. |
| 8,911,801 | B2 | 12/2014 | Debaun et al. |
| 8,940,319 | B2 | 1/2015 | O'Donnell et al. |
| 8,993,012 | B2 | 3/2015 | Minatelli et al. |
| 9,005,597 | B2 | 4/2015 | Hansen et al. |
| 9,044,387 | B2 | 6/2015 | Zhao et al. |
| 9,125,806 | B2 | 9/2015 | Mailland et al. |
| 9,131,726 | B2 | 9/2015 | Minatelli et al. |
| 9,470,676 | B2 | 10/2016 | Strgar |
| 9,913,871 | B2 | 3/2018 | Ellington et al. |
| 9,919,018 | B2 | 3/2018 | Ellington et al. |
| 10,357,527 | B2 | 7/2019 | Ellington et al. |
| 2002/0177624 | A1 | 11/2002 | Hanna |
| 2014/0142181 | A1 | 5/2014 | Mills |
| 2015/0025196 | A1 | 1/2015 | Hoogenboom et al. |
| 2017/0360728 | A1 | 12/2017 | Strgar |

FOREIGN PATENT DOCUMENTS

| | | |
|---|---|---|
| CH | 368 267 | 3/1963 |
| CN | 1097311 | 1/1995 |
| CN | 1271290 | 10/2000 |
| CN | 1271291 | 10/2000 |
| CN | 1425403 | 6/2003 |
| CN | 102872256 | 1/2013 |
| CN | 104225219 | 12/2014 |
| CN | 104323950 | 2/2015 |
| CN | 104434638 | 3/2015 |
| EP | 0 509 120 | 4/1991 |
| EP | 3442501 | 2/2019 |
| GB | 2501252 | 10/2013 |
| JP | 2005263655 | 9/2005 |
| WO | WO 0162214 | 8/2001 |
| WO | WO2014188370 A1 | 11/2014 |
| WO | WO2014202550 A2 | 12/2014 |
| WO | WO 2017180174 | 7/2016 |

OTHER PUBLICATIONS

Database WPI Section Ch, Week 201538 Thomson Scientific, London, GB; Class A11, AN 2015-289713 XP002764948, Liu Q: "Natural aftershave comprises chestnut tree extract, natural extract, aloe gel juice, deionized water, seaweed extract, citric acid, salt, hydroxyethyl cellulose, cinnamyl alcohol and natural essence", 3 pages.

Database WPI Section Ch, Week 201531 Thomson Scientific, London GB; Class D21, an 2015-19973T XP002764949, Liu Q: "Natural skin moisturizing cream comprises chestnut tree extract, natural extract, Aloe gel juice, deionized water, glycerol, cinnamyl alcohol and natural essence", 3 pages.

Database WPI Section Ch, Week 201518 Thomson Scientific, London, GB; Class B04, AN 2015-113712 XP002764950, Guy; Jin L; Kuang C: "Traditional Chinese medicinal composition useful for e.g. reducing blood fat, contains cinnamon, Salvia, rhizome ligustici wallichii, Angelica, processed fleece-flower root, radix polygonati officinalis and lotus leaf", 2 pages.

Vaginal gel useful for increasing immunity of vagina, diminishing inflammation and treating various gynecological diseases, contains phellodendron, radix sophorae flavescentis, fructus forsythiae, common cnidium fruit and myrrh, Database WPI Thomson Scientific, London, GB; vol. 2013, No. 35, AN 2013-G035050 Section Ch B04 XP002764951.

Database WPI Section Ch, Week 200363 Thomson Scientific, London, GB; Class B04, AN 2003-664177 XP002764952, Chen L: "Ointment for curing leukoplakia vulvae and its preparing method", 1 page.

Database WPI Section Ch, Week 199719 Thomson Scientific, London GB; Class B04, AN 1997-204072 XP002764953, Yang J: "Preparation of fuchunkang ointment for sexual health", 1 page.

Database WPI Section Ch, Week 200569 Thomson Scientific, London, GB; Class B04, AN 2005-670089 XP002764954, Fujimoto M; Konnom; Tsunoda K; Yoshidam: "Antioxidant useful in skin external preparation such as milky lotion, cream, skin lotion, pack, cosmetic liquid and washing material, contains extract of Salvia plebeian of family labiatae as active ingredient", 2 pages.

Forbes et al., "Modified Silicone Elastomer Vaginal Gels for Sustained Release of Antiretroviral HIV Microbicides," Journal of Pharmaceutical Sciences 103(5):1422-1432, 2014.

Bachhav et al., "Microemulsion-Based Vaginal Gel of Clotrimazole: Formulation, In Vitro Evaluation, and Stability Studies," AAPS PharmSciTech 10(2):476-481, 2009.

Website document entitled: "FENIOL: Preservative-free, Fragrance-Free" (available at www.sinerga.it/news/FENIOL%20minibrochure.pdf). Downloaded from website Feb. 1, 2017.

Garg et al. (2001) Compendium of Pharmaceutical Excipients for Vaginal Formulations. Pharmaceutical Technology Drug Delivery pp. 14-24.

Gulcin et al., "Evaluation of the Antioxidant and Antimicrobial Activities of Clary Sage (*Salvia sclarea* L.)," *Turkish Journal of Awiculture and Forestry* 28(1):25-33, 2004.

Website document entitled "'Nature-identical' Preservative for More Sustainable Science" (available at http://www.cosmeticsandtoiletries.com/formulating/function/preservatives/231622371.html). Downloaded from website Feb. 1, 2017.

Silva et al., "Aggregation and gelation in hydroxypropylmethyl cellulose aqueous solutions," Journal of Colloid and Interface Science 327(2):333-340, 2008.

Adriaens et al., "Mucosal Irritation Potential of Personal Lubricants Relates to Product Osmolality as Detected by the Slug Mucosal Irritation Assay," *Sexually Transmitted Diseases* 35(5):512-516, 2008.

Akgul et al., "Dynamic Changes in Cervical Glycosaminoglycan Composition during Normal Pregnancy and Preterm Birth," *Endocrinology* 153(7):3493-3503, 2012.

Akgul et al., "Hyaluronan in cervical epithelia protects against infection-mediated preterm birth," *J Clin. Invest.* 124(12):5481-5489, 2014.

Akram et al., "Heme oxygenase I-mediated novel anti-inflammatory activities of *Salvia plebeian* and its active components," *Journal of Ethnopharmacology* 174:322-330, 2015.

Albertsmeyer et al., "Effect of pro-inflammatory mediators on membrane-associated mucins expressed by human ocular surface epithelial cells," *Exp. Eve. Res.* 90(3):444-451, 2011.

Ali et al., "Skin pH: From Basic Science to Basic Skin Care," *Acta Derm Venereol* 93:261-267, 2013.

Alonso-Calderon et al., "Characterization of Black Chia Seed (*Salvia hispanica* L) and Oil and Quantification of -sitosterol," *International Research Journal of Biological Sciences* 2(1):70-I2, 2013.

Andersch-Bjorkman et al., "Large Scale Identification of Proteins, Mucins, and Their 0-Glycosylation in the Endocervical Mucus during the Menstrual Cycle," *Molecular & Cellular Proteomics* 6(4):708-716, 2007.

Ayehunie et al., "Development of an in vitro alternative assay method for vaginal irritation,"*Toxicology* 279(1-3):130-138, 2011.

Baranda et al., "Correlation between pH and irritant effect of cleansers marketed for dry skin," *International Journal of Dermatology* 41: 494-499, 2002.

Bianchi et al., "Human Cervical Mucus Can Act in Vitro as a Selective Barrier Against Spermatozoa Carrying Fragmented DNA and Chromatin Structural Abnormalities," *Journal of Assisted Reproduction and Genetics* 21(4):97-102, 2004.

Brockhausen et al., "Chapter 9: O-GalNAc Glycans," Varki et al. (eds.), *Essentials of Glycohiology, $2^{nd}$ edition*, Cold Spring Harbor, NY, Cold Spring Harbor Laboratory Press, 2009. (17 pages).

Bunge et al., "The Safety, Persistence, and Acceptability of an Antiretroviral Microbicide Candidate UC781," *J Acquir Immune Defic Syndr* 60(4):337-343, 2012.

Burns et al., "The use of aromatherapy in intrapartum midwifery practice an observational study," *Complementary Therapies in Nursing & Midwifery* 6(1):33-34, 2000.

Campbell, "Increasing Fertility Through the Use of Essential Oils," Retrieved from: http://natural-fertility-info.com/fertility-essential-oils.html, 2016. (3 pages).

(56) References Cited

OTHER PUBLICATIONS

Chakraborty et al., "Role of Mucins in the Skin during Benign and Malignant Conditions," Cancer Lett. 301(2):127-141, 2011.

Chen et al., "Transient Antibody-Mucin Interactions Produce a Dynamic Molecular Shield against Viral Invasion," Biophysical Journal 106:2028-2036, 2014.

Choi et al., "Salvia lebeian Suppresses Atopic Dermatitis-Like Skin Lesions," The American Journal of Chinese Medicine 42(4):967-985, 2014.

Chovanova et al., "The inhibition the Tet(K) efflux pump pf tetracycline resistant Staphylococcus epidermidis by essential oils from three Salvia species," Letters in Applied Microbiology 61(1):58-62, 2015.

Critchfield et al., "Cervical Mucus Properties Stratify Risk for Preterm Birth," PLOS ONE 8(8): 1-7, e69528, 2013.

Cui et al., "Antimicrobial activity and mechanisms of Salvia sclarea essential oil," Botanical Studies 56(16):1-8, 2015.

Cunha et al., "Characterization of Commercially Available Vaginal Lubricants: A Safety Perspective," Pharmaceutics 6:530-542, 2014.

De la Rosa, "Poly(2-oxazoline)Sas materials for biomedical applications," J Mater Sci Mater Med. 25(5):1211-1225, 2014.

Department of Health and Human Services, "HyaloGYN@ Hydrating Gel" 510(k) Summary K150883, retrieved from: http://wwvu,.ccessdata.fila.gov/cdrb_docs/pdfl 5/K150883.pdf, 2015 {6 pages).

Dezzutti et al., "Is Wetter Better? AN Evaluation of Over-the-Counter Personal Lubricants for Safety and Anti-HIV-I Activity," PLOS ONE 7(11):1-14, e48328, 2012.

Dusio et al., "Stimulation of TLRs by LMW-HA induces self-defense mechanisms in vaginal epithelium," Immunology and Cell Biology 89:630-639, 2011.

Eckstein et al., "Comparison of Vaginal Tolerance Tests of Speimicidal Preparations in Rabbits and Monkeys," J Reprod. Fert. 20:85-93, 1969.

Eriksen et al., "Cervical mucins affect the motility of human spermatozoa in vitro," Fertility and Sterility 70(2):350-354, 1998.

Espinoza et al., "Acidic pH and increasing $[Ca+^2]$ reduce the swelling of mucins in primary cultures of human cervical cells," Human Reproduction 17(8):1964-1972, 2002.

Farmer et al., "Repeated Vulvovaginal Fungal Infections Cause Persistent Pain in a Mouse Model of Vulvodynia," Sci Transi Med. 3(101):1-16, 2011. (16 pages).

Feki et al., "Human sperm lipid content is modified after migration into human cervical mucus," Molecular Human Reproduction 10(2):137-142, 2004.

Firuzi et al., "Cytotoxic, Antioxidant and Antimicrobial Activities and Phenolic Contents of Eleven Salvia Species from Iran," Iranian Journal of Pharmaceutical Research 12(4):801-810, 2013.

Gali et al., "In Vitro Evaluation of Viability, Integrity, and Inflammation in Genital Epithelia upon Exposure to Pharmaceutical Excipients and Candidate Microbicides," Antimicrobial Agents and Chemotherapy 54(12):5105-5114, 2010.

Garcia et al., "Development of a Buffer System for Dialysis of Bovine Spermatozoa Before Freezing. II. Effect of Sugars and Sugar Alcohols on Postthaw Motility," Theriogenology 31(5):1029-1037, 2013.

Gosalia et al., "Coordinate Regulation of the Gel-forming Mucin Genes at Chromosome 1 1p15.5," The Journal of Biological Chemistry 288(9):6717-6725, 2013.

Gotting et al., "Xylosyltransferase activity in seminal plasma of infertile men," Clinica Chimica Acta 317: 199-202, 2002.

Govindarajan et al., "Membrane-tethered mucins have multiple functions on the ocular surface," Exp Eve Res. 90(6):655-663, 2010. (17 pages).

Hagvall, "Formation of Skin Sensitizers from Fragrance Terpenes via Oxidative Activation Routes," Thesis, University of Gothenburg, retrieved from http://gupea.ub.gu.se/bitstream/2077/18951/1/gupea 2077 18951 1.pdf, 74 pages, 2015.

Han et al., "Effect of Aromatherapy on Symptoms of Dysmenorrhea in College Students: A Randomized Placebo-Controlled Clinical Trial," The Journal of Alternative and Complementary Medicine 12(6):535-541, 2006.

He et al., "Homoplantaginin Inhibits Palmitic Acid-induced Endothelial Cells Inflammation by Suppressing TLR4 and NLRP3 Inflammasome," J Cardiovasc Pharmacol 67:93-101, 2016.

Herbenick et al., "Association of Lubricant Use with Women's Sexual Pleasure, Sexual Satisfaction, and Genital Symptoms: A Prospective Daily Diary Study," J Sex Med. 8(1):202-212, 2011.

International Federation of Professional Aromatherapists, "Pregnancy Guidelines" Retrieved from: http://www.naha.org/assets/uploads/PregnancvGuidelines-Oct1 1.pdf, 7 pages, 2013.

Iyibozkurt et al., "Effect of vascular endothelial growth factor on sperm motility and survival," Reproductive Bio Medicine Online 19(6):784-788, 2009.

Jin et al., "Two new flavones from Salvia plebeia," Natural Product Research 29(14):1315-1322, 2015.

Kesimer et al., "Analyzing the functions oflarge glycoconjugates through the dissipative properties of their absorbed layers using the gel-forming mucin MUC5B as an example," Glycobiology 18(6):463-472, 2008.

Lapwood et al., "The Use of Monosaccharides, Disaccharides, and Trisaccharides in Synthetic Diluents for the Storage of Ram Spermatozoa at 37° C. and 5° C.," Aust. J Biol. Sci. 19:655-671, 1966.

Malonza et al., "Expanded Phase I safety and acceptability study of 6% cellulose sulfate vaginal gel," AIDS 19:2157-2163, 2005.

Mauck et al., "Single and multiple exposure tolerance study of cellulose sulfate gel: a Phase I safety and colposcopy study," Contraception 64:383-391, 2001.

McLaughlin et al., "The contribution of the toxicity of a glycerol-egg-yolk-citrate cryopreservative to the decline in human sperm motility during cryopreservation," Journals of Reproduction & Fertility 95:749-754, 1992.

Moench et al, "Microbicide excipients can greatly increase susceptibility to genital herpes transmission in the mouse," BMC Infectious Diseases 10(331):1-9, 2010.

Moncla et al., "Why Nonoxynol-9 May Have Failed to Prevent Acquisition of Neisseria gonorrhoeae in Clinical Trials," Sexually Transmitted Diseases 32(8):491-494, 2005.

Moncla et al., "Killing of Neisseria gonorrhoeae, Streptococcus agalactiae (Group B Streptococcus), Haemophilus ducreyi, and Vaginal Lactobacillus by 3-O-Octyl-sn-Glycerol," Antimicrobial Agents and Chemotherapv 52(4):1577-1579, 2008.

Morbeck et al., "Washing mineral oil reduces contaminants and embryotoxicity," Fertility and Sterility 94(7):2747-2752, 2010.

Obara et al., "Changes in molecular weight of hyaluronan and hyaluronidase activity in uterine cervical mucus in cervical ripening," Acta Obstet Gynecol Scand 80:492-496, 2001.

Seol et al., "Randomized Controlled Trial for Salvia sclerea or Lavandula angustifolia: Differential Effects on Blood Pressure in Female Patients with Urinary Incontinence Undergoing Urodynamic Examination," The Journal of Alternative and Complementary Medicine 19(7):664-670, 2013.

Seol et al., "Antidepressant-like effect of Salvia sclarea is explained by modulation of dopamine activities in rats," Journal o(Ethnopharmacologv 130:187-190, 2010.

Shin et al., "Inhibition of Immediate-Type Allergic Reactions by the Aqueous Extract of Salvia Plebeia" Immunopharmacology and Immunotoxicology 24(2):303-314, 2002.

Sienkiewicz et al., "The effect of clary sage oil on staphylococci responsible for wound infections," Postep Derm Alergol 32(1):21-26, 2015.

Sutton et al., "To Lube or Not to Lube: Experiences and Perceptions of Lubricant Use in Women With and Without Dyspareunia," J Sex Med 9:240-250, 2012.

Tavakkoli et al., "Carthamus, Salvia and Stachys species protect neuronal cells against oxidative stress-induced apoptosis," Pharmaceutical Biology 52(12):1550-1557, 2014.

Van Damme et al., "Effectiveness ofCOL-1492, anonoxynol-9 vaginal gel, on HIV-1 transmission in female sex workers: a randomized controlled trial," Lancet 360:971-977, 2002.

(56) References Cited

OTHER PUBLICATIONS

Van de Wijgert et al., "The Vaginal Microbiota: What Have We Learned after a Decade of Molecular Characterization?" PLOS ONE 9(8):1-10, e1 05998, 2014.

Vargas et al., "Sperm toxicity of "nonspermicidal" lubricant and ultrasound gels used in reproductive medicine," Fertility and Sterility 95(2):835-836, 2011.

Wang et al., "IgG in cervicovaginal mucus traps HSV and prevents vaginal Herpes infections," Mucosa! Immunol. 7(5):1036-1044, 2014.

Wasiela et al., "Korelacja Stezen Wybranych Cytokin W Wydzielinie Pochwowo-Szyjkowej U Ciezamych Kobiet Z Roznymi Mikroskopowymi Obrazami Tej Wydzieliny," Med. Dosw. Mikrobiol. 57:327-333, 2005.

Wen et al., "Angelica Sinensis Polysaccharides Stimulated UDP-Sugar Synthase Genes through Promoting Gene Expression of IGF-1 and IGFJR in Chondrocytes: Promoting Anti-Osteoarthritic Activity," PLOS ONE 9(9):1-10, e1 07024, 2014.

WHO/UNFPA/FHI360, "Use and procurement of additional lubricants for male and female condoms: WHO/UNFPA/FHI360," Advisory note, Retrieved from: http://aoos.who.int/iris/bitstream/10665/76580/I/WHO RHR 12.33 eng.pdf, 8 pages, 2015.

Wikipedia, "List of *Salvia* species," retrieved from: http://en.wikipedia.org/wiki/List of *Salvia* species, 25 pages, 2015.

Yang et al., "Effects of Salvia sclarea on chronic immobilization stress induced endothelial dysfunction in rats," Complementary and Alternative Medicine 14(396):1-5, 2014.

Yildiz et al., "Influence of Sugar Supplementation of the Extender on Motility, Viability and Acrosomal Integrity of Dog Spermnatozoa During Freezing," Theriogenology 54:579-585, 2000.

Zhang et al., "Diterpenoids from Saliva Plebeia R. Br. and Their Antioxidant and Anti-Inflammatory Activities," Molecules 20:14897-14888, 2015.

Zhong et al., "Sclareol exerts anti-osteoarthritic activities in interleukin-IP-induced rabbit chondrocytes and a rabbit osteoarthritis model," Int J Clin Exp Pathol. 8(3):2365-2374, 2015.

\* cited by examiner

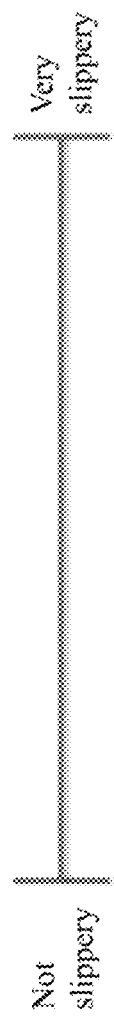
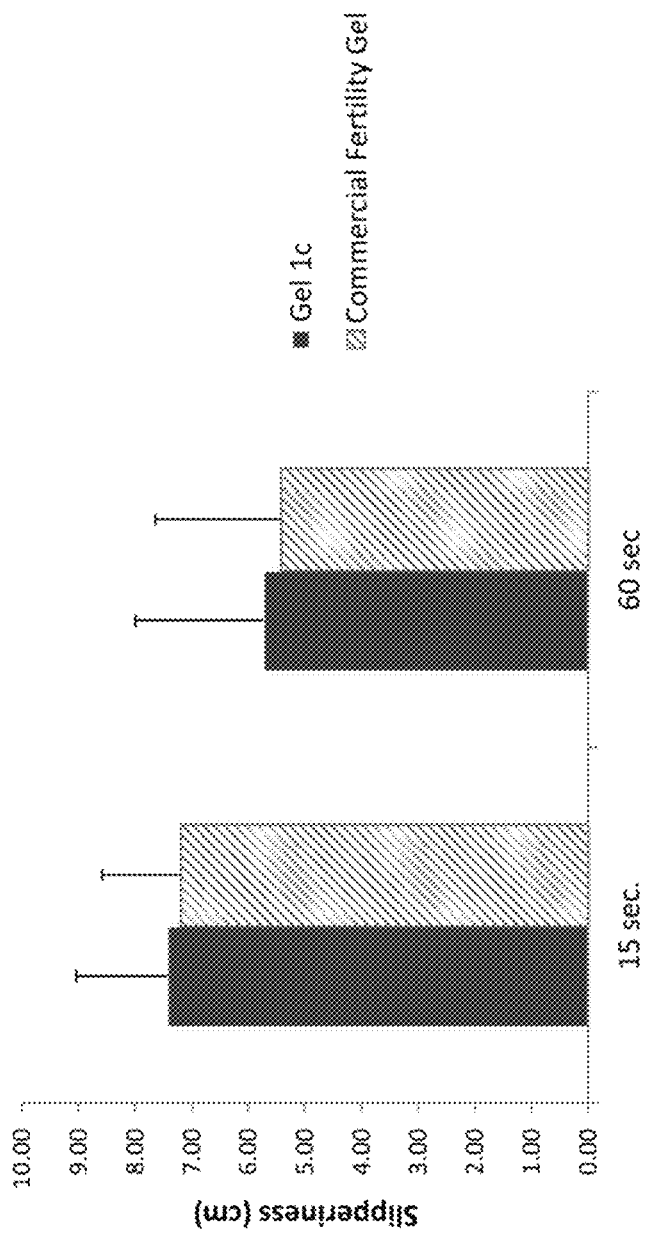
Fig. 9A
Fig. 9B ns> # COMPOSITIONS AND METHODS FOR MAINTAINING OR ENHANCING HOMEOSTASIS OR FUNCTION OF FEMALE LOWER REPRODUCTIVE TRACT This application is a continuation of U.S. patent application Ser. No. 15/894,739, filed Feb. 12, 2018, now U.S. Pat. No. 10,357,527, which is a continuation of U.S. patent application Ser. No. 15/351,097, filed Nov. 14, 2016, now U.S. Pat. No. 9,919,018, which is a continuation of U.S. patent application Ser. No. 15/207,307, filed Jul. 11, 2016, now U.S. Pat. No. 9,913,871, which claims priority to U.S. Provisional Patent Application Ser. No. 62/323,516, filed Apr. 15, 2016. The content of each aforementioned disclosure is incorporated herein by reference.

BACKGROUND

Mounting evidence indicates that cells lining the lower female reproductive tract (LRT), including that of the vulva, vagina and external cervix, together with the resident commensal, vaginotropic microbiome (collectively, the "vaginal ecosystem"), form a dynamic organ that not only protects against infectious disease but also maintains tissue health and facilitates reproduction. The vaginal ecosystem is made up of a variety of factors that together act to support homeostasis of this ecosystem, including immune active cells, a protective mucus coating, a variety of antimicrobial peptides, and symbiotic bacteria (e.g., Lactobacilli).

To maintain homeostasis, the vaginal ecosystem must adapt to changes that occur during a woman's monthly hormone cycle, as well as adjust to more profound changes that happen at different times in the arc of a woman's life, such as puberty, reproductive years, and menopause. For example, during various stages of a woman's reproductive cycle, the vaginal ecosystem is continually providing a protective barrier to disease while at the same time lubricating the vagina to accommodate for sexual intercourse, or facilitating the passage of blood out of the uterus at menses, or inhibiting/optimizing sperm transport through the vagina and cervix, or undergoing chemical changes to promote labor and birth of a baby.

Throughout a woman's life, the LRT and vaginal ecosystem continually experience various disturbances (acute and chronic) caused by human behavior (e.g., sexual intercourse), but also by the use of contraception and vaginal products (Hickey et al., *Transl. Res.* 160:267, 2012; Ma et al., *Annu. Rev. Microbiol.* 66:371, 2012). If disturbance of the vaginal ecosystem becomes chronic, then discomfort, and even disease, can ensue. Any vaginal product that alters the mucosal environment and impairs the epithelial barrier may increase the severity of symptoms or risk of disease (Fichorova et al., *Toxicol. Appl. Pharmacol.* 285:198, 2015; Ma et al., 2012).

The consequence of products for women's health that ignores the full biology of the LRT and the vaginal ecosystem has been costly at both the epidemiologic and personal level. Vaginal products developed to prevent Sexually Transmitted Diseases (STDs) were actually found to cause an increase in STD rates when tested in clinical trials (Gali et al., *Antimicrob. Agents Chemother.* 54:5105, 2010; Dezzutti et al., *PLoS One* 7:e48328, 2012). Cell toxicity of various ingredients (some are referred to as "inactive carriers") in vaginally applied products, for both the healthy vaginotropic bacteria and the vaginal mucosal epithelial cells, is pervasive and is evident at concentrations below those found in common vaginal products.

Safer LRT product compositions to aid in women's health are needed, such as products designed to preserve and support the vaginal ecosystem homeostasis and healthy function thereof. Presently disclosed embodiments address this need and provide other related advantages.

BRIEF DESCRIPTION OF THE DRAWINGS

FIGS. 9A and 9B: FIG. 9A depicts a 10 cm visual analog scale (not drawn to scale) for evaluating slipperiness of Fertility Gel 1c and a paraben-containing commercial fertility gel. FIG. 9B is a bar graph depicting the degree of slipperiness Fertility Gel 1c and a paraben-containing commercial fertility gel as measured by the distance (cm) of the participants marking on the visual analog scale.

DETAILED DESCRIPTION

Figure 1:
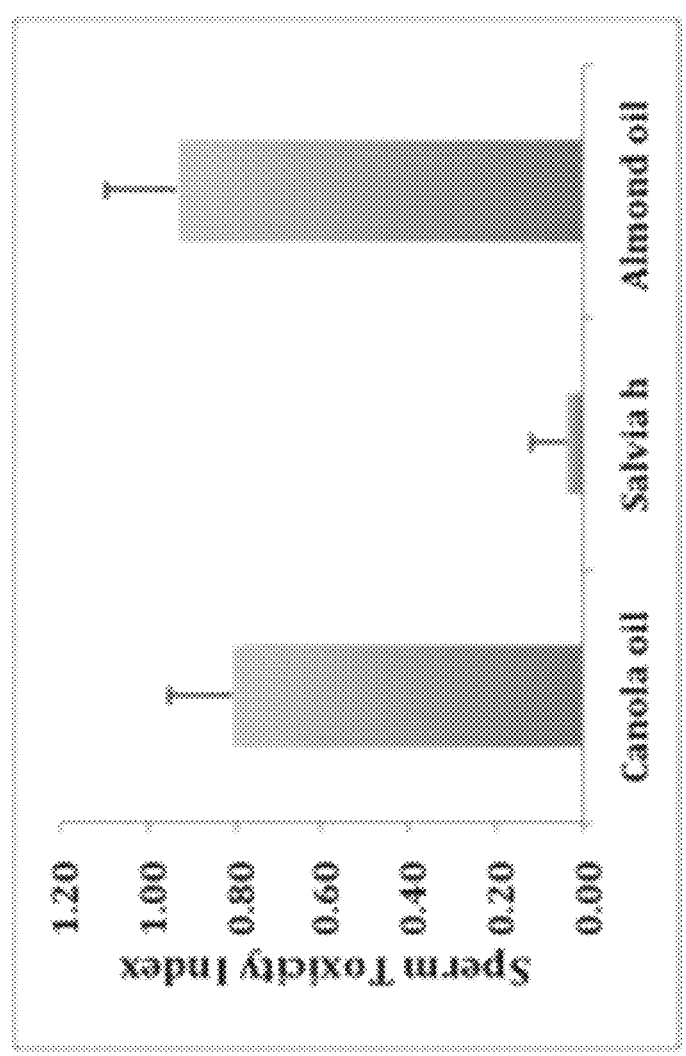
FIG. 1 is a bar graph depicting the effect on sperm when contacted with an isotonic, neutral pH (pH 7) solution with 10% *Salvia hispanica* extract (in an oil format) as compared to canola oil and almond oil. A Sperm Toxicity Index of <0.75 is considered cytotoxic to the sperm.

The present disclosure provides compositions and methods for maintaining or enhancing homeostasis, function or both of the female lower reproductive tract (LRT). In particular, the instant disclosure relates to unique isotonic, biome-friendly formulations comprising xylose and a *Salvia* extract at various pH levels to complement unique hormone cycle and life-stage specific physiology and function of the female LRT. Such isotonic, biome-friendly formulations of xylose and *Salvia* are useful for prophylactically or therapeutically promoting and maintaining a natural balance in the female LRT environment, including the vaginal ecosystem. More specifically, isotonic, biome-friendly formulations of this disclosure can be used for treating or preventing infection, preventing conception, enhancing fertility, maintaining or enhancing vaginal ecosystem homeostasis, increasing hydration of the vaginal mucosa, or the like.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. Any concentration ranges recited herein are to be understood to include concentrations of any integer within the range and fractions thereof, such as one tenth, one hundredth, and one thousandth of an integer, unless otherwise indicated. As used herein, the term "about" means ±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

A "pharmaceutical composition" or "vaginal composition" refers to a formulation of this disclosure and a medium generally accepted in the art for the delivery of the biologically effective compound(s) to female subjects, e.g., humans. For example, a pharmaceutical or vaginal composition of the present disclosure may be formulated or used as a stand-alone composition, or as a component in a prescription drug, an over-the-counter (OTC) medicine, a botanical drug, an herbal medicine, a medical device, a cosmetic, a homeopathic agent, or any other form of health care product, optionally reviewed and approved by a government agency. A medium generally accepted in the art includes all pharmaceutically or vaginally acceptable carriers, diluents or excipients therefor.

As used herein, "enriched for" refers to a plant extract or other preparation having at least a two-fold up to about a 1000-fold increase of one or more active compounds as compared to the amount of one or more active compounds found in the weight of the plant material or other source before extraction or other preparation. In certain embodiments, the weight of the plant material or other source before extraction or other preparation may be dry weight, wet weight, or a combination thereof.

As used herein, "purified" refers to a plant extract or other preparation that has at least one contaminant removed therefrom or the removal of a desired component from the milieu. In certain embodiments, the plant extract is purified using a method selected from distillation, recrystallization, precipitation, solvent partition, chromatographic separation, or other suitable methods.

As used herein, "major active ingredient" or "major active component" refers to one or more active compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than 50%, 25%, or 10% of the components contained in an extract) but still provide most of the desired biological activity. Any composition of this disclosure containing a major active ingredient may also contain minor active ingredients that may or may not contribute to the pharmaceutical or vaginal activity of the enriched composition, but not to the level of major active components, and minor active components alone may not be effective in the absence of a major active ingredient.

"Effective amount" or "therapeutically effective amount" refers to that amount of a composition of this disclosure which, when administered to a female mammal, such as a human, is sufficient to effect a desired biological effect or treatment, including any one or more of: (1) improving or promoting perineal elasticity to lessen trauma or tearing of the perineum during birth; (2) maintaining, supporting or promoting vaginal homeostasis; (3) providing contraceptive activity that impairs sperm function and penetration; (4) promoting fertility by maintaining or improving sperm survival, function, or penetration into cervical mucus; (5) hydrating and lubricating mucosal (vaginal) surface in reproductive-aged women or post-menopausal women; (6) protecting, cleaning, balancing or restoring feminine freshness in the vaginal area; (7) toning vulvar and vaginal tissues; and (8) providing a muco-adhesive carrier for medications for adherence to and retention by the vaginal wall. The amount of a composition of this disclosure that constitutes an "effective amount" will vary depending on the formulation, the condition being treated and its severity, the manner of administration, the duration of treatment, or the age of the subject to be treated, but can be determined routinely by one of ordinary skill in the art having regard to his own knowledge and to this disclosure.

"Lower Reproductive Tract (LRT) compositions" refer to combinations of ingredients of this disclosure that improve, promote, increase, manage, control, maintain, optimize, modify, reduce, inhibit, or prevent a particular condition associated with the female vaginal ecosystem. For example, with regard to reproductive-related activities, LRT supplements may be used to promote hydration, lubrication, fertility, vaginal microbiome balance, or the like. Exemplary LRT compositions include xylose and a *Salvia* extract, optionally containing one or more additional ingredients for use in the vaginal ecosystem, such as a viscosity-increasing agent, a surfactant, a buffering agent, an osmolality adjuster, a pH modifier, a solvent, a preservative (e.g., paraben-free), a humectant, or any other substance useful for supplementing, maintaining or improving LRT homeostasis.

The "vaginal microbiome" or "vaginal biome" refers to the vaginal microbiota, as well as the products of the vaginal microbiota and the host LRT environment.

"Biome-friendly" when used in reference to LRT compositions means that the compositions of this disclosure that are contacted with the female LRT will exhibit minimal mucosal irritation, inflammation or immunotoxicity, as well as provide a supportive environment for vaginal microbiota.

The LRT compositions of the present disclosure may be administered to a mammalian female or a male subject, including humans, bovine, canine, feline, equine, porcine, ovine, avian, rodent, lagomorph, caprine, non-human primate, or other exotic species.

Female Lower Reproductive Tract (LRT)

A woman's lower reproductive tract (LRT) refers to the vulva (including the perineal tissues), the vagina, and the ectocervix (i.e., that portion of the cervix visible inside the vagina covered by squamous epithelium). The vagina and ectocervix that comprise the birth canal are covered with non-keratinized stratified squamous epithelium, including numerous epithelial anchored mucin producing cells. Aspects of the physiology of this mucous membrane are unique to the LRT. The LRT is that portion of the female reproductive anatomy that can be contacted with lotions, creams, gels, douches, films, powders, sprays, or the like, which are included in products marketed for female hygiene and health care. These products can be in the form of cosmetics, medical devices or drugs, which are used for personal hygiene, contraception, lubrication, hydration, childbirth, assisted reproduction, disease treatment or aesthetics.

The vulva (the external genital organs) includes the mons pubis, labia majora, labia minora, Bartholin glands, and clitoris. The external genital organs have three primary functions: enabling sperm to enter the body, protecting the internal genital organs from infection, and providing sexual pleasure. The mons pubis and labia majora are lined with skin, mucus producing glands, and sweat and sebaceous glands. The labia minora is lined with a moist mucosal membrane, which is kept hydrated, similar to the vagina, through mucus secreting cells. Bartholin glands also secrete mucus for lubrication during intercourse.

LRT Homeostasis and Function

Homeostasis and function of the LRT, including the surface of the vulvar skin, the extracellular milieu of the vulva and vagina, and the vaginal canal, is affected by a variety of factors, including ecosystem pH, composition of sugar-protein complex (glycoproteins and mucins), innate and adaptive immune system factors and cells, the normal microbiome, the presence or absence of pathogens, systemic and local hormone levels, environmental factors, and the like.

A woman's LRT and, in particular, the vaginal ecosystem, has a particular pH and comprises a diverse population of cell types, including epithelial cells, immune cells, vaginal microbiota, and at times, a partner's sperm cells and invading pathogens from the external world. One important evolutionary aspect of a woman's LRT is the need to allow sperm penetration into the higher reproductive tract for procreation, while at the same time limiting invading pathogens, especially the highly mutually evolved sexually transmitted diseases (STDs) that can also be present with semen.

As used herein, the term "vaginal microbiota or "VMB," also referred to as "vaginal flora," refers to the collective microorganisms that normally colonize the vulva and vagina and are non-pathogenic. In general, the VMB is primarily comprised of different strains of *Lactobacillus* (or related acid-producing bacterial types), which produce lactic acid to keep the vaginal ecosystem as a tightly controlled acidic environment during much of a woman's monthly cycle in reproductive aged women (pH of about 3.5-5.5). Exemplary VMB species include *Lactobacillus acidophilus, Lactobacillus jensenii, Lactobacillus gasseri, Lactobacillus finers, Lactobacillus crispatus, Lactobacillus plantarum, Lactobacillus fermentum, Lactobacillus brevis, Lactobacillus casei, Lactobacillus delbrueckii, Lactobacillus vaginalis, Lactobacillus salivarius*. Other lactic-acid producing bacteria that may be part of the VMB include species of *Atopobium, Leptotrichia, Leuconostoc, Megasphaera, Pediococcus, Streptococcus* and *Weissella*. The species found in normal VMB can differ between ethnic groups. Lactobacilli have been shown to inhibit in vitro growth of pathogenic microorganisms, e.g., *Bacteroides fragilis, Escherichia coli, Gardnerella vaginalis, Mobiluncus* spp., *Neisseria gonorrhoeae, Peptostreptococcus anaerobius, Prevotella bivia* and *Staphylococcus aureus*. This inhibitory action is thought to be achieved mainly through the action of lactic acid (Graver and Wade, *Ann. Clin. Microbiol. Antimicrob.* 10:8, 2011; Matu et al., *Anaerobe* 16:210, 2010; Skarin and Sylwan, *APMIS* 94:399, 1986; Strus et al., *J. Reprod. Med.* 47:41, 2002).

Furthermore, lactobacilli may help prevent pathogenic organisms from adhering to vaginal epithelial cells (Boris and Barbes, *Microb. Infect.* 2:543, 2000). Other inhibitory mechanisms of lactobacilli include production of hydrogen peroxide and bacteriocins (Martin and Suarez, *Appl. Environ. Microbiol.* 76:400, 2010; Aroutcheva et al., *Am. J. Obstet. Gynecol.* 185:375, 2001). While low pH is one factor in LRT homeostasis, the LRT of healthy women is not always maintained at a low pH. The vaginal environment is episodically exposed to natural secretions with a neutral pH (about 7). More specifically, this exposure includes blood flow from the uterus during menses; semen from a partner after sexual intercourse; and fertile cervical mucus production during ovulation. These cyclical disruptions in vaginal pH are transient and rapidly accommodated with a return to an acidic pH level in women with healthy LRT function. Before puberty, during pregnancy and after menopause, a healthy pH of a woman's LRT physiologically rests at a pH of about 4.5 to about 6.8. In short, simple maintenance of an acidic pH does not define LRT homeostasis, but rather a healthy LRT will maintain homeostasis and function while undergoing normal variations in pH depending on a woman's hormone cycle and stage of life, among other factors.

Most healthy women have a stable VMB throughout their lives, but a woman's VMB can change depending on what reproductive stage of life she is in, e.g., pregnancy, puberty, and menopause. The vaginotropic, "healthy" VMB is in large part derived from the woman's mother during her birth. Over 112 different strains of *lactobacillus* and related commensal bacteria have been identified in the vagina. Disruptions in the VMB and vaginal ecosystem can cause numerous serious diseases, such as bacterial vaginosis, vaginitis, postpartum infections, increased STD rates (including HIV), and pre-term labor (van de Wijgert et al., *PLoS One* 9:e105998, 2014). In short, a stable VMB in women contributes to the maintenance of LRT homeostasis, which has significant public health importance.

Another contributor to the homeostasis and function of the LRT are local proteoglycans (PG) and glycosaminoglycans (GAGs). PGs are a major component of the human extracellular matrix, the area existing between cells and at cell surfaces in an organism. Individual functions of PGs can be attributed to the GAG molecules attached to them. GAGs are long unbranched polysaccharides containing a repeating disaccharide unit. GAGs create viscous environments wherever they are present, which is primarily on the surface of cells, in the extracellular matrix or in secretory vesicles of some types of cells. Natural lubricating gel substances produced by the human body are composed of GAGs and are involved in a variety of physiological functions, including skin hydration, joint function, sexual function, and reproduction. The type and quantity of GAGs and PGs in female reproductive tissues changes based on hormonal fluctuations and stage of life.

Assembly of functional GAGs is initiated in animal cells by transferring a xylose residue to specific serine residues in a PG core protein (Lugemwa et al., *J. Biol. Chem.* 271: 19159, 1996). Additional sugar units attach to the protein PG core through the xylose sugar residue to form a chain, which eventually folds into a unique biologically active substance. Interestingly, different combinations of single sugars and/or GAG fragments in solution cannot mimic the biological impact of these same GAG combinations when attached to a xylose molecule on a PG backbone to form a large folded molecule (Tran et al., *ACS Chem. Biol.* 8:949, 2013). Attachment to the PG core through a xylose molecule allows the carbohydrates in the GAG to fold into their biologically functional shape.

Along with ensuring high viscosity of body fluids (e.g., cervical mucus, semen), GAGs provide structural integrity for passageways between cells, allowing for cell migration, such as sperm transport. The specific GAGs of physiological significance are hyaluronic acid (HA), dermatan sulfate, chondroitin sulfate, heparin/heparan sulfate, and keratan sulfate. GAGs are important in many aspects of reproduction.

Xylose concentration in tissues and the concentration of the xylosyltransferase (XT) enzyme, which is the first enzyme involved in sugar chain attachment to the PG backbone) are highly correlated to the level of functional GAGs produced. The XT enzyme regulates the biosynthesis of sugar chains attaching to the PG, and thereby the functionally present GAGs. The XT activity in body fluids is an indicator of the current PG biosynthesis rate. This is because XT catalyzes the initial and rate limiting steps of attaching the carbohydrate sugars to the protein PG backbone at the xylose residue (Muller et al., 2013, Glycoconj. J. 30:237-45). Xylose levels and xylosyltransferase activity has been shown in vivo and in vitro studies to be regulators of GAG biosynthesis (Nadanaka & Kitagawa, *Matrix Biol.* 35:18, 2014), the level of which is considered important for maintaining tissue homeostasis under normal and pathological conditions. Altered XT activity in the human body also correlates with various chronic diseases (Kuhn et al., *Biochem. Biophys. Res. Commun.* 459:469, 2015), where mucus and mucin production and tissue health are compromised.

The biological function of PG and GAGs can also be observed in the reproductive tract where these factors preserve sperm motility and the velocity at which the sperm swim, provide arousal fluids to facilitate sexual intercourse, as well as provide cervical mucus (CM) production throughout different stages of reproduction.

The contribution of PG and GAG fluctuations in the LRT homeostasis and function is also evident in the changes in the type of GAG seen in the cervix prior to birth, as a part of cervical "ripening" (Fischer et al., *J. Soc. Gynecol. Investig.* 8:277, 2001). The molecular weight of GAGs change at specific stages of labor as compared to other times (Obara et al., *Acta Obstet. Gynecol. Scand.* 80:492, 2001). These changes appear to relate to epithelial barrier protection of the LRT. Specifically, females with GAG depletion in the cervix and vagina during pregnancy have increased mucosal permeability and a "striking" increase in preterm births. GAGs in the vaginal canal and cervical mucus help maintain a mucosal barrier to limit pathogen infiltration (Akgul et al., *Endocrinol.* 153:3493, 2012; Akgul et al., J. Clin. Invest. 124:5481, 2014; Ulrich et al., *PLoS One* 9:e104972, 2014). Factors that disrupt this highly tuned physiology of PG and GAG in the LRT will also affect LRT homeostasis, which can be harmful to the woman.

Inflammation can reduce GAG formation and chain length. When cartilage cells are challenged in the laboratory with interleukin (IL) cytokines, total xylose residues in the PGs are reduced, thus limiting the opportunity for beneficial lubricating GAGs to form (Frankenberger et al., *Connect. Tissue Res.* 54:123, 2013).

Iyibozkurt et al. (*Reprod. Biomed Online.* 19:784, 2009) teach that changes in GAG physiology can change cellular function. For example, vascular endothelial growth factor (VEGF) improves sperm motility, but not sperm viability. The GAG-binding domain of VEGF has no significant sequence or structural similarity to any other known proteins and, thus, represents a novel heparin-binding domain (Fairbrother et al., *Structure* 6:637, 1998), which could be involved in enhancing sperm function.

Mucins are another form of glycosylated protein that can impact LRT physiology and homeostasis. Mucins are O-linked glycoproteins produced by cells that establish a physical barrier against undesirable entry of foreign materials across epithelial surfaces. They are ubiquitous in mucous secretions on cell surfaces and in body fluids (Brockhausen et al., 2009, *O-GalNAc Glycans*. In: Varki A, Cummings R D, Esko J D, Freeze H H, Stanley P, Bertozzi C R, Hart G W, Etzler M E, editors. Essentials of Glycobiology. $2^{nd}$ ed. Cold Spring Harbor (N.Y.): Cold Spring Harbor Laboratory Press; Chapter 9) and are either secreted or membrane bound (Gosalia et al., *J. Biol. Chem.* 288:6717, 2013).

Mucins function to hydrate and lubricate epithelial tissues (Andrianifahanana et al., *Biochim. Biophys. Acta* 1765:189, 2006), and they also function in cell renewal, transport, signaling and adhesion. Mucin homeostasis is maintained by elaborate coordinated regulatory mechanisms providing a well-defined specific distribution. But, mucin homeostasis can be disrupted by environmental or intrinsic factors. Changed gene activation can be triggered by cytokine inflammatory agents. Resulting mis-expression can change the mucus quality being produced. Deregulated mucin is associated with many types of cancer and inflammatory disease. The genes that control mucin production form a cluster that balances the different types of mucin products present. In cancer and during disease exposure, this mucin profile is changed. Increase in bacterial lipopolysaccharide (LPS) activates mucin gene expression. For example, LPS at 200 ng/ml induced a 50% increase in several mucins and 25% decrease in others (Gosalia et al., *J. Biol. Chem.* 288:6717, 2013). Non-LPS mediated inflammation can also result in mucin changes. For example, inflammatory mediators in the tears of "dry eye" patients change the eye surface mucins, making them less lubricating. (Albertsmeyer et al., 2010, Exp. Eye Res. 90:444-451). Many diseases involve abnormal mucin secretion. Normal mucin expression offers an important feedback to the mucin gene cluster to further retain normal mucin and tissue homeostasis needed for optimal LRT function.

Membrane-tethered mucins line all wet surfaces of the body, but those of the LRT have the unique characteristic of fluctuating during a woman's hormonal cycle to allow at different times support for outflow of menses blood from the uterus, the rapid transport of sperm cells into the Fallopian Tube during ovulation, and the passage of a baby and placenta at child birth, all while stopping highly pathogenic bacteria from ascending to infect the host.

LRT mucins do much more than just hydrate the vaginal canal (Govindarian & Gipson, *Exp. Eye Res.* 90:655, 2010). Mucins in the vagina define a zone between the epithelial cell layer and the external environment (the vaginal lumen). They create a 40-100 nm thick carbohydrate coating that is anchored to the epithelium by proteins. This mucous layer excludes organisms that are larger than 100 nm from directly contacting and infecting the vaginal mucosal cell surface. For comparison, sperm are about 50 µm in size. But, these mucins have been difficult to study because they are large, and their functional biochemistry is inseparable from their physical biochemistry, which is interactive with all the cells that make up the vaginal ecosystem (Kesimer & Sheehan, *Glycobiol.* 18:463, 2008).

In the LRT, carbohydrate-rich mucus is secreted by vaginal epithelial cells and by cervical cells into the vaginal canal. This cervical mucus (CM) contributes to homeostasis and physiologic functioning of a woman's LRT, which is a complex matrix of GAGs, mucins and other factors, such as proteins and enzymes (Curlin and Bursac, *Front. Biosci.* 5:507, 2013). CM mucins are packaged in secretory granules and released, where they swell to become a hydrogel in the vaginal canal (Espinosa et al., *Hum. Reprod.* 17:1964, 2002). Mucin hydration and gel formation are tightly controlled in the vagina and cervix by changes in calcium and pH levels. For example, an increase of calcium levels in the vaginal lumen from 1 mM to 4 mM or a reduction in pH from 7.4 to 6 can decrease the speed at which CM mucin granules are hydrated and spread through the vagina, thereby negatively impacting sperm transport.

Overall, CM is composed of about 82% mucins, 3% HA, 2% heparin sulfate and 13% dermatan sulfate (Uldbjerg et al., 1983, Gynecol. Obstet. Invest. 16:199-209). Andersch-Bjorkman et al. (2007, *Mol. Cell Proteomics* 6:708) teach that altered mucus properties are correlated with fertility failure. The major mucin of CM is MUC5B, which peaks at ovulation and is involved in sperm transport. Three gel forming mucins are present in CM including MUC5B, MUC5AC, MUC6; and two transmembrane mucins are present, including MUC1 and MUC16 (which is not found anywhere else in the female reproductive tract). CM interestingly contains several enzymes (such as amylase) also present in saliva.

For most of a woman's cycle, CM is scant, dry, sticky and thick, which acts to block sperm and bacteria from ascending up the reproductive tract. But during ovulation, when the woman's estrogen levels rise, the CM can show a marked increase in water content and volume (up to 20-fold). The fertile CM develops an "egg-white" quality, as it becomes more slippery with a lower viscosity. Fibers in the fertile CM line up to form passageways for the sperm to rapidly penetrate through the cervix to reach the Fallopian tube, where the egg is waiting to be fertilized (Chretien, *Acta Obstet. Gynecol. Scand.* 82:449, 2003). During ovulation, increases in circulating estrogen increase water flow thru the vaginal lining cells. This increased water in the vaginal canal hydrates secreted CM mucin granules to form the egg-white "fertile" CM. During hormone changes at ovulation, the vaginal environment supports fertile CM production through enhancing water flow to hydrate the secreted CM granules, decreasing calcium levels and a lowering of pH to stabilize and protect sperm. At ovulation, secreted granules of these mucins begin to swell within 10 seconds after release from the epithelial cell, and they are totally dispersed within 30 minutes. Increased calcium levels reduce this expansion by one order of magnitude. Lowering of pH from 7 to 6.5 also results in an overall 20-fold reduction in mucin granule swelling. Therefore, loss in homeostasis in the LRT and particularly in the vaginal environment during ovulation can easily lead to thicker, less viscous CM that impedes sperm movement and fertility. Abnormal or "hostile" cervical mucus that blocks sperm penetration into the Fallopian Tube during ovulation is a common cause of female infertility, with no current treatment.

Sperm cells and semen can also be a part of a healthy LRT and vaginal ecosystem. During ovulation, a woman's body optimizes this environment to support selection of healthy sperm to participate in fertilization. Contact of sperm with cervical mucins causes a dose related increase in sperm velocity and linearity (straight swimming) that helps them reach the egg (Eriksen et al., *Fertil. Steril.* 70:350, 1998).

A multitude of other changes in CM occurs during ovulation, including the switch from production of acidic sugars to neutral ones, to allow pH elevation needed for sperm transport. Also Van der Linden et al. (1992, Fertil. Steril. 57:573-7) showed a pre-ovulatory decrease in fructose and glucose in CM, which likely maximizes sperm function. It is known that the CM provides an active selection gradient for the highest quality sperm in the ejaculate. Sperm that penetrate into the CM tend to have superior DNA quality (Bianchi et al., *J. Assist. Reprod. Genet.* 21:97, 2004) and lower lipid content, which prevents over active oxidation damage (Feki et al., *Mol. Hum. Reprod.* 10:137, 2004). Also, contrary to the image of sperm "battling through" the cervical canal, out of the 250 million sperm deposited in a normal human ejaculate, only 200 sperm end up in the Fallopian Tube near the site of fertilization. These sperm may actually be rapidly transported by the woman's reproductive tract through the cervix and out of the vaginal environment. Sperm transport out of the vagina is seen in as little as 90 seconds and is primarily complete within 30 minutes after intercourse. The concerted actions of the LRT to ensure selection of the best sperm for reproduction highlight the importance of vaginal ecosystem homeostasis for overall healthy reproductive function.

Human sperm becomes capable of fertilizing the egg following enzyme changes (e.g., tyrosine phosphorylation) in the sperm membrane. If sperm are to participate in fertilization, this shift cannot occur before sperm meet the egg in the Fallopian Tube, but this physiologic change was recently observed for sperm bound to GAG hyaluronic acid (HA) (Sati et al., *Reprod. Sci.* 2:573, 2014). In fact, sperm activation is exactly the same if sperm are bound to an egg or to HA. Normally HA is a small component of CM at ovulation (just 3%), but changes in CM GAG composition could lead to abnormal sperm changes. In certain embodiments, compositions of this disclosure can be vaginally applied formulations that alter GAG composition in the LRT (optionally with an HA based lubricant) to promote or enhance LRT homeostasis in the context of fertility.

A. Compositions

Methods and compositions to maintain, preserve, promote, improve or enhance LRT homeostasis and healthy ecosystem function during cosmetic, prophylactic, and therapeutic interventions for the vulva, vagina and ectocervix are provided herein. Also provided herein are methods and compositions to maintain, preserve, promote, improve, enhance, or increase sperm, oocyte, or embryo function or survival (e.g., during assisted reproduction procedures). In certain embodiments, compositions of this disclosure comprise isotonic formulations at a pH ranging from about 3.0 to about 8.0 that contains xylose and a *Salvia* extract. These compositions are for topical application to support life-stage specific aspects (e.g., reproductive, post-menopausal) of LRT physiology and function. Preferably, the xylose/*Salvia* extract compositions further comprise additional components, such as a viscosity-increasing agent, a surfactant, a buffering agent, an osmolality adjuster, a pH modifier, a solvent, a preservative (e.g., paraben-free), a humectant or any combination thereof. The inclusion of one or more these additional components will be dictated by the particular use (e.g., vaginal freshening, perineal massage, fertility, vaginal hydration).

The compositions and methods provided herein are designed to work in concert with the LRT ecosystem in a safe and highly efficacious manner to support and potentiate physiologic functions at different stages in a woman's life and promote LRT homeostasis. Furthermore, in certain embodiments, compositions of the present disclosure can also function to promote healthy immune system function without overstimulation. For example, without wishing to be bound to any particular theory of mechanism of action, compositions of the present invention can prevent or treat a condition or symptom(s) of inflammation by reducing the activation of the innate and/or acquired immune system and production of pro-inflammatory cytokines.

Specifically, the methods and compositions of this disclosure provide isotonic, biome-friendly compositions designed for topical application to support LRT function and promote LRT homeostasis. The pH of the compositions of this disclosure will differ according to uses directed to different life-stage specific events (e.g., trying-to-conceive, pregnancy, menopause) or hormonal cycle of a woman (e.g., ovulating or luteal phase of the cycle).

In certain aspects, compositions of the present disclosure comprise an isotonic, biome-friendly composition containing xylose and a *Salvia* extract, wherein the composition is formulated for topical application and has a pH ranging from about 3.0 to about 8.0.

Xylose is an aldopentose type monosaccharide having a chemical formula of $C_5H_{10}O_5$ that is a building block for the hemicellulose xylan and is also the first saccharide added to serine of proteoglycans by O-linked glycosylation. Xylose can be obtained from the xylan-rich portion of hemicelluloses present in plant cell walls and fiber and is also called "wood sugar." Xylose is commercially available in purified form from a variety of vendors (e.g., Sigma-Aldrich, St. Louis, Mo.). Xylose may also be extracted and purified from a variety of plant sources, including wood, straw, corn, coconut shell, sugar cane bagasse, raspberries, loganberries, blackberries, guava, pears, broccoli, spinach, eggplant, peas, green beans, okra, cabbage, aloe vera, echinacea, boswellia, psyllium seeds, jute stick, rice husk, birch, alfalfa, leaf wood, apple and citrus pulp, sugar beet, and other plant material. Pectic substances, also referred to as pectins, are a complex mixture of polysaccharides characterized by a backbone of α(1→4) linked galacturonic acid units that are partially methyl-esterified (O'Neill et al., *Meth. Plant Biochem.* 2:415, 1990). All pectins contain some associated neutral sugars, such as L-arabinose, D-galactose, L-rhamnose, D-xylose, and D-glucose. Chemical and enzymatic degradation of pectins reveal long and regular uronic regions (smooth) and rhamnose-rich regions (hairy) that have neutral side sugars as side chains. Pectins are present in the primary cell walls of all seed-bearing plants and are major components of dicotyledons (e.g., citrus and legumes) and gymnosperms (e.g., Douglas fir). Commercially important sources of pectin include apple and citrus pulp, sugar beet, and alfalfa. Methods of extracting and purifying xylose from natural sources are known in the art (see, e.g., Griffin et al., *J. Chem. Tech. Biotech.* 79:505, 2004; Ahmed et al., *J. Biol.*

*Sci.* 1:1001, 2001; Saska and Ozer, *Biotechnol. Bioeng.* 45:517, 1995; and U.S. Pat. No. 3,687,807). D-xylose, which is present in living things, or L-xylose, which can be synthesized, can be used in the compositions disclosed herein. In certain embodiments, compositions of the instant disclosure comprise xylose having at least 90%, 91%, 92%, 93%, 94%, 95%, 96%, 97%, 98%, 99% purity. In some embodiments, xylose is from raspberries.

As discussed herein, carbohydrate GAGs are attached to the protein core of proteoglycans (PGs) through the O-linked xylose sugar residue. In certain embodiments, compositions of this disclosure containing xylose are used to promote, maintain or achieve homeostasis of the vaginal mucosa or the lower reproductive tract. Without wishing to be bound by theory, xylose may stimulate PG and/or GAG synthesis and secretion by vaginal tissues in ways that synchronize with hormonal and life cycle changes of women, or in ways that protect the mucosal ecosystem of the LRT.

In certain embodiments, compositions of the instant disclosure comprise xylose at a concentration ranging from about 0.001% to about 10% by weight, about 0.001% to about 5% by weight, about 0.001% to about 2.5% by weight, about 0.001% to about 1% by weight, about 0.001% to about 0.5% by weight, about 0.01% to about 5% by weight, about 0.01% to about 2.5% by weight, about 0.01% to about 1% by weight, about 0.01% to about 0.5% by weight, about 0.02% to about 1% by weight, or about 0.02% to about 0.5% by weight. In certain embodiments, the concentration of xylose is at about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight. In certain embodiments, the xylose is D-xylose.

Compositions of the present disclosure also comprise a *Salvia* extract. Without wishing to be bound by theory, *Salvia* extracts may function by preserving, improving or enhancing LRT homeostasis and healthy function. By way of background, *Salvia* (common name sage) is the largest genus of plants in the mint family Lamiaceae, which includes almost 1,000 species. The classification of *Salvia* is based on the genus' unusual pollination and stamen structure. *Salvia* species include annual, biennial, or perennial herbs, along with woody subshrubs. Several members of the *Salvia* species have been used for their culinary, aromatherapy and medicinal value (see, e.g., Akhondzadeh et al., *J. Clin. Pharm. Ther.* 28: 53, 2003). There are three main geographical regions of diversity, including Central and South America, Central Asia and Mediterranean, and Eastern Asia.

Exemplary *Salvia* species include *Salvia argentea, Salvia arizonica, Salvia azurea, Salvia candelabrum, Salvia carnosa, Salvia clevelandii, Salvia coccinea, Salvia columbariae, Salvia divinorum, Salvia dorrii, Salvia farinacea, Salvia forreri, Salvia fulgens, Salvia funerea, Salvia glutinosa, Salvia greggii, Salvia guaranitica, Salvia hispanica, Salvia leucantha, Salvia leucophylla, Salvia libanotica, Salvia longistyla, Salvia lyrata, Salvia mexicana, Salvia miltiorrhiza, Salvia patens, Salvia plebeia, Salvia polystachya, Salvia potus, Salvia pratensis, Salvia roemeriana, Salvia sclarea, Salvia spathacea, Salvia splendens, Salvia verticillata,* and *Salvia viridis* (see www.theplantlist.org/1.1/browse/A/Lamiaceae/Salvia for a complete list of *Salvia* species). In certain embodiments, *Salvia* extracts and oils can be used in formulations of this disclosure to promote, improve, maximize or maintain healthy function of the lower female reproductive tract.

In certain embodiments, a *Salvia* extract is a carbohydrate or oil extract from a *Salvia* species, such as an extract from *Salvia plebeia, Salvia sclarea, Salvia hispanica*, or any combination thereof.

*Salvia plebeia* (SP), also known as Asian sage, has been shown to have an anti-inflammatory and antioxidant activity (He et al., *J. Cardiovasc. Pharmacol.* 67:93, 2016), as well as anti-allergenic activity (Shi & Kim, *Immunopharmacol. Immunotoxicol.* 24:303, 2002). *Salvia plebeia* extracts have been shown to reduce bacterial LPS-activated inflammation and cytokine response (Akram et al., *J. Ethnopharmacol.* 174:322, 2015). Several different antioxidant and or anti-inflammatory active compounds have been isolated from SP (Jin et al., *Nat. Prod. Res.* 29:1315, 2015; Akram et al., 2015) including, hispidulin, homoplantaginin, nepetin (two kinds), luteolin (two kinds), caffeic acid, luteoloside, eupatorin, hispidulin and plebeia oil A. These compounds show reactive oxygen species (ROS) scavenging at around 20 as well as production against LPS-induced inflammation and COX-II inhibition, (Akram et al., 2015; Zhang et al., *Molecules* 20:14879, 2015).

*Salvia sclarea* (SS) extract, also known as Clary Sage, has been used as an aromatic essential oil for alleviating symptoms of depression and premenstrual cramps. In fact, 5% clary sage has recently been shown to have the strongest anti-depressant activity of any essential oil tested. This effect is due to its action on dopamine release (Seol et al., *J. Ethnopharmacol.* 130:187, 2010). *Salvia sclarea* extract has also been shown to preserve cell viability and act as an antioxidant (Tavakkoli et al., 2014, *Pharm Biol.* 52:1550-7). The product sclaerol, a compound found in *Salvia sclarea*, inhibited the ability of interleukin induced chondrocytes to trigger inflammatory pathways in vitro (Zhong et al., *In'tl. J. Clin. Exp. Pathol.* 8:2365, 2015).

In addition, *Salvia sclarea* oil has been shown to have antimicrobial activity, including acting synergistically with antibiotics to kill resistant *Staphylococcus* organisms (Chovanova et al., *Lett. Appl. Microbiol.* 61:58, 2015). *Salvia sclarea* has also been shown to be effective at killing common skin pathogens with little subsequent cytotoxicity (Sienkiewicz et al., *Postepy Dermatol. Alergol.* 32:21, 2015; Firuzi et al., *Iran J. Pharm. Res.* 12:801, 2013; Cui et al., *Botanical Studies* 56:1, 2015).

The International Federation of Professional Aromatherapists recently issued a Pregnancy Guidelines (2013) (www-.naha.org/assets/uploads/PregnancyGuidelines-Oct11.pdf) for aromatherapists working with pregnant patients. *Salvia sclarea* is listed as an essential oil that may be used during pregnancy.

In certain embodiments, the total concentration of *Salvia* extract in compositions of this disclosure ranges from about 0.001% to about 30% by weight, about 0.001% to about 10% by weight, about 0.001% to about 5% by weight, 0.001% to about 1% by weight, about 0.001% to about 0.5% by weight, about 0.01% to about 5% by weight, about 0.01% to about 2.5% by weight, about 0.01% to about 1% by weight, about 0.01% to about 0.5% by weight, about 0.025% to about 1% by weight, about 0.025% to about 0.5% by weight, or about 0.01% to about 0.2% by weight. In further embodiments, the total concentration of *Salvia* extract is at about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight.

In particular embodiments, compositions of the instant disclosure comprise: (a) xylose at a concentration ranging from about 0.001% to about 10% by weight, and *Salvia* extract at a concentration ranging from about 0.001% to about 30% by weight; (b) xylose at a concentration ranging from about 0.01% to about 5% by weight, and *Salvia* extract at a concentration ranging from about 0.001% to about 30% by weight; (c) xylose at a concentration ranging from about 0.02% to about 1% by weight, and *Salvia* extract at a concentration ranging from about 0.001% to about 30% by weight; (d) xylose at a concentration ranging from about 0.001% to about 10% by weight, and *Salvia* extract at a concentration ranging from about 0.01% to about 5% by weight; (e) xylose at a concentration ranging from about 0.01% to about 5% by weight, and *Salvia* extract at a concentration ranging from about 0.01% to about 5% by weight; (f) xylose at a concentration ranging from about 0.02% to about 1% by weight, and *Salvia* extract at a concentration ranging from about 0.01% to about 5% by weight; (g) xylose at a concentration ranging from about 0.001% to about 10% by weight, and *Salvia* extract at a concentration ranging from about 0.01% to about 1% by weight; (h) xylose at a concentration ranging from about 0.01% to about 5% by weight, and *Salvia* extract at a concentration ranging from about 0.01% to about 1% by weight; or (i) xylose at a concentration ranging from about 0.02% to about 1% by weight, and *Salvia* extract at a concentration ranging from about 0.01% to about 1% by weight.

The pH of the compositions disclosed herein range from about 3.0 to about 8.0, depending on the stage of hormone cycle and/or stage of life of the female subject as described herein. In certain embodiments, the female subject is human.

The compositions of the present disclosure may further comprise a non-irritating viscosity increasing agent. Viscosity is a property of liquids that is closely related to the resistance to flow. It may be defined by Couette flow, which is the laminar flow of a viscous fluid in the space between two parallel plates, one of which is moving relative to the other. The flow is driven by virtue of viscous drag force acting on the fluid and the applied pressure gradient parallel to the plates.

In certain embodiments, compositions of the instant disclosure are formulated to have rheological properties best suited for the target tissue (i.e., female lower reproductive tract) and to mimic the properties of normally occurring fluids and mucus surrounding exposed LRT cells. For example, compositions formulated as gels applied to mucous membranes may be designed to have viscosity values consistent with or similar to normal mucus, and exhibiting non-Newtonian, shear-thinning (pseudoplastic) flow properties.

Standardized methodology for quantitative comparisons of over-the-counter vaginal products based features such as, stickiness, ropiness, peaking, rubberiness, thickness, smoothness, and slipperiness, are known in the art (Mahan et al., Contraception, 2011, 84:184-193).

For compositions applied to skin (such as the vulva) or inside the vagina, a non-irritating viscosity increasing agent can be added in an amount that allows the composition to spread easily to form a thin layer when minimal physical pressure is applied, and to have adequate viscosity and shear-thinning properties so that the composition does not "run" off or out of the lower reproductive tract tissue upon topical application. Mucoadhesive formulations that are retained at the vaginal mucosal surface for prolonged biological activity are known in the art (reviewed by Khutoryanskiy, *Macromol. Biosci.* 11:748, 2011; Brooks, *Front. Chem.* 3:65, 2015)

The rheological characteristics of compositions once present on the tissue of interest are complex and can be influenced by a variety of factors, including the formulation of the composition, temperature, pH, salt concentration, and ion concentration, as well as the presence and physical properties of the physiological secretions (e.g., mucus, semen, blood, etc.).

In any of the aforementioned embodiments, the composition further comprises a non-irritating viscosity increasing agent at a concentration of about 0.001% to about 45%, about 0.001% to about 30%, about 0.001% to about 25%, about 0.001% to about 20%, about 0.001% to about 15%, about 0.001% to about 10%, about 0.001% to about 5%, about 0.001% to about 3%, about 0.01% to about 30%, about 0.01% to about 25%, about 0.01% to about 20%, about 0.01% to about 15%, about 0.01% to about 10%, about 0.01% to about 5%, about 0.01% to about 3%, about 0.1% to about 30%, about 0.1% to about 25%, about 0.1% to about 20%, about 0.1% to about 20%, about 0.1% to about 15%, about 0.1% to about 10%, about 0.1% to about 5%, about 0.1% to about 3%, about 0.5% to about 30%, about 0.5% to about 25%, about 0.5% to about 20%, about 0.5% to about 15%, about 0.5% to about 10%, about 0.5% to about 5%, about 0.5% to about 3%, about 1% to about 30%, about 1% to about 25%, about 1% to about 20% about 1% to about 15%, about 1% to about 10%, about 1% to about 5%, about 1% to about 3%, about 5% to about 30%, about 5% to about 25%, about 5% to about 20%, about 5% to about 15%, or about 5% to about 10% by weight.

Non-irritating viscosity-increasing agents for use in the compositions of the present disclosure are used in concentrations that do not cause cell or vaginal microbiota toxicity, sperm toxicity, oocyte toxicity, embryo toxicity, epithelial cell damage, cytokine release, or mucus function disruption. In certain embodiments, a non-irritating viscosity-increasing agent is a carbomer, polyoxazoline, cellulose, cellulose ether, or a combination thereof. A cellulose ether may be methylcellulose, ethylcellulose, ethyl methyl cellulose, hydroxyethyl cellulose, hydroxypropyl cellulose, hydroxyethyl methyl cellulose, hyroxypropyl methyl cellulose (hypromellose), ethyl hydroxyethyl cellulose, carboxymethyl cellulose, or any combination thereof. In particular embodiments, a non-irritating viscosity-increasing agent is selected from cetyl hydroxyethylcellulose, carbomer homopolymer type A, carbomer homopolymer type B, carbomer homopolymer type C, hydroxypropyl methyl cellulose (HPMC or hypromellose), carbomer homopolymer/hypromellose, hydroxyethyl cellulose, hydrophobically-modified hydroxyethyl cellulose, hydroxypropyl cellulose, carboxymethyl cellulose, ethylcellulose, ethyl methyl cellulose, hydroxyethyl methyl cellulose, hydroxyethyl methyl cellulose, ethyl hydroxyethyl cellulose, methylcellulose, guar gum, polyacrylate, acrylate copolymer, acrylates crosspolymer-4, acrylates/$C_{10-30}$ alkyl acrylate crosspolymer, carbomer interpolymer Type A, carbomer interpolymer Type B, carbomer copolymer Type A, carbomer copolymer Type B, polycarbophil, polyvinyl alcohol, polyvinylpyrrolidone, polyoxazoline, or any combination thereof.

In further embodiments, polyoxazoline is a poly(2-oxazoline), for example, a poly(2-alkyl-2-oxazoline) or poly(2-aryl-2-oxazoline). In some embodiments, the poly(2-alkyl-2-oxazoline) is poly(2-methyl-2-oxazoline), poly(2-ethyl-2-oxazoline), poly(2-isopropyl-2-oxazoline), or any combination thereof. In particular embodiments, the poly(2-aryl-2-oxazoline) is poly(2-phenyl-2-oxazoline). Polyoxazolines, such as poly(2-ethyl-2-oxazoline) (PetOx) and related chemicals, offer high levels of biocompatibility, as shown in mucosal irritation studies. These polymers do not decompose under physiological conditions, so no oxidative triggering products are produced (Van Kuringen et al., *Macromol. Biosci.* 12:1114, 2012).

In certain embodiments, a non-irritating viscosity-increasing agent comprises cellulose ether and a carbomer. In some embodiments, the cellulose ether is methylcellulose, ethylcellulose, ethyl methyl cellulose, hydroxyethyl cellulose, hydroxypropyl cellulose, hydroxyethyl methyl cellulose, hyroxypropyl methyl cellulose (hypromellose), ethyl hydroxyethyl cellulose, carboxymethyl cellulose, or any combination thereof. In further embodiments where hydration of vaginal mucosa and secretions are desired, the ratio of cellulose ether (e.g., hypromellose) to carbomer in the composition ranges from about 1:1 to about 8:1, from about 2:1 to about 8:1, or from about 2.5:1 to about 6.5:1. In further embodiments where muco-adherence and product retention in the vagina are desired, the ratio of cellulose ether (e.g., hypromellose) to carbomer in the composition is from about 1:1 to 1:5 or from about 1:2 to about 1:4. In a specific embodiment, the ratio of cellulose ether (e.g., hypromellose) to carbomer in the composition is about 1:2, 2.6:1, 3.3:1, or about 6.2:1.

The tissue muco-adhesion properties, and consequently residence-time on the LRT tissue, of the compositions disclosed herein may vary depending on its intended use. For example, if a composition is formulated to adhere to the vaginal mucosa for several hours, for 24 hours, or for days, a suitable non-irritating viscosity-increasing agent may be used that allows for muco-adhesion for that period of time.

In some embodiments, compositions of the present disclosure have a thicker viscosity for muco-adhesion and balancing of pH, or delivery of drugs over a longer time frame. In other embodiments, compositions of the present disclosure have a lower viscosity for maximal function. For example, lower viscosity compositions provide increased comfort for hydrating formulations, decreased friction during sexual intercourse for lubricating formulations, or rehydration of vaginal secretions and cervical mucus granules for fertility enhancing formulations.

Methods of measuring viscosity of non-Newtonian fluids are known in the art and include rotational rheometry techniques. Other techniques for measuring viscosity are the rolling ball viscometer method (Hubbard and Brown, Ind. Eng. Chem. Anal. Ed. 15: 212-218, 1943) and the capillary viscometry method.

In certain embodiments, the viscosity of the compositions of the present disclosure is about 5 centipoise (cps) to about 750,000 cps, about 500 cps to about 600,000 cps, about 1,500 cps to about 600,000 cps, about 5,000 to about 500,000 cps, or about 10,000 to about 100,000. In some embodiments, the viscosity of the compositions of the present disclosure is about 50 cps to about 5,000 cps, about 1,000 cps to about 15,000 cps, about 10,000 cps to about 75,000 cps, about 50,000 cps to about 200,000 cps, or about 100,000 cps to about 600,000 cps.

Compositions of the present disclosure may further comprise a solvent. A solvent may be an aqueous solvent, a hydrophobic solvent, or a combination thereof. An aqueous solvent may be water. The hydrophobic solvent may be pharmaceutical grade mineral oil or pure, non-oxidized oils made from the plants of: rose, raspberry, apricot, jojoba, olive, corn, cottonseed, peanut, soybean, sesame, or a combination thereof. If oils are used as a solvent in the present composition, it is desirable that the oils are non-oxidized, as many oils have oxidation products, including peroxide, that can cause irritation and immune stimulation in the female LRT. In some embodiments, the solvent is water. The solvent may be at a concentration ranging from about 50% to about 98%, about 60% to about 98%, about 65% to about 98%, about 70% to about 98%, about 75% to about 98%, about 80% to about 98%, about 85% to about 98%, about 90% to about 98%, or about 95% to about 98% by weight in the composition.

In certain embodiments, compositions of the present disclosure may further comprise a buffering agent. A buffering agent contains an acidic species to neutralize hydroxide (OH) ions and a basic species to neutralize hydrogen ($H^+$) ions. However, the acidic and basic species of the buffering agent should not consume each other through a neutralization reaction. The buffering agent can be a weak acid and a salt of the weak acid or a weak base and a salt of the weak base. Thus, the buffering agent can include a weak acid-base conjugate pair or weak base-acid conjugate pair. In certain embodiments, the buffering agent is selected such that the buffering agent's acid form has a pKa the same as or close to the desired pH of the composition or a pH within the desired range of pH values. The total amount of the buffering agent (e.g., conjugate acid-base pair) is selected such that the pH of the composition is maintained at the desired pH or range of pH values. The buffering capacity is the amount of acid or base the buffer can neutralize before the pH of the composition begins to change to an appreciable degree. Thus, the greater the amount of the buffering agent, the more resistant the pH of the composition is to change. In certain embodiments, a buffering agent comprises a monocarboxylate, a dicarboxylate, a carboxylic acid, or a combination thereof. In some embodiments, a buffering agent may comprise an acetate, borate, citrate, fumarate, lactate, malate, malonate, nitrate, phosphate, propanoate, succinate, tartrate, tromethamine, or any combination thereof. In some embodiments, a buffering agent comprises lactic acid, sodium lactate, sodium phosphate (monobasic, dibasic, or both), potassium phosphate (monobasic, dibasic, or both), sodium citrate, potassium citrate, acetic acid, sodium acetate, citric acid, disodium citrate, trisodium citrate, boric acid/sodium, succinic acid, sodium succinate, disodium succinate, tartaric acid, sodium tartarate, sodium ascorbate, ascorbic acid, tromethamine (Tris), or any combination thereof. In further embodiments, a buffering agent comprises sodium lactate and lactic acid, sodium phosphate and potassium phosphate, sodium phosphate and potassium citrate, sodium phosphate, sodium citrate, or ascorbic acid and sodium ascorbate.

In certain embodiments, a buffering agent may be at a concentration from about 0.05% to about 4% by weight, about 0.1% to about 3% by weight, 0.25% to about 2% by weight, or about 0.5% to about 1% by weight in the composition. For those buffering agent acids that comprise monobasic, dibasic, or tribasic forms (e.g., potassium phosphate, sodium phosphate), as used herein, general reference to the acid includes the monobasic, dibasic, and tribasic forms. The amount of the acid means the total amount of any monobasic, dibasic, and tribasic acid forms present. For example, a composition comprising 1% sodium phosphate by weight may comprise monobasic sodium phosphate and dibasic sodium phosphate totaling 1%.

Topical compositions of the present disclosure are formulated at a pH equivalent to the healthy physiologic pH for the LRT tissue to which it is administered and lifecycle stage of the female subject, or for the therapeutic goals of the composition. The buffer agent selected will have a buffering capacity adequate to maintain pH within the healthy physiologic range for the target LRT tissue during its time of residence on the tissue, or to achieve the therapeutic goals of the composition. In certain embodiments, the buffer capacity of the composition is sufficient to resist adjustment by fluid and to maintain the target pH for an appreciable period of time.

In certain embodiments, a composition may simultaneously come into contact with two tissues or cell types that differ in pH (e.g., vaginal mucosa and sperm cells). Special care in formulating may be needed in these circumstances regarding pH and buffer capacity. Some tissues or cells can tolerate less deviation from physiological conditions compared to others (e.g., sperm cells versus vaginal mucosal cells).

In certain embodiments, a composition of this disclosure may further contain an active ingredient (e.g., drug). The pH of the drug containing composition may be adjusted to maintain stability of the active ingredient. In certain embodiments, the buffering capacity of a composition is adequate for drug stability and also matches the overall pH of the target tissue or therapeutic goals of the composition.

In certain embodiments, compositions of the present disclosure further comprise a pH modifying agent. The pH modifying agent may comprise an acidifying agent, an alkalinizing agent, or both. In some embodiments, the acidifying agent is acetic acid, citric acid, fumaric acid, hydrochloric acid, lactic acid, malic acid, nitric acid, phosphoric acid, potassium phosphate monobasic, propionic acid, sodium phosphatemonobasic, sulfuric acid, tartaric acid, or any combination thereof. In some embodiments, the alkalinizing agent is ammonia, ammonium carbonate, diethanolamine, monoethanolamine, potassium hydroxide, potassium phosphate dibasic, sodium bicarbonate, sodium borate, sodium carbonate, sodium hydroxide, sodium lactate, sodium phosphate dibasic, trolamine, or any combination thereof.

In certain embodiments, a pH modifying agent may be at a concentration ranging from about 0.001% to about 2%, from about 0.005% to about 0.75%, from about 0.01% to about 1%, from about 0.01% to about 0.5%, or from about 0.02% to about 0.4% by weight of the composition.

The pH range of the compositions of the present disclosure is from about 3.0 to about 8.0, depending on the physiologic stage of the woman and the intended use of the product. In certain embodiments, the pH range of the composition is about 3.5 to about 5.5 (e.g., for a reproductive aged female), about 4.5 to about 6.8 (e.g., for a menopausal female), about 4.5 to about 6.5 (e.g., for a pregnant female), or about 6.8 to about 7.8 (e.g., for a reproductive aged female during ovulatory phase). In certain embodiments, the pH range of a composition may be broad enough to be targeted to female subjects in different life/cycle stages. For example, a composition may have a pH range of about 3.5 to about 6.8 and be used in a reproductive aged, non-ovulating female subject, a menopausal female subject, and a pregnant female subject.

In certain embodiments, compositions of the present disclosure are sterile and preservative-free. In other embodiments, sterile, preservative-free compositions are in a single-use or unit-dose format.

In other embodiments, compositions of the present disclosure optionally comprise a preservative. In particular embodiments, a preservative is a paraben-free preservative. Parabens are a series of parahydroxybenzoates or esters of parahydroxybenzoic acid and are known to cause cytokine release and irritation and have been linked to several types of cancer. Examples of parabens include methylparaben, ethylparaben, propylparaben, butylparaben, heptylparaben, isobutylparaben, isopropylparaben, benzylparaben, and their sodium salts.

Exemplary paraben-free preservatives include phenethyl alcohol, caprylyl glycol, phenoxyethanol, a sorbate, potassium sorbate, sodium sorbate, sorbic acid, sodium benzoate, benzoic acid, acemannan, oleuropein, carvacrol, cranberry extract, gluconolactone, green tea extract, *Helianthus annuus* seed oil, *Lactobacillus* ferment, *Usnea barbata* extract, polyaminopropyl biguanide, polyglyceryl-3 palmitate, polyglyceryl-6 caprylate, pomegranate extract, *Populus tremuloides* bark extract, resveratrol, *Rosmarinus officinalis* leaf extract, benzyl alcohol, or any combination thereof. In some embodiments, compositions of the present disclosure include a preservative in combination with one or more paraben-free preservative, such as phenethyl alcohol and caprylyl glycol. In particular embodiments, a paraben-free preservative comprises phenethyl alcohol in an amount of 56%-60% and caprylyl glycol in an amount of 40%-44% (e.g., Tristat Stabil).

In certain embodiments, compositions of this disclosure further comprise a preservative at a concentration of about 0.005% to about 10% by weight, about 0.005% to about 5%, about 0.005% to about 2.5%, about 0.005% to about 1%, about 0.005% to about 0.5%, about 0.005% to about 0.1%, about 0.01% to about 10%, about 0.01% to about 5%, about 0.01% to about 2.5%, about 0.01% to about 1%, about 0.01% to about 0.5%, about 0.01% to about 0.1%, about 0.1% to about to about 10%, about 0.1% to about 5%, about 0.1% to about 2.5%, about 0.1% to about 1%, about 0.1% to about 0.5%, about 1% to about 10%, about 1% to about 5%, or about 1% to about 2.5% by weight.

In further embodiments, compositions of the present disclosure further comprise an osmolality adjuster or osmolality adjusting agent. Osmolality is a measure of minimum pressure which needs to be applied to a solution to prevent the inward flow of water across a semipermeable membrane and is expressed in milliosmoles per kilogram of solvent (mOsmol/kg). The osmotic pressure of a solution depends on the number of particles in solution. Osmolality of a solution may be measured by measuring freezing point depression or vapor pressure lowering.

In certain embodiments, the compositions disclosed herein are both iso-osmotic and isotonic with respect to the targeted lower reproductive tract tissues and the mucus they secrete. Compositions having physiologic osmolality maintain LRT cell structure and function. Exposure of LRT cells to high osmolality compositions will cause a net movement of water out of the cells and irreversible ultrastructural damage. Exposure of LRT tract cells to low osmolality compositions will cause a net movement of water into the cells and may lead to cell bursting/death. Iso-osmotic compositions, having the same osmolality as that within LRT cells or LRT mucus secretions, are safe for use in the LRT.

Tonicity is a measure of the effective osmotic pressure gradient (as defined by the water potential of two solutions) of two solutions separated by a semipermeable membrane. Tonicity is commonly used when describing the response of cells immersed in an external solution. In other words, tonicity is the relative concentration of solutions that determine the direction and extent of diffusion. Body fluids normally have an osmotic pressure that corresponds to that of a 0.9% solution of sodium chloride. A composition (e.g., solution or gel) is considered isotonic when its tonicity is about equal to that of a 0.9% sodium chloride solution (i.e., 290 mOsm). A composition is isotonic with a body fluid solution when the magnitude of the salts are equal between the composition and the physiologic solution. Tonicity equilibrium is reached in physiologic solutions by water moving across the membranes, but the salts staying in their solution of origin. A solution is isotonic with a living cell if there is no net gain or loss of water by the cell, or other changes in the cell, when it is in contact with that solution.

Hypertonic solutions cause a net movement of water out of the cells (as the water moves to create equilibrium with the high salt levels outside of the cell). This dehydration of the cell is concentration dependent and leads to osmotic stress which can increase reactive oxygen species, cause cytoskeletal rearrangement, and damage DNA and mitochondrial function within minutes of exposure. Hypotonic solutions cause a net flow of water into the cell and cause cell bursting and death. In order to maximize homeostasis and healthy function of sperm and lower reproductive tract mucosal cells, the compositions of the present disclosure are isotonic.

The term isotonic, meaning equal tone, is commonly used interchangeably with the term iso-osmotic. However, iso-osmotic actually is a more broad term that compares the osmotic pressure of two liquids, wherein the small particles present need not be salts. The particles providing osmotic pressure can be membrane permeable compounds such as glycerol or propylene glycol. In this case, water and the osmotic particles both can move across the membranes. The osmotic particles do not move in response to highly orchestrated cell transport concentration gradients but primarily through diffusion. Therefore, these particles end up inside living cells during physiologic exposure. Often such particles cause damage inside the cell they penetrate. For example, a solution containing glycerol that is iso-osmotic with semen, has the same osmolarity as semen, but the glycerol can penetrate into the sperm cell and damage its function. Osmolarity takes into account the total concentration of penetrating solutes and non-penetrating solutes, whereas tonicity takes into account the total concentration of only non-penetrating solutes. Isotonicity infers a sense of physiological compatibility whereas iso-osmotic does not require this.

In certain embodiments, an osmolality adjuster used in the compositions disclosed herein is an electrolyte, mono- or disaccharide, inorganic salt (e.g., sodium chloride, calcium chloride, sodium sulfate, magnesium chloride), or a combination thereof. In some embodiments, an osmolality adjuster is glucose, sucrose, sodium chloride, potassium chloride, calcium chloride, sodium sulfate, magnesium chloride, dextrose, mannitol, or any combination thereof.

In certain embodiments, the osmolality range of the compositions disclosed herein is about 200 mOsm/kg to about 600 mOsm/kg, about 240 mOsm/kg to about 400 mOsm/kg, or about 260 mOsm/kg to about 380 mOsm/kg.

In certain embodiments, compositions disclosed herein further comprise a surfactant. In some embodiments, the surfactant is cetyl hydroxyethylcellulose, hydrophobically modified hydroxyethyl cellulose, poloxamer, polyoxyethylene glycol alkyl ether, polyoxypropylene glycol alkyl ether, glucoside alkyl ether, polyoxyethylene glycol alkylphenol ether, glycerol alkyl ester, polysorbate, cocamide monoethanolamine (MEA), cocamide diethanolamine (DEA), dodecyldimethylamine oxide, or any combination thereof. The surfactant may be present at a concentration of about 0.01% to about 20%, about 0.01% to about 15%, about 0.01% to about 10%, about 0.01% to about 10%, about 0.01% to about 5%, about 0.01% to about 2.5%, about 0.01% to about 1%, about 0.01% to about 0.5%, about 0.01% to about 0.1%, about 0.1% to about 20%, about 0.1% to about 10%, about 0.1% to about 5%, about 0.1% to about 2.5%, 0.1% to about 1%, or about 0.1% to about 0.7%, about 1% to about 20%, about 1% to about 10%, about 1% to about 15%, about 1% to about 10%, about 1% to about 5%, or about 1% to about 2.5% by weight.

In certain embodiments, the compositions disclosed herein possess an endotoxin level of less than or equal to 20 EU/ml, 15 EU/ml, 10 EU/ml, 7.5 EU/ml, 5 EU/ml, 2.5 EU/ml, 1 EU/ml, 0.75 EU/ml, 0.5 EU/ml, 0.25 EU/ml, or 0.1 EU/ml. Bacterial endotoxins, found in the outer membrane of gram-negative bacteria, are members of a class of phospholipids called lipopolysaccharides (LPS). LPS and endotoxins are powerful innate immune system stimulants. Even picogram concentrations of LPS can stimulate chronic inflammatory conditions leading to systemic and localized disease.

Bacterial endotoxin levels can be quantified using methods known in the art, including the Limulus Amebocyte Lysate (LAL) assays. This assay is based in the biology of the horseshoe crab (*Limulous*). These animals produce LAL enzymes in blood cells (amoebocytes) to bind and inactivate endotoxin from invading bacteria. The inactivation of endotoxin by LAL forms a clot. The LAL test exploits the clotting action of this enzyme, by adding a LAL reagent to the tested product, and assaying for clot formation. LAL test methodologies include gel-clot techniques, photometric techniques including kinetic turbidimetric methods, and chromogenic methods.

Compositions of the present disclosure may optionally comprise a humectant, an emollient, or both. In some embodiments, the humectant is a sugar alcohol, such as glycerin, sorbitol, xylitol, mannitol; hexylene glycol, butylene glycol, propylene glycol glyceryl triacetate, an alpha hydroxyl acid (e.g., lactic acid), galactoarabinan, or a combination thereof. In some embodiments, the emollient is pharmaceutical grade mineral oil, a purified, non-oxidized plant oil (e.g., rose, raspberry, corn, cottonseed, peanut, soybean, sesame, apricot, jojoba, olive), cetostearyl alcohol, glyceryl stearate, acemannan, or a combination thereof.

The function of each of the excipients is not mutually exclusive within the context of the compositions of the present disclosure. For example, cetyl hydroxyethylcellulose or hydroxyethyl cellulose may be used as a non-irritating viscosity increasing agent or a surfactant. In yet another example, sodium lactate or lactic acid may be used as a buffering agent or a pH modifier. In yet another example, acemannan may be used as a paraben-free preservative, an emollient, or a prebiotic.

In certain embodiments, the compositions disclosed herein further comprise an additional therapeutic agent. For example, a therapeutic agent may be included in the composition to improve cell or tissue function or to treat an underlying disease or disorder. In another example, a therapeutic agent may be an anti-microbial agent (e.g., an antibiotic, anti-fungal agent, anti-viral agent, or any combination thereof). In certain embodiments, an anti-microbial agent is an anti-fungal agent selected from butoconazole nitrate, clotrimazole, miconazole nitrate, terconazole, tioconazole, econazole nitrate, efinaconazole, ketoconazole, luliconazole, naftifine hydrochloride, oxiconazole nitrate, sertaconazole nitrate, sulconazole nitrate, tavaborole, terbinafine, acyclovir, tenovir, zidovudine, stavudine, metronidazole, or a combination thereof.

Other examples of therapeutic agents include hormones (e.g., estradiol, estriol, estropipate, testosterone, progesterone, DHEA or a combination thereof) for use in treating genitourinary syndrome of menopause (GSM), agents for treating or preventing a hormone imbalance or infertility (e.g., progesterone, estrogen, testosterone), contraceptives (e.g., impairs sperm function, thickens cervical mucus, or both), growth factors (e.g., vascular endothelial growth factor), vasodilators (e.g., L-arginine, niacin, nicotinamide, alprostadil, phosphodiesterase inhibitor).

In certain embodiments, the compositions disclosed herein further comprise factors that maintain, improve, or enhance VMB (e.g., Lactobacilli) function and health, such as amylase, glycogen, D-lactic acid, L-lactic acid, or a combination thereof.

In certain embodiments, the compositions disclosed herein further comprise at least one prebiotic. A prebiotic refers to non-digestible plant fiber that stimulates the growth or activity of one or more VMB species. Examples of prebiotics that can be used include acemannan and galactoarabinan (see, Al-Ghazzewi and Tester, 2016, J. Appl. Microbiol. 10.1111/jam.13054 (e-publication ahead of print); Gullon et al., 2015, Food Funct. 6:525-531; http://www.fda.gov/ucm/groups/fdagov-public/@fdagov-foods-gen/documents/document/ucm266729.pdf).

In certain embodiments, the compositions disclosed herein further comprise at least one vaginal probiotic bacterial species or strain (e.g., belonging to the genus *Lactobacillus*). As used herein, "vaginal probiotic bacteria" refer to live bacteria, which when administered in adequate amounts to the vagina confer a health benefit to the host. A In certain embodiments, the probiotic bacterial species or strain is one having the ability to colonize the human vagina. The adhesion of lactobacilli to the uroepithelium varies among species and strains, as shown by in vitro studies (Reid et al., 1987, J. Urol. 138:330-335), and may be mediated by glycoprotein and carbohydrate adhesins binding to glycolipid receptors (Boris et al., 1998, Infection and Immunity 66:1985-1989). In some embodiments, a vaginal probiotic species is a species that is part of the VMB. In a specific embodiment, a vaginal probiotic species is selected from *Lactobacillus fermentum, Lactobacillus acidophilus, Lactobacillus jensenii, Lactobacillus gasseri, Lactobacillus iners, Lactobacillus crispatus, Lactobacillus plantarum, Lactobacillus fermentum, Lactobacillus brevis, Lactobacillus casei, Lactobacillus delbrueckii, Lactobacillus vaginalis, Lactobacillus salivarius*, or any combination thereof. In some embodiments, a vaginal probiotic bacterial species or strain is encapsulated or coated. Compositions containing a vaginal probiotic species preferably include a paraben-free preservative.

A vaginal probiotic bacterial species or strain may be administered in an amount of about $10^4$ to about $10^{12}$ colony forming units (CFU), or about $10^5$ to about $10^{11}$ CFU, or about $10^6$ to about $10^{10}$ CFU, or about $10^7$ to about $10^9$ CFU per dose. In some embodiments, a vaginal probiotic bacterial species or strain may be administered in an amount of about 4 million to about 400 million colony forming units (CFU) per dose.

A vaginal probiotic bacterial species or strain may be included in the compositions disclosed herein for treatment and/or prophylaxis of bacterial vaginosis, viral vaginosis, yeast vaginitis, infections in the vagina, sexually transmitted diseases, such as HIV and chlamydia infection, infections endangering the fetus in pregnant women, preterm labour and urinary tract infection.

In certain embodiments, the compositions of the present disclosure do not comprise polyethylene glycol (PEG). Because of its widespread use, antibodies to PEG are seen in 25% of patients. PEG is prone to oxidative degradation that can further trigger an immune response in patients (De la Rosa, Mater Sci. Mater Med. 25:1211, 2014). PEG triggers high levels of interleukin secretions in cervical cells (Gali et al., Antimicrob. Agents Chemother. 54:5105, 2010).

In certain embodiments, the compositions of the present disclosure do not comprise a glycosaminoglycan (GAG), for example hyaluronic acid. Although GAGs naturally exist in the vaginal ecosystem, use of purified GAGs for treating vaginal dryness may cause a disruption in the LRT homeostasis and function (Chen et al., J. Sex. Med. 10:1575, 2013). Hyaluronic acid, a common ingredient in personal lubricants, has been shown to cause vaginal epithelial cells to release changed antimicrobial peptides via TLR signaling. Elevated hyaluronan levels were associated with vaginal itching and burning or itching and discharge in women with vulvovaginal candidiasis and may contribute to symptoms (Lev-Sagie et al., 2009, Am. J. Obstet. Gynecol. 201:206).

In certain embodiments, compositions of the present disclosure do not comprise glycerol. Glycerol has a direct toxic effect on sperm cells damaging their cell membranes and metabolism as it penetrates the cell (McLaughlin et al., 1992, J. Reprod. Fertil. 95:749-54). Glycerol also causes a two-fold increase in interleukin production from cervical cells at a 0.5% concentration and a 5-fold increase in interleukin at a 5% concentration. This concentration range is common for many vaginal products on the consumer shelf.

In certain embodiments, compositions of the present disclosure do not comprise an oil other than Salvia extract oil unless the oil is pharmaceutical grade or free from significant levels of oxidation products. An oil may be a petroleum oil, e.g., mineral oil, a plant oil (e.g., almond oil), or an essential oil. Photo-oxidation and auto-oxidation of oils occurs routinely. Oxidation changes in oils can have a profound impact on biological function (Morbeck et al., 2010, Fertil. Steril. 94:2747-52). While peroxide levels of 10 meq/kg in oils are considered safe for consumption, small concentrations (<1 meq/kg) causes reductions in in vitro sperm motility and embryo development. An 8-fold increase in yeast infection rates has been attributed to non-pharmaceutical grade mineral oil use in the vaginal ecosystem. Pharmaceutical grade mineral oil ("mineral oil USP") is mineral oil that been washed with pharmaceutical grade, highly purified water and tested for peroxide value (POV) below 0.1 mEq.

One concern relating to the safety assessment of botanical ingredients in personal care products is their contamination with heavy metals. If heavy metals are present in topically applied products, local and systemic toxic and inflammatory effects may result. Heavy metals when applied to epithelial surfaces, such as the female lower reproductive tract, result in the generation of highly reactive oxygen free radicals, such as hydroxyl radical, thus stimulating oxidative damage to the tissues. Generation of highly reactive oxygen free radicals may also accelerate degradation of the compositions of the present disclosure. If absorbed systemically in sufficient quantities, some heavy metals may have toxic effects on cardiovascular, pulmonary, urinary, gastrointestinal, and neurological systems.

Heavy metals include cadmium, lead, inorganic arsenic, inorganic mercury, iridium, osmium, palladium, platinum, rhodium, ruthenium, chromium, molybdenum, nickel, vanadium, and copper.

The toxicity of an elemental impurity is related to its extent of exposure (bioavailability). The extent of exposure has been determined for each of the elemental impurities of interest. These limits are based on chronic exposure. Permissible daily exposure (PDE) described in Table 1 below would apply to a composition of this disclosure to be applied to the skin or mucosa.

The values provided in Table 1 represent concentration limits for components (drug substances and excipients) of topical products applied at a maximum daily amount of <10 g/day.

TABLE 1

Elemental Impurities for Drug Products

| Element | Concentration Limits (mg/g) for Mucosal or Topical Product with a Maximum Daily Dose of ≤ 10 g/day |
|---|---|
| Cadmium | 2.5 |
| Lead | 0.5 |
| Inorganic arsenic | 0.15 |
| Inorganic mercury | 1.5 |
| Iridium | 10 |
| Osmium | 10 |
| Palladium | 10 |
| Platinum | 10 |
| Rhodium | 10 |
| Ruthenium | 10 |
| Molybdenum | 10 |
| Nickel | 50 |
| Vanadium | 10 |
| Copper | 100 | a PDE = Permissible daily exposure based on a 50-kg person.

Methods of detecting elemental impurities are known in the art and include inductively coupled plasma-atomic (optical) emission spectroscopy (ICP-AES or ICP-OES) or ICP mass spectrometry.

The presence of certain microorganisms in non-sterile compositions may have the potential to reduce or even inactivate the therapeutic activity of a composition and may adversely affect the health of the patient. Good Manufacturing Practice may be used to ensure a low bioburden of finished dosage forms.

In certain embodiments, compositions disclosed herein adhere to acceptance criteria for nonsterile pharmaceutical products for topical use as set forth in Table 2, which are based upon the total aerobic microbial count (TAMC) and the total combined yeasts and molds count (TYMC).

TABLE 2

Acceptance Criteria for Microbiological Quality

| Route of Administration | Total Aerobic Microbial Count (cfu/g or cfu/mL) | Total Combined Yeasts/Molds Count (cfu/g or cfu/mL) | Specified Microorganism(s) |
|---|---|---|---|
| Vaginal | 100 | 10 | Absence of Pseudomonas aeruginosa (1 g or 1 mL) |

TABLE 2-continued

Acceptance Criteria for Microbiological Quality

| Route of Administration | Total Aerobic Microbial Count (cfu/g or cfu/mL) | Total Combined Yeasts/Molds Count (cfu/g or cfu/mL) | Specified Microorganism(s) |
|---|---|---|---|
| | | | Absence of *Staphylococcus aureus* (1 g or 1 mL) Absence of *Candida albicans* (1 g or 1 mL) |

Tests for determining whether a composition complies with a specification for microbiological quality of a non-sterile composition are known in the art (e.g., United States Pharmacopeia and The National Formulary (USP-NF), Chapter 61 and Chapter 62). In certain embodiments, compositions disclosed herein adhere to acceptance criteria for sterile pharmaceutical products. Sterilization of the composition may be achieved by methods known in the art, including heat (e.g., steam under pressure, filtration high pressure, irradiation (non-ionizing and ionizing), and chemicals (e.g., ethylene oxide, nitrogen dioxide, formaldehyde). Tests for determining whether a composition complies with a specification for microbiological quality for a sterile composition are known in the art (e.g., United States Pharmacopeia and The National Formulary (USP-NF), Chapter 71). In some embodiments, a sterilization procedure for a composition is validated to assure sterility of the composition and that no adverse change has occurred in the composition as a result of the sterilization procedure. For example, a decrease in viscosity may occur in a composition following steam sterilization. A formula for a composition may be modified to accommodate post-sterilization changes in viscosity to retain or achieve desired composition viscosity.

The compositions disclosed herein may be formulated as a semi-solid, gel, ointment, liquid, lotion, jelly, film, suspension, emulsion, mucilage, foam, cream, paste, or aerosol. In certain embodiments, the compositions are formulated as a gel. The compositions may be administered topically to the female lower reproductive tract (e.g., to the vulva or into the vagina), to a sex toy that is to be inserted into the vagina of a female subject, to the male penis prior to sexual intercourse or manual semen collection, or used to lubricate medical devices or instruments in the context of gynecological procedures or assisted reproduction techniques. The compositions of the present disclosure are formulated so as to allow the xylose, *Salvia* extract, and any other therapeutic agent contained therein to be bioavailable upon administration of the composition to the subject.

The compositions of the present disclosure may be administered to a subject as a single dosage unit or the compositions may be administered as a plurality of dosage units. For example, the compositions may be sterilized, and packaged preservative-free in single-use, plastic laminated pouches or plastic tubes of dimensions selected to provide for routine, measured dispensing. In one example, a container may have dimensions used to dispense a single dose (e.g., about 4 ml) of the composition (e.g., a gel form) to the lower reproductive tract. In another example, compositions may comprise a paraben-free preservative and packaged in a multi-use container used to dispense multiple doses of the composition.

In certain embodiments, compositions of this disclosure may be administered daily (e.g., q.d., b.i.d., t.i.d., q.i.d), weekly, monthly, or on an as needed basis. In some embodiments, compositions of the present disclosure are administered in an amount of about 0.5 ml to about 100 ml, about 1 ml to about 75 ml, about 2.5 ml to about 50 ml, about 5 ml to about 40 ml, about 10 ml to about 30 ml, about 15 ml to about 25 ml, about 0.5 ml to about 50 ml, about 0.5 ml to about 40 ml, about 0.5 ml to about 30 ml, about 0.5 ml to about 20 ml, about 0.5 ml to about 10 ml, about 0.5 ml to about 5 ml, about 1 ml to about 50 ml, about 1 ml to about 40 ml, about 1 ml to about 30 ml, about 1 ml to about 20 ml, about 1 ml to about 10 ml, or about 1 ml to about 5 ml. In some embodiments, compositions of the present disclosure are administered in an amount of about 0.25 ml, 0.5 ml, 0.75 ml, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, or 100 ml.

Any of the compositions disclosed herein may be used in methods for promoting or enhancing vaginal ecosystem homeostasis of the lower reproductive tract, comprising administering a composition according to the present disclosure to the lower reproductive tract of a female subject. Moreover, any of the compositions disclosed herein may be used in methods for increasing hydration of the lower reproductive tract, comprising administering a composition according to the present disclosure to the lower reproductive tract of a female subject.

Furthermore, the compositions disclosed herein may be used as a base composition in a variety of products directed to the female reproductive tract, which can be further modified according to the life stage (e.g., reproductive age, menopause) or menstrual phase (e.g., ovulatory, luteal, pregnant) of the female subject and intended use of the product (e.g., perineal massage, contraceptive, anti-microbial, fertility enhancement, sexual lubricant, vaginal hydration, sexual arousal, vaginal tightening, vaginal freshening, vaginal homeostasis, or drug carrier base). Non-limiting examples of such products follow in further detail.

In yet another aspect, the compositions disclosed herein may be used during sexual intercourse or artificial insemination by application to the male penis prior to or during sexual intercourse or manual collection of sperm, or to condoms (interior, exterior, or both) during sexual intercourse, or to sex toys prior to use. Generally, sperm donors collect semen samples by manual manipulation without the benefit of lubrication because available lubricants and saliva are spermicidal. In certain embodiments, the compositions of the present disclosure are non-toxic to sperm and may maintain, preserve, enhance, or increase sperm survival or function. In certain embodiments, the compositions disclosed herein may be applied directly to the penis, to the hand, coat the interior or exterior of a condom, or be placed in a receptacle for sperm collection such as a vial, tube, baggie, or other collection devices.

In addition, the compositions disclosed herein may be used in various assisted reproductive techniques, diagnostic procedures, and medical procedures. In certain embodiments, the compositions of the present disclosure are non-toxic to oocytes or embryos and may maintain, preserve, enhance, or increase oocyte or embryo survival or function. For example, a composition may be used to coat a speculum during pelvic examinations, a catheter for insertion into a bladder to collect sperm from a retrograde ejaculation, a uterine balloon tamponade, or a vaginal ultrasound probe. A composition may be used to lubricate a catheter, pipette, hand, or other medical device or instrument in the context of a variety of assisted reproduction procedures including egg retrieval, egg freezing, intracytoplasmic sperm injection (ICSI), embryo culture, embryo freezing, embryo thawing, embryo transfer, and artificial insemination. A composition may also be used as a lubricant in diagnostic procedures such as endoscopy, hysteroscopy, sonohysterosalpingogram, contrast radiography (e.g., hysterosalpingogram), or biopsy (e.g., endometrial biopsy). The compositions disclosed herein may be used in any variety of species for sperm collection, sexual intercourse, assisted reproductive techniques, diagnostic or medical procedures, and the like. Such subjects include, but are not limited to, humans, bovine, equine, canine, ovine, avian, feline, porcine, avian, rodent, lagomorph, caprine, primate, and various exotic or rare species (e.g., elephant, lion, rhinoceros). In embodiments where a LRT composition is used in the context of improving fertility, assisted reproductive techniques, or in a female subject that is in the ovulatory phase, the pH range of the composition is matched to the LRT during the ovulatory phase (pH of about 6.8 to about 7.8). In embodiments where a LRT composition is used in a medical or diagnostic context on a female subject who is in a non-ovulatory phase (for reproductive aged woman), in menopause, or pregnant, the pH range of the composition is matched to the LRT to the cycle or life specific phase (pH of about 3.5 to about 5.5, pH of about 4.5 to about 6.8, and pH of about 4.5 to about 6.5, respectively).

(1) Perineal Massage Compositions

In one aspect of the present disclosure, compositions formulated (e.g., in the form of a gel) for use in perineal massage are provided. The practice of perineal massage (PM) widens and relaxes a woman's birth canal during her last month of pregnancy. The perineum includes the back portion of a woman's birth canal (e.g. vagina and vulva). A perineum that can't stretch to let the baby's head through the birth canal will undergo perineal trauma and either tear, or be cut by a doctor in an episiotomy. These perineal tears or cuts require suturing to heal, which can often scar, causing pain after childbirth. This can negatively impact sexual function or lead to incontinence of urine or feces. An intact perineum is one that stretches to let the baby out and doesn't undergo tearing or cutting, and suturing. Studies have shown that women who keep an intact perineum during childbirth have less pain and incontinence and better sexual satisfaction post-partum. Nearly half of women undergoing childbirth will suffer some perineal trauma. Perineal massage in the final month of pregnancy decreases the rates of perineal trauma, episiotomies and postpartum pain.

Perineal massage is a daily manual stretching of the back of the birth canal, starting at 34 weeks of gestation for at least 4 or at least 5 minutes each day. Current recommendations for perineal massage include use of aloe vera gel, almond oil, K-Y® Jelly or Vaseline for the procedure. However, almond oil is known to have high levels of oxidative chemicals, which are potent triggers of the LRT inflammation system. K-Y® Jelly is known to be severely irritating and to cause the death of vaginal microbiota. Aloe vera gels contain high levels of endotoxins and heavy metals, which can cause cell toxicity and inflammation. Vaseline has been shown to cause an 8-fold increase in vaginal yeast infections.

The compositions disclosed herein that are pH matched to the vulvar and vaginal pH of pregnant women (about 4.5 to about 6.5) can be used as a perineal massage composition. In another embodiment, a perineal massage composition may also be used during labor to facilitate delivery of a baby during childbirth. The perineal massage compositions can be formulated as a semi-solid, gel, ointment, liquid, lotion, jelly, film, suspension, emulsion, mucilage, foam, cream, paste, or aerosol.

In certain embodiments, a perineal massage composition is used in a method of reducing perineal trauma during child birth, comprising administering the perineal massage composition to the perineum, vagina, or external genitalia of a pregnant female subject. In some embodiments, the composition is gently massaged into the perineum, vagina, and external genitalia. In some embodiments, the perineal massage gel is administered to the subject beginning at 34-36 weeks of gestation, and may continue daily, every other day, 2-3 times a week, or weekly. The perineal massage may continue for at least 1 minute, at least 2 minutes, at least 3 minutes, at least 4 minutes, or at least 5 minutes at a time. In some embodiments, the perineal massage composition may be administered to the perineum, vagina, or external genitalia of the subject during labor.

(2) Microbicide or Contraceptive Compositions

In another aspect of the present disclosure, compositions that optimize the formation of thick, hostile cervical mucus to decrease sperm and/or pathogen penetration through the vaginal and cervical canal are provided. Over the counter, vaginally administered contraceptives and microbicides contain numerous inactive ingredients that may cause profound mucosal irritation, epithelial toxicity, vaginal microbiota damage, and interleukin secretion. Contraceptive active components and microbicides are de facto cell toxic compounds. Prior development of vaginal drugs has unfortunately coupled such cytotoxic active drugs with highly cytotoxic inactive carrier ingredients. Available commercial vaginal contraceptives include at least three inactive ingredients known to cause significant LRT damage on their own, in addition to the cytotoxic contraceptive active ingredient, nonoxyonol-9. Existing non-oxynol products have been shown to increase STD transmission. The compositions of the present disclosure provide LRT carrier formulas that maximize safety of such products.

The microbicide or contraceptive containing compositions provided herein are matched to the vulvar and vaginal pH of the subject, e.g., for a reproductive aged woman (about 3.5 to about 5.5), an ovulatory phase woman (about 6.8 to about 7.8), or postmenopausal woman (around about 4.5 to about 6.8).

In certain embodiments, the contraceptive compositions may impede sperm function and transport through cervical mucus. In certain embodiments, the microbicide compositions stimulate increased clearance of pathogens and/or lower infection rates after exposure. In some embodiments, the compositions further comprise an additional contraceptive agent or anti-microbial agent (e.g., antibiotic, anti-fungal agent, anti-viral agent, or any combination thereof). A microbicide or contraceptive composition can be formulated as a semi-solid, gel, ointment, liquid, lotion, jelly, film, suspension, emulsion, mucilage, foam, cream, paste, or aerosol. A microbicide or contraceptive composition can be used as a lubricant, contraceptive, anti-microbial, drug carrier base, for vaginal hydration, vaginal freshness, vaginal homeostasis, or any combination thereof.

An exemplary formulation of a contraceptive composition X and % ranges of each component as contemplated in the present disclosure is set forth as follows: 85.248% by weight purified water, 1.0% by weight cetyl hydroxyethylcellulose, 2.0% by weight carbomer, 0.139% by weight lactic acid, 0.683% by weight sodium lactate, 0.232% by weight phenethyl alcohol, 0.168% by weight caprylyl glycol, 0.05% by weight *Salvia sclarea*, 0.15% by weight sodium chloride, 0.05% by weight calcium chloride, 10% by weight *Salvia hispanica*, 0.04% by weight d-Xylose, and 0.1%-1% sodium hydroxide. In certain embodiments, contraceptive composition X is formulated as a gel.

In certain embodiments, lower doses of contraceptive drugs or anti-microbial drugs may be used in the compositions if the base formula of the composition thickens cervical, mucus, impairs sperm function, or impairs microbial penetration of the cervical mucus.

In certain embodiments, the microbicide containing compositions may be used in a method of treating an infection of the lower reproductive tract, comprising administering the microbicide containing composition to the lower reproductive tract of a female subject (e.g., intravaginally, to the vulva).

In certain embodiments, the contraceptive containing compositions may be used in a method of inhibiting conception, comprising administering the contraceptive containing composition intravaginally, to the vulva or penis, to condoms (interior or exterior), or other devices or instruments. In some embodiments, the contraceptive containing composition is administered within 24 hours, 12 hours, 6 hours, 2 hours, 1 hour, 30 minutes, 15 minutes, 5 minutes, just prior to, or during sexual intercourse.

(3) Fertility Compositions

In another aspect of the present disclosure, fertility compositions are provided. During the ovulatory phase of the menstrual cycle, vaginally applied compositions may be used to support and enhance penetration of the cervical mucus by sperm. Current commercial vaginal fertility products contain ingredients that trigger interleukin production and epithelial disruption of the vaginal mucosa. Commercial vaginal fertility products also contain ingredients that are physiologically decreased during ovulation in vivo (e.g., fructose and calcium), ingredients that may compromise cervical mucus and vaginal secretion hydration, possibly impairing sperm transport to the egg. At present, there are currently no vaginal products available to enhance quality of fertile cervical mucus, to supplement glycosaminoglycans and mucin production levels during ovulation, and to support hydration of the cervical mucus granules and fertile vaginal secretions, as needed to optimize sperm transport. Further, there are no vaginal fertility products that are free of mucosal immune-stimulating excipients.

Fertility compositions of the present disclosure (e.g., Fertility Composition Formulas X, Y, Z, AZ, AB, AB', and AC) can be used for: fertility enhancement, lubrication, vaginal hydration, sexual arousal, vaginal tightening, vaginal freshening, vaginal homeostasis, drug carrier base, or any combination thereof.

In another aspect, the fertility compositions of the present disclosure may serve to hydrate the vaginal mucosa of ovulating women without harming VMB, as an alternative means to optimizing sperm transport, or as an additional method for optimizing natural fertility.

Fertility compositions of this disclosure for use in ovulating women are pH matched to the vaginal pH of the ovulatory phase female subject, about pH 6.8 to about 7.8. In certain embodiments, a fertility composition has a pH of about 7.0 to about 7.6, of about 7.0 to about 7.4, of about 7.0 to about 7.2, or about 7.0.

In further embodiments, a fertility composition is formulated to be non-toxic to sperm (non-spermicidal) and may maintain, preserve, enhance, improve, or increase sperm survival and function, e.g., penetration into the fertile cervical mucus of an ovulating woman or improved potential of sperm to fertilize an oocyte. In yet further embodiments, a fertility composition may improve cervical mucus and fertile vaginal fluid hydration and quality to optimize sperm transport.

In yet further embodiments, a fertility composition is formulated to be non-toxic to oocytes or embryos and may maintain, preserve, enhance, improve, or increase oocyte or embryo survival and function, e.g., oocyte maturation, oocyte potential for fertilization by sperm, embryo potential for blastocyst development.

In certain embodiments, fertility compositions of this disclosure are used in a method of enhancing fertility, comprising administering a fertility composition intravaginally, to the vulva, or penis. In some embodiments, the fertility composition is administered within 24 hours, 12 hours, 6 hours, 2 hours, 1 hour, 30 minutes, 15 minutes, 5 minutes, just prior to, or during sexual intercourse.

In another aspect, the fertility compositions of the present disclosure are used in an assisted reproduction setting. For example, it may be applied to the hand, condom (interior or exterior), penis, or other collection device (e.g., vial, tube, bag) for use in semen collection for analysis, freezing, or use in artificial insemination (e.g., intrauterine insemination) or in vitro fertilization techniques (e.g., ICSI). In another example, the fertility compositions of the present disclosure may be applied to a medical device or instrument (e.g., catheter, pipette), or storage container for use in sperm collection (manual or surgical), artificial insemination, oocyte retrieval, oocyte freezing, oocyte thawing, ICSI, embryo culture, embryo biopsy, embryo freezing, embryo thawing, or embryo transfer.

In other embodiments, fertility compositions of the present disclosure are used in a method of increasing hydration of the vaginal mucosa comprising administering a fertility composition to the lower reproductive tract of a female subject. In some embodiments, the female subject is in the ovulatory phase of the menstrual cycle.

Fertility compositions of the present disclosure can be formulated as a semi-solid, gel, ointment, liquid, lotion, jelly, film, suspension, emulsion, mucilage, foam, cream, paste, or aerosol.

Exemplary formulations of fertility compositions and % ranges of each component as contemplated in the present disclosure are set forth as follows.

Fertility Composition Formula W comprises: 96.5% by weight purified water (range 50%-99%); 2% by weight carboxymethylcellulose (range 0.1%-10%); 0.01% by weight vascular endothelial growth factor (range 0.001%-1%); 0.2% by weight monobasic sodium phosphate (range 0.01%-2%); 0.7% by weight dibasic potassium phosphate (range 0.01%-2%); 0.25% by weight carvacrol (range 0.01%-0.5%); 0.1% by weight *Salvia plebeia* (range 0.001%-5%); 0.4% by weight sodium chloride (range 0.01%-1%); 0.04% xylose (range 0.01%-5%); and 0.001%-

1% by weight sodium hydroxide. In certain embodiments, Fertility Composition Formula W is formulated as a gel.

Fertility Composition Formula X comprises: 94.81% by weight purified water (range 50%-99%); 1.4% by weight polyvinyl alcohol (range 0.01%-5%); 1.5% by weight hypromellose (range 0.1%-10%); 1.46% by weight dibasic sodium phosphate (range 0.01%-2%); 0.47% by weight potassium citrate (range 0.01%-2%); 0.01% by weight oleuropein (range 0.01%-2%); 0.05% by weight *Salvia sclarea* (range 0.01%-1%); 0.2% by weight sodium chloride (range 0.01%-1%); 0.1% by weight xylose (range 0.01%-5%); and 0.001%-1% by weight sodium hydroxide. In certain embodiments, Fertility Composition Formula X is formulated as a gel.

Fertility Composition Formula Y comprises: 88.75% by weight purified water (range 50%-99%); 0.4% by weight poloxamer (range 0.1%-5%); 0.2% by weight monobasic sodium phosphate (range 0.01%-2%); 0.7% by weight dibasic potassium phosphate (range 0.01%-2%); 0.05% by weight *Salvia sclarea* (range 0.01%-1%); 0.4% by weight sodium chloride (range 0.01%-1%); 0.25% by weight carvacrol (range 0.01%-0.5%); 9% by weight Poly(2-methyl-2-oxazoline) (range 0.5%-40%); and 0.001%-1% by weight sodium hydroxide. In certain embodiments, Fertility Composition Formula Y is formulated as a gel.

Fertility Composition Formula Z comprises: 96.81% by weight purified water (range 50%-99%); 0.7% by weight hypromellose (range 0.1%-10%); 0.27% by weight carbomer (range 0.1%-5%); 1.46% by weight dibasic sodium phosphate (range 0.01%-2%); 0.47% by weight potassium citrate (range 0.01%-2%); 0.3% by weight phenoxyethanol (0.1%-2%); 0.2% by weight potassium sorbate (range 0.025%-1%); 0.05% by weight *Salvia sclarea* (range 0.01%-1%); 0.4% by weight sodium chloride (range 0.01%-1%); 0.04% by weight xylose (range 0.01%-5%); 0.001%-1% by weight sodium hydroxide. In certain embodiments, Fertility Composition Formula Z is formulated as a gel.

Fertility Composition Formula AZ comprises: 88.69% by weight purified water (range 50%-99%); 0.1% by weight *Salvia plebeia* (range 0.01%-1%); 0.1% by weight phenoxyethanol (range 0.1%-2%); 0.3% by weight caprylyl glycol (range 0.01%-2%); 0.5% by weight sodium chloride (range 0.01%-1%); 0.2% by weight monobasic potassium phosphate (range 0.01%-2%); 0.7% by weight dibasic sodium phosphate (range 0.01%-2%); 0.4% by weight xylose (range 0.01%-5%); 9% by weight poly(2-methyl-2-oxazoline) (range 0.5%-40%); and 0.001%-1% by weight sodium hydroxide. In certain embodiments, Fertility Composition Formula AZ is formulated as a gel.

Fertility Composition Formula AB comprises: 96.98% by weight purified water (range 75%-99.5%); 0.7% by weight cetyl hydroxyethylcellulose (range 0.001%-25%); 0.5% by weight hypromellose (range 0.001%-25%); 0.25% by weight carbomer (range 0.001%-20%); 0.188% by weight monobasic sodium phosphate (range 0.02%-2%); 0.687% by weight dibasic potassium phosphate (range 0.07%-7%); optionally 0.232% by weight phenethyl alcohol (0.02%-2%); optionally 0.148% by weight caprylyl glycol (range 0.01%-2%); 0.05% by weight *Salvia sclarea* (range 0.005%-1%); 0.2% by weight sodium chloride (range 0.001%-5%); 0.04% by weight xylose (range 0.001%-5%); and 0.25% by weight sodium hydroxide (range 0.001%-1%). In certain embodiments, Fertility Composition Formula AB is formulated as a gel.

Fertility Composition Formula AB' comprises: 96.24% by weight purified water (range 85%-98%); 0.7% by weight cetyl hydroxyethylcellulose (range 0.1%-2%); 0.9% by weight hypromellose (range 0.1%-2%); 0.27% by weight carbomer (range 0.1%-1%); 0.188% by weight monobasic sodium phosphate (range 0.1%-1%); 0.687% by weight dibasic potassium phosphate (range 0.1%-1%); optionally 0.232% by weight phenethyl alcohol (0.05%-1%); optionally 0.168% by weight caprylyl glycol (range 0.05%-1%); 0.05% by weight *Salvia sclarea* (range 0.01%-2.5%); 0.4% by weight sodium chloride (range 0.1%-1%); 0.04% by weight xylose (range 0.0015%-2.5%); and 0.12% by weight sodium hydroxide (range 0.001%-1%). In certain embodiments, Fertility Composition Formula AB' is formulated as a gel.

Fertility Composition Formula AC comprises: 97% by weight purified water (range 95%-99%); 1% by weight hypromellose (range 0.1%-2%); 0.5% by weight hydroxyethyl cellulose (range 0.1%-1%); 0.2% by weight monobasic sodium phosphate (range 0.02%-2%); 0.7% by weight dibasic potassium phosphate (range 0.07%-7%); 100,000 cfu *Lactobacillus* sp. (range 10,000 cfu-1,000,000 cfu); 0.464% by weight phenethyl alcohol (range 0.02%-2%); 0.336% by weight caprylyl glycol (range 0.01%-2%); 0.05% by weight *Salvia sclarea* (range 0.005%-1%); 0.12% by weight sodium chloride (range 0.001%-5%); 0.04% by weight xylose (range 0.001%-5%); and 0.001% by weight sodium hydroxide (range 0.001%-1%). In certain embodiments, Fertility Composition Formula AC is formulated as a gel.

In certain embodiments, topical, isotonic, biome-friendly fertility compositions of the present disclosure comprise xylose at a concentration ranging from about 0.01% to about 2.5% by weight and a *Salvia* extract at a concentration ranging from about 0.01% to about 2.5% by weight, wherein the composition has a pH of about 6.8 to about 7.8 and is optionally formulated as a gel. In some embodiments, the fertility composition comprises xylose at a concentration ranging from about 0.02% to about 0.5% by weight and *Salvia* extract at a concentration ranging from about 0.01% to about 0.2% by weight. In some embodiments, the *Salvia* extract is *Salvia sclarea*, *Salvia hispanica*, *Salvia plebeia*, or combinations thereof.

The fertility compositions may further comprise a non-irritating viscosity increasing agent at a concentration ranging from about 0.1% to about 25% by weight. Examples of non-irritating viscosity-increasing agent include a cellulose ether (e.g., methyl cellulose, carboxymethyl cellulose, hypromellose, ethylcellulose, ethyl methyl cellulose, hydroxyethyl cellulose, hydroxypropyl cellulose, hydroxyethyl methyl cellulose, ethyl hydroxyethyl cellulose, or a combination thereof) carbomer, polyoxazoline, or any combination thereof. In some embodiments, non-irritating viscosity-increasing agent is hypromellose and carbomer homopolymer type B together at a total concentration ranging from about 0.5% to about 5% by weight. In further embodiments, the ratio of hypromellose to carbomer homopolymer type B in the composition ranges from about 2:1 to about 6:1. In some embodiments, the non-irritating viscosity-increasing agent is hypromellose, a carbomer, carobxymethylcellulose, or poly(2-methyl-2-oxazoline).

The fertility compositions may further comprise a surfactant at a total concentration ranging from about 0.1% to about 2% by weight. Examples of surfactants include cetyl hydroxyethylcellulose, polyvinyl alcohol, poloxamer, and any combination thereof. In some embodiments, the surfactant is a cetyl hydroxyethylcellulose at a total concentration ranging from about 0.35% to about 2% by weight. In other embodiments, the surfactant is a polyvinyl alcohol at a total concentration ranging from about 1% to about 1.5% by weight. In yet other embodiments, the surfactant is a poloxamer at a total concentration ranging from about 0.1% to about 0.5% by weight.

The fertility compositions may include a paraben-free preservative at a total concentration ranging from about 0.005% to 5% by weight. In some embodiments, the paraben-free preservative is a phenethyl alcohol, caprylyl glycol, phenoxyethanol, a sorbate, oleuropein, acemannan, carvacrol, or any combination thereof. In yet further embodiments, the paraben-free preservative is a phenethyl alcohol and caprylyl glycol together at a total concentration ranging from about 0.25% to about 1% by weight. In other embodiments, the paraben-free preservative is a phenoxyethanol and caprylyl glycol at a total concentration ranging from about 0.25% to about 1% by weight. In yet other embodiments, the paraben-free preservative is a phenoxyethanol and a sorbate, wherein the sorbate is a potassium sorbate, at a total concentration ranging from about 0.4% to about 1% by weight. In yet other embodiments, the paraben-free preservative is oleuropein. In yet other embodiments, the paraben-free preservative is a carvacrol at a total concentration ranging from about 0.01% to about 0.5% by weight.

The fertility compositions may further comprise a buffering agent at a total concentration ranging from about 0.5% to about 2.5% by weight. In certain embodiments, the buffering agent is sodium phosphate (monobasic, dibasic, or both), potassium phosphate (monobasic, dibasic, or both), potassium citrate, or any combination thereof. In some embodiments, the buffering agent is sodium phosphate (monobasic, dibasic, or both) and potassium phosphate (monobasic, dibasic, or both) at a total concentration ranging from about 0.5% to about 1.5% by weight. In other embodiments, the buffering agent is sodium phosphate and potassium citrate at a total concentration ranging from about 1% to about 2% by weight.

The fertility compositions may also comprise a pH modifying agent at a total concentration ranging from about 0.001% to about 2% by weight. The pH modifying agent can be an acidifying agent, an alkalizing agent, or both. In certain embodiments, the alkalizing agent is ammonia, ammonium carbonate, diethanolamine, monoethanolamine, potassium hydroxide, dibasic potassium phosphate, sodium bicarbonate, sodium borate, sodium carbonate, sodium hydroxide, dibasic sodium phosphate, trolamine, or any combination thereof. In some embodiments, the alkalizing agent is sodium hydroxide at a total concentration ranging from about 0.01% to about 1% by weight.

The fertility compositions may further comprise an osmolality adjuster, such as sodium chloride, potassium chloride, or both, at a total concentration ranging from about 0.1% to about 1% by weight.

The fertility compositions may further comprise a solvent, such as water in an amount of about 85% to about 98% by weight.

An exemplary topical, isotonic, biome-friendly fertility composition comprises xylose at a concentration ranging from about 0.01% to about 2.5% by weight or about 0.02% to about 0.5% by weight and *Salvia plebeia* at a concentration ranging from about 0.05% to about 0.15% by weight, and the composition further comprises: a non-irritating viscosity-increasing agent, wherein the non-irritating viscosity-increasing agent is carboxymethyl cellulose at a total concentration ranging from about 1% to about 3% by weight; a vascular endothelial growth factor at a total concentration ranging from about 0.005% to about 0.05% by weight; a buffering agent, wherein the buffering agent is monobasic sodium phosphate and dibasic potassium phosphate together at a total concentration ranging from about 0.5% to about 1.1% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; and a pH modifier, wherein the pH modifier is sodium hydroxide at a concentration ranging from about 0.001% to about 1% by weight, and optionally, a paraben-free preservative, wherein the paraben-free preservative is preferably carvacrol at a total concentration ranging from about 0.01% to about 0.5% by weight, wherein the composition has a pH of about 6.8 to about 7.8. The fertility composition can be formulated as a gel.

Another exemplary topical, isotonic, biome-friendly fertility composition comprises xylose at a concentration ranging from about 0.01% to about 2.5% by weight or about 0.02% to about 0.5% by weight and *Salvia plebeia* at a concentration ranging from about 0.05% to about 0.15% by weight, and the composition further comprises: a non-irritating viscosity-increasing agent, wherein the non-irritating viscosity-increasing agent is poly(2-methyl-2-oxazoline) at a total concentration ranging from about 5% to about 10%; a buffering agent, wherein the buffering agent is monobasic potassium phosphate and dibasic sodium phosphate together at a total concentration ranging from about 0.5% to about 1.1% by weight; an osmolality adjuster, wherein the osmolality adjuster is sodium chloride at a total concentration ranging from about 0.1% to about 0.75% by weight; a solvent, wherein the solvent is water at a concentration ranging from about 87% to about 94% by weight; a pH modifier, wherein the pH modifier is sodium hydroxide at a concentration ranging from about 0.001% to about 1% by weight; and optionally, a paraben-free preservative, wherein the paraben-free preservative is preferably a phenoxyethanol and caprylyl glycol together at a total concentration ranging from about 0.1% to about 0.7% by weight, and wherein the composition has a pH of about 6.8 to about 7.8. The fertility composition can be formulated as a gel.

Another example of a topical, isotonic, biome-friendly fertility composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose at a total concentration ranging from about 1% to about 2% by weight; a surfactant, wherein the surfactant is polyvinyl alcohol at a total concentration ranging from about 1% to about 2% by weight; a buffering agent, wherein the buffering agent is dibasic sodium phosphate and potassium citrate together at a total concentration ranging from about 1% to about 3% by weight; an osmolality adjuster, wherein the osmolality adjuster is sodium chloride at a total concentration ranging from about 0.1% to about 0.3% by weight; a solvent, wherein the solvent is water at a concentration ranging from about 95% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably oleuropein at a total concentration ranging from about 0.01% to about 0.1% by weight, and wherein the composition has a pH of about 6.8 to about 7.8. The fertility composition can be formulated as a gel.

Yet another exemplary topical, isotonic, biome-friendly fertility composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is poly(2-methyl-2-oxazoline) at a total concentration ranging from about 5% to about 10% by weight; a surfactant, wherein the surfactant is a poloxamer at a total concentration ranging from about 0.1% to about 0.7% by weight; a buffering agent, wherein the buffering agent is monobasic sodium phosphate and dibasic potassium phosphate together at a total concentration ranging from about 0.5% to about 1.1% by weight; an osmolality adjuster, wherein the osmolality adjuster is sodium chloride at a total concentration ranging from about 0.1% to about 0.5% by weight; a solvent, wherein the solvent is water at a concentration ranging from about 87% to about 94% by weight; a pH modifier, wherein the pH modifier is sodium hydroxide at a concentration ranging from about 0.001% to about 1% by weight; and optionally, a paraben-free preservative, wherein the paraben-free preservative is preferably carvacrol at a total concentration ranging from about 0.03% to about 0.5% by weight, and wherein the composition has a pH of about 6.8 to about 7.8. The fertility composition can be formulated as a gel.

Another example of a topical, isotonic, biome-friendly fertility composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose and carbomer homopolymer type B together at a total concentration ranging from about 0.2% to about 3% by weight, and wherein the ratio of hypromellose to carbomer homopolymer type B in the composition is about 2:1; a surfactant, wherein the surfactant is cetyl hydroxyethylcellulose at a total concentration ranging from about 0.5% to about 1% by weight; a buffering agent, wherein the buffering agent is monobasic sodium phosphate and dibasic potassium phosphate together at a total concentration ranging from about 0.5% to about 1.5% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably a phenethyl alcohol and caprylyl glycol together at a total concentration ranging from about 0.2% to about 0.9% by weight, and wherein the composition has a pH of about 6.8 to about 7.8. The fertility composition can be formulated as a gel.

Another example of a topical, isotonic, biome-friendly fertility composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose and carbomer homopolymer type B together at a total concentration ranging from about 0.2% to about 2% by weight, and wherein the ratio of hypromellose to carbomer homopolymer type B in the composition is about 3.3:1; a surfactant, wherein the surfactant is cetyl hydroxyethylcellulose at a total concentration ranging from about 0.5% to about 1% by weight; a buffering agent, wherein the buffering agent is monobasic sodium phosphate and dibasic potassium phosphate together at a total concentration ranging from about 0.5% to about 1.5% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably a phenethyl alcohol and caprylyl glycol together at a total concentration ranging from about 0.2% to about 0.9% by weight, and wherein the composition has a pH of about 6.8 to about 7.8.

The fertility composition can be formulated as a gel.

Yet another exemplary topical, isotonic, biome-friendly fertility composition comprises xylose at a concentration ranging from about 0.01% to about 2.5% or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose and carbomer homopolymer type B together at a total concentration ranging from about 0.75% to about 1.5% by weight, and wherein the ratio of hypromellose to carbomer homopolymer type B in the composition is about 2.6:1; a buffering agent, wherein the buffering agent is dibasic sodium phosphate and potassium citrate together at a total concentration ranging from about 1% to about 3% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably a phenoxyethanol and potassium sorbate together at a total concentration ranging from about 0.25% to about 0.75% by weight, and wherein the composition has a pH of about 6.8 to about 7.8. The fertility composition can be formulated as a gel.

Another exemplary topical, isotonic, biome-friendly fertility composition comprises xylose at a concentration ranging from about 0.01% to about 2.5% or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hydroxyethyl cellulose and hypromellose at a total concentration ranging from about 0.2% to about 3%; a buffering agent, wherein the buffering agent is monobasic sodium phosphate and dibasic potassium phosphate together at a total concentration ranging from about 0.5% to about 1.5% by weight; a *Lactobacillus* species that is capable of colonizing the vaginal wall in an amount of about 10,000 cfu to about 1,000,000 cfu; an osmolality adjuster, wherein the osmolality adjuster is sodium chloride at a total concentration ranging from about 0.1% to about 0.7% by weight; a solvent, wherein the solvent is water at a concentration ranging from about 95% to about 99% by weight; a pH modifier, wherein the pH modifier is sodium hydroxide at a concentration ranging from about 0.001% to about 1% by weight; and optionally, a paraben-free preservative, wherein the paraben-free preservative is preferably a phenethyl alcohol and caprylyl glycol together at a total concentration ranging from about 0.2% to about 0.9% by weight, and wherein the composition has a pH of about 6.8 to about 7.8. The fertility composition can be formulated as a gel.

(4) Sexual Lubricant and Vaginal Hydration Compositions

In yet another aspect of the present disclosure, compositions are provided that may be used as sexual lubricants or for hydrating the vagina, or both. Lubricants alleviate discomfort or pain during intercourse when vaginal mucosal secretions are inadequate. Inadequate vaginal secretion may occur due to lack of arousal, aging (menopause), as a side effect to medications (such as antidepressants and birth control pills), or hormone disruptions. Over 70% of all American women have used a sexual lubricant at some time in their lives. However, there are few lubricants on the market that lack ingredients shown to cause irritation or cytokine release from LRT cells or high levels of inflammatory endotoxins. The most recent lubricants touted as "break-through" for women with vaginal dryness have been the hyaluronic acid (HA) based lubricants. However, the presence of elevated HA is a physiologic trigger for inflammasome production in the human body. Additionally, HA production systems result in high levels of endotoxin and bacterial nucleic acids.

The sexual lubricant or vaginal hydration compositions of the present disclosure are matched to the vulvar and vaginal pH of the subject, e.g., for a reproductive aged woman (about pH 3.5 to about 5.5), an ovulatory phase woman (about pH 6.8 to about 7.8), pregnant woman (about pH 4.5 to about 6.5), or postmenopausal woman (about.pH 4.5 to about 6.8).

The compositions for lubrication or hydration of vaginal fluids and/or mucosa provided herein (e.g., Menopause Lubricant Composition Formulas W, X, Y, Z, AB) can be used for perineal massage, contraception, anti-microbial, fertility enhancement, sexual lubrication, vaginal hydration, sexual arousal, vaginal tightening, vaginal freshening, vaginal homeostasis, as a drug carrier base, or any combination thereof.

In certain embodiments, the hydration/lubricant compositions may include a therapeutic agent, such as a hormone useful for treating genitourinary syndrome of menopause (e.g., estradiol, estriol, estropipate, testosterone, progesterone, DHEA, or a combination thereof) or other natural products or botanicals that support hormone production. In certain embodiments, the sexual hydration/lubricant compositions further comprise an agent that enhances vasodilation. In some embodiments, an agent that enhances vasodilation is L-arginine, niacin, nicotinamide, alprostadil, a phosphodiesterase inhibitor, or a combination thereof.

In certain embodiments, sexual lubricant compositions may be used in methods of enhancing arousal during sexual intercourse, comprising topically applying a sexual lubricant composition to the lower reproductive tract (e.g., intravaginally, to the vulva) of a female subject, to the penis, to condoms (interior or exterior), or to other devices (e.g., sex toys). In some embodiments, sexual lubricant compositions are administered within 24 hours, 12 hours, 6 hours, 2 hours, 1 hour, 30 minutes, 15 minutes, 5 minutes, just prior to, or during sexual intercourse.

In certain embodiments, vaginal hydration compositions may be used in methods of increasing hydration of the vaginal mucosa or secretions, comprising topically applying a vaginal hydration composition to the lower reproductive tract (e.g., intravaginally, to the vulva) of a female subject or to the penis, condoms, or other devices or instruments (e.g., catheter, speculum, vaginal ultrasound probe, uterine balloon tamponade) prior to insertion to the vagina.

Lubricant/vaginal hydration compositions of the present disclosure can be formulated as a semi-solid, gel, ointment, liquid, lotion, jelly, film, suspension, emulsion, mucilage, foam, cream, paste, or aerosol.

Exemplary formulations of compositions for vaginal hydration or lubrication in menopausal subjects ("menopause compositions") and % ranges of each component as contemplated in the present disclosure are set forth as follows. Such menopause compositions are pH matched to the vulvar and vaginal pH of post-menopausal subjects (about pH 4.5 to about 6.8).

Menopause Composition Formula W comprises: 96.34% by weight purified water (range 50-99%); 0.04% by weight xylose (range 0.01%-5%); 0.91% by weight poloxamer (range 0.1%-5%); 0.12% by weight benzoic acid (range 0.003%-5%); 0.14% by weight sodium chloride (range 0.01%-1%); 1.0% by weight hypromellose (range 0.1%-10%); 0.05% by weight *Salvia sclarea* (range 0.1%-1%); 0.7% by weight monobasic sodium phosphate (range 0.07%-7%); 0.135% by weight dibasic sodium phosphate (range 0.01%-1.4%); 1.4% by weight polyvinyl alcohol (range 0.01%-5%); and 0.001%-1% by weight sodium hydroxide. In certain embodiments, Menopause Composition Formula W is formulated as a gel.

Menopause Composition Formula X comprises: 96.14% by weight purified water (range 50%-99%); 0.04% by weight xylose (range 0.01%-5%); 0.9% by weight poloxamer (range 0.1%-5%); 0.7% by weight monobasic sodium phosphate (range 0.07%-7%); 0.135% dibasic sodium phosphate (range 0.01%-1.4%); 0.03% by weight cranberry extract (range 0.01%-0.5%); 0.14% by weight sodium chloride (range 0.01%-1%); 2.0% by weight hypromellose (range 0.1%-10%); and 0.05% by weight *Salvia sclarea* (range 0.01%-1%).

In certain embodiments, Menopause Composition Formula X is formulated as a gel.

Menopause Composition Formula Y comprises: 98.0% by weight purified water (range 50%-99%); 0.04% by weight xylose (range 0.01%-5%); 0.7% by weight monobasic sodium phosphate (0.07%-7%); 0.135% by weight dibasic sodium phosphate (0.01%-1.4%); 0.232% by weight phenethyl alcohol (range 0.01%-1%); 0.148% by weight caprylyl glycol (range 0.01%-2%); 0.14% by weight sodium chloride (range 0.01%-1%); 0.14% by weight carbomer (range 0.01%-5%); 0.42% by weight hypromellose (range 0.1%-10%); 0.05% by weight *Salvia plebeia* (range 0.01%-1%); and 0.005% by weight sodium hydroxide. (range 0.001%-1%) In certain embodiments, Menopause Composition Formula Y is formulated as a gel.

Menopause Composition Formula Z comprises: 95.7% by weight purified water (range 50%-99%); 0.1% by weight xylose (range 0.01%-5%); 1.07% by weight sodium citrate (range 0.01%-2%); 0.2% by weight potassium sorbate (range 0.025%-1%); 0.15% by weight sodium benzoate (range 0.1%-10%); 0.24% by weight sodium chloride (range 0.01%-1%); 1.3% by weight hypromellose (range 0.1%-10%); 1.0% by weight carboxymethylcellulose (range 0.1%-10%); 0.05% by weight *Salvia sclarea* (range 0.01%-1%); 0.17% by weight citric acid (range 0.02%-20%); and 0.001% by weight sodium hydroxide (range 0.001%4%). In certain embodiments, Menopause Composition Formula Z is formulated as a gel.

Menopause Composition Formula AB comprises: 96.635% by weight purified water (range 92%-98%); 1.5% by weight hypromellose (range 0.5%-2%); 0.24% by weight carbomer (range 0.1%-1%); 0.7% by weight monobasic sodium phosphate (range 0.5%-1.0%); 0.165% by weight dibasic sodium phosphate (range 0.01%-0.5%); optionally 0.232% by weight phenethyl alcohol (range 0.1%-1% by weight); 0.15% by weight sodium chloride (range 0.01%-1%); optionally 0.168% by weight caprylyl glycol (range 0.1%-1% by weight); 0.05% by weight *Salvia sclarea* (range 0.015%-2.5%); 0.04% by weight xylose (range 0.015%-2.5%); and 0.12% by weight sodium hydroxide (range 0.001%-1%). In certain embodiments, Menopause Composition Formula AB is formulated as a gel.

In certain embodiments, a topical, isotonic, biome-friendly menopause composition of the present disclosure comprise xylose at a concentration ranging from about 0.01% to about 2.5% by weight and *Salvia* extract at a concentration ranging from about 0.01% to about 2.5% by weight, and wherein the composition has a pH ranging from about 4.0 to about 6.8 and is optionally formulated as a gel. In some embodiments, the composition comprises xylose at a concentration ranging from about 0.02% to about 0.5% by weight and *Salvia* extract at a concentration ranging from about 0.01% to about 0.2% by weight. In some embodiments, the *Salvia* extract is *Salvia sclarea, Salvia hispanica, Salvia plebeia*, or combinations thereof.

The menopause compositions may further comprise a non-irritating viscosity increasing agent at a concentration ranging from about 0.1% to about 10% by weight. In certain embodiments, the non-irritating viscosity-increasing agent is a cellulose ester (e.g., methylcellulose, ethylcellulose, ethyl methyl cellulose, hydroxyethyl cellulose, hydroxypropyl cellulose, hydroxyethyl methyl cellulose, hyroxypropyl methyl cellulose (hypromellose), ethyl hydroxyethyl cellulose, carboxymethyl cellulose) carbomer, polyoxazoline, or any combination thereof. In some embodiments, the non-irritating viscosity-increasing agent is hypromellose at a total concentration ranging from about 0.3% to about 4% by weight. In other embodiments, the non-irritating viscosity-increasing agent is a carbomer at a total concentration ranging from about 0.1% to about 1% by weight. In yet other embodiments, the non-irritating viscosity-increasing agent is hypromellose and carbomer homopolymer type B together at a total concentration ranging from about 0.1% to about 5% by weight. In yet further embodiments, the ratio of hypromellose to carbomer homopolymer type B in the composition ranges from about 2:1 to about 8:1. In other embodiments, the non-irritating viscosity-increasing agent is hypromellose and carboxymethylcellulose together at a total concentration ranging from about 1% to about 3% by weight. In yet other embodiments, the non-irritating viscosity-increasing agent is poly(2-methyl-2-oxazoline) at a total concentration ranging from about 1% to about 10% by weight.

The menopause compositions may also comprise a surfactant at a total concentration ranging from about 0.5% to about 5% by weight. In certain embodiments, the surfactant is a cetyl hydroxyethylcellulose, polyvinyl alcohol, poloxamer, or any combination thereof. In some embodiments, the surfactant is a cetyl hydroxyethylcellulose at a total concentration ranging from about 0.5% to about 2% by weight. In other embodiments, the surfactant is a polyvinyl alcohol at a total concentration ranging from about 1% to about 2% by weight. In yet other embodiments, the surfactant is a poloxamer at a total concentration ranging from about 0.5% to about 1.5% by weight.

The menopause compositions may further comprise a paraben-free preservative at a total concentration ranging from about 0.005% to about 5% by weight. In certain embodiments, the paraben-free preservative is a phenethyl alcohol, caprylyl glycol, phenoxyethanol, benzoic acid, a benzoate, a sorbate, cranberry extract, oleuropein, acemannan, carvacrol, or any combination thereof. In some embodiments, wherein the paraben-free preservative is a phenethyl alcohol and caprylyl glycol together at a total concentration ranging from about 0.25% to about 1.2% by weight. In other embodiments, the paraben-free preservative is a phenoxyethanol and caprylyl glycol at a total concentration ranging from about 0.25% to about 0.75% by weight. In yet other embodiments, the paraben-free preservative is benzoic acid at a total concentration ranging from about 0.025% to about 0.75% by weight. In yet other embodiments, the paraben-free preservative is a potassium sorbate and sodium benzoate at a total concentration ranging from about 0.1% to about 0.5% by weight.

The menopause compositions may further comprise a buffering agent at a total concentration ranging from about 0.5% to about 4% by weight. In certain embodiments, the buffering agent is a sodium phosphate (monobasic, dibasic, or both), potassium phosphate (monobasic, dibasic, or both), citric acid, sodium citrate, or any combination thereof. In some embodiments, the buffering agent is a dibasic sodium phosphate and a monobasic sodium phosphate at a total concentration ranging from about 0.5% to about 1.5% by weight. In yet other embodiments, the buffering agent is citric acid and sodium citrate at a total concentration ranging from about 0.75% to about 1.5% by weight. In yet other embodiments, the buffering agent is sodium phosphate at a total concentration ranging from about 0.25% to about 1.25% by weight.

The menopause compositions may further comprise an osmolality adjuster, such as sodium chloride, potassium chloride, or both, at a total concentration ranging from about 0.1% to about 1% by weight.

The menopause compositions may further comprise at least one pH modifying agent at a total concentration ranging from about 0.001% to about 2% by weight. At least one pH modifying agent may be an acidifying agent, an alkalizing agent, or both. In some embodiments, the alkalizing agent is ammonia, ammonium carbonate, diethanolamine, monoethanolamine, potassium hydroxide, potassium phosphate dibasic, sodium bicarbonate, sodium borate, sodium carbonate, sodium hydroxide, sodium lactate, sodium phosphate dibasic, trolamine, or any combination thereof. In a specific embodiment, the alkalizing agent is sodium hydroxide at a total concentration ranging from about 0.01% to about 1% by weight.

The menopause compositions may also include a solvent, such as water in an amount from about 85% to about 98%.

An exemplary topical, isotonic, biome-friendly menopause composition comprises xylose at a concentration ranging from about 0.01% to about 2.5% by weight or about 0.02% to about 0.5% by weight and *Salvia* extract of the composition is *Salvia sclarea* at a concentration ranging from about 0.025% to about 0.075% by weight, and the composition further comprises: a non-irritating viscosity-increasing agent, wherein the non-irritating viscosity-increasing agent is hypromellose at a total concentration ranging from about 0.75% to about 1.25% by weight; a surfactant, wherein the surfactant is polyvinyl alcohol and poloxamer together at a total concentration ranging from about 2% to about 2.5% by weight; a buffering agent, wherein the buffering agent is a dibasic sodium phosphate and a monobasic sodium phosphate at a total concentration ranging from about 0.5% to about 1% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably benzoic acid at a total concentration ranging from about 0.05% to about 0.25% by weight, and wherein the composition has a pH ranging from about 4.5 to about 6.8. The menopause composition can be formulated as a gel.

Another exemplary topical, isotonic, biome-friendly menopause composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose and carbomer homopolymer type B together at a total concentration ranging from about 1.0% to about 2% by weight, and wherein the ratio of hypromellose to carbomer homopolymer type B in the composition is about 6.2:1; a buffering agent, wherein the buffering agent is a dibasic sodium phosphate and a monobasic sodium phosphate at a total concentration ranging from about 0.5% to about 1% by weight; an osmolality adjuster, wherein the osmolality adjuster is sodium chloride at a total concentration ranging from about 0.1% to about 0.7% by weight; a solvent, wherein the solvent is water at a concentration ranging from about 92% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably a phenethyl alcohol and caprylyl glycol together at a total concentration ranging from about 0.2% to about 0.75% by weight, and wherein the composition has a pH ranging from about 4.5 to about 6.8. The menopause composition can be formulated as a gel.

Another example of a topical, isotonic, biome-friendly menopause composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose at a total concentration ranging from about 1.25% to about 2.25% by weight; a surfactant, wherein the surfactant is poloxamer at a total concentration ranging from about 0.75% to about 1.25% by weight; a buffering agent, wherein the buffering agent is monobasic sodium phosphate and dibasic sodium phosphate at a total concentration ranging from about 0.5% to about 1% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; and optionally, a paraben-free preservative, wherein the paraben-free preservative is preferably a cranberry extract at a total concentration ranging from about 0.01% to about 0.05% by weight, and wherein the composition has a pH ranging from about 4.5 to about 6.8. The menopause composition can be formulated as a gel.

Yet another example of a topical, isotonic, biome-friendly menopause composition comprises xylose at a concentration ranging from about 0.01% to about 2.5% by weight or about 0.02% to about 0.5% by weight and *Salvia plebeia* at a concentration ranging from about 0.025% to about 0.075% by weight, and the composition further comprises: a non-irritating viscosity-increasing agent, wherein the non-irritating viscosity-increasing agent is carbomer homopolymer type B and hypromellose at a total concentration ranging from about 0.10% to about 1% by weight, and wherein the ratio of hypromellose to carbomer in the composition is about 3:1; a buffering agent, wherein the buffering agent is monobasic sodium phosphate and dibasic sodium phosphate at a total concentration ranging from about 0.5% to about 1% by weight; an osmolality adjuster, wherein the osmolality adjuster is sodium chloride at a total concentration ranging from about 0.1% to about 0.7% by weight; a pH modifier, wherein the pH modifier is sodium hydroxide at a concentration ranging from about 0.001% to about 1%; a solvent, wherein the solvent is water at a concentration ranging from about 95% to about 99% by weight; optionally, a paraben-free preservative, wherein the paraben-free preservative is preferably phenethyl alcohol and caprylyl glycol together at a total concentration ranging from about 0.25% to about 0.5% by weight, and wherein the composition has a pH ranging from about 4.5 to about 6.8. The menopause composition can be formulated as a gel.

Yet another exemplary topical, isotonic, biome-friendly menopause composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is hypromellose and carboxymethyl cellulose together at a total concentration ranging from about 1.5% to about 2.5% by weight, and wherein the ratio of hypromellose to carboxymethyl cellulose in the composition is about 1.3:1; a buffering agent, wherein the buffering agent is citric acid and sodium citrate together at a total concentration ranging from about 1% to about 1.25% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; a pH modifier, wherein the pH modifier is sodium hydroxide at a concentration ranging from about 0.001% to about 1%; and optionally, a paraben-free preservative, wherein the paraben-free preservative is preferably potassium sorbate and sodium benzoate together at a total concentration ranging from about 0.25% to about 0.5% by weight, wherein the composition has a pH ranging from about 4.5 to about 6.8. The menopause composition can be formulated as a gel.

(5) Freshening Compositions

In yet another aspect of the present disclosure, freshening compositions for the female lower reproductive tract are provided. Douching is commonly performed by women seeking cleanliness of LRT and control of unwanted feminine odors. These odors arise following vaginal infection, sweating in the external genital area, following sexual intercourse, and following menses. However, douching is associated with dramatic increases in LRT cancer, STD infection, bacterial vaginosis, infertility, and abnormal birth outcomes. Use of low pH "balancing" gels that bind to the vaginal wall and provide long-lasting effect has been shown to significantly lower vaginal pH and bacterial vaginosis symptoms. However, gels that are currently sold for this use cause moderate to severe LRT cell toxicity and damage to vaginal *Lactobacillus*, which are requisite for vaginal homeostasis. The freshening compositions of the present disclosure can be used to freshen or cleanse LRT (e.g., vagina or vulva), control vaginal odor, and are pH matched to the vulvar and vaginal pH of the subject, e.g., for a reproductive aged woman (about 3.5 to about 5.5), an ovulatory phase woman (about 6.8 to about 7.8), pregnant woman (about pH 4.5 to about 6.5), or postmenopausal woman (around about 4.5 to about 6.8), are non-irritating for the LRT, and support homeostasis of the LRT, including preserving vaginal microbiota.

Freshening compositions of the present disclosure can be formulated as a semi-solid, gel, ointment, liquid, lotion, jelly, film, suspension, emulsion, mucilage, foam, cream, paste, or aerosol.

In some embodiments the freshening compositions are formulated as a bioadhesive gel or film, so that they will not leak out of the vagina following application and can provide pH adjustment to the LRT mucosa for 24 hours or more.

Freshening compositions of the present disclosure (e.g., Freshening Composition Formulas W, X, Y, Z, AB, AZ, BY) can be used for perineal massage, contraception, anti-microbial, fertility enhancement, sexual lubrication, vaginal hydration, sexual arousal, vaginal tightening, vaginal freshening, vaginal homeostasis, as a drug carrier base, or any combination thereof.

In certain embodiments, the freshening compositions may be used in methods of cleansing the lower reproductive tract or controlling unwanted feminine odor, comprising administering the freshening composition to the lower reproductive tract of a female subject (e.g., vagina or vulva).

Exemplary formulations of freshening compositions and % ranges of each component as contemplated in the present disclosure are set forth as follows.

Freshening Composition Formula W comprises: 90.89% by weight purified water (range 50%-99%); 2.0% by weight polyvinyl alcohol (range 0.01%-5%); 4.8% by weight cetyl hydroxyethyl cellulose (range 0.1%40%), 1.0% by weight poly(2-methyl-2-oxazoline) (range 0.5%-40%); 0.139% by weight lactic acid (range 0.01%-2%); 0.683% by weight sodium lactate (range 0.01%-5%); 0.05% by weight *Salvia sclarea* (range 0.01%-1%); 0.2% by weight sodium chloride (range 0.01%-1%); 0.04% by weight xylose (range 0.01%-5%), and 0.12% by weight sodium hydroxide (range 0.001%-1%). In certain embodiments, Freshening Composition Formula W is formulated as a gel.

Freshening composition formula X comprises: 89.45% by weight purified water (range 50%-99%); 9.0% by weight poly(2-methyl-2-oxazoline) (range 0.5%-40%); 0.139% by weight lactic acid (range 0.01%-2%); 0.683% by weight sodium lactate (range 0.01%-5%); 0.232% by weight phenethyl alcohol (range 0.01%-1%); 0.168 caprylyl glycol (0.01%-2%); 0.05% by weight *Salvia sclarea* (range 0.01%-1%); 0.2% by weight sodium chloride (range 0.01%-1%); 0.04% by weight xylose (range 0.01%-5%); and 0.04% by weight (range 0.001%-1%). In certain embodiments, Freshening Composition Formula X is formulated as a gel.

Freshening composition formula Y comprises: 95.16% by weight purified water (range 50%-99%); 1.0% by weight cetyl hydroxyethylcellulose (range 0.1%-10%); 1.5% by weight carbomer (range 0.01%-5%); 0.66% by weight ascorbic acid (range 0.01%-5%); 0.49% by weight sodium ascorbate (range 0.01%-5%); 0.232% by weight phenethyl alcohol (range 0.01%-1%); 0.168% by weight caprylyl glycol (range 0.01%-2%); 0.05% by weight *Salvia sclarea* (range 0.01%-1%); 0.3% by weight sodium chloride (range 0.01%-1%); and 0.08% by weight xylose (range 0.01%-5%). In certain embodiments, Freshening Composition Formula Y is formulated as a gel.

Freshening composition formula Z comprises: 95.80% by weight purified water (range 50%-99%); 2.0% by weight polyvinyl alcohol (range 0.01%-5%); 1.0% by weight carbomer (0.01%-5%); 0.139% by weight lactic acid (range 0.01%-2%); 0.683% by weight sodium lactate (range 0.01%-5%); 0.05% by weight *Salvia sclarea* (range 0.01%-1%); 0.2% by weight sodium chloride (range 0.01%-1%); 0.04% by weight xylose (range 0.01%-5%); and 0.009% by weight sodium hydroxide (range 0.001%-1%). In certain embodiments, Freshening Composition Formula Z is formulated as a gel.

Freshening composition formula AZ comprises: 83.9% by weight purified water (range 50%-99%); 0.1% by weight *Salvia plebeia* (range 0.01%-1%); 0.03% by weight cranberry extract (0.01%-5%); 0.5% by weight sodium chloride (0.01%-1%); 0.04% by weight xylose (0.01%-5%); 15% by weight poly(2-methyl-2-oxazoline) (range 0.5%-40%); and 0.43% by weight sodium hydroxide (range 0.001%-1%). In certain embodiments, Freshening Composition Formula AZ is formulated as a gel.

Freshening composition formula BY comprises: 96.03% by weight purified water (range 50%-99%); 0.04% by weight xylose (0.01%-5%); 0.4% by weight monobasic sodium phosphate (range 0.01%-2%); 0.7% by weight sodium citrate; 0.25% by weight caprylyl glycol (range 0.01%-2%); 0.14% by weight sodium chloride (range 0.01%-1%); 1.1% by weight hypromellose (range 0.1%-10%); 0.24% by weight carbomer (range 0.01%-5%); 0.1% by weight *Salvia plebeia* (range 0.01%-1%); and 1.0% by weight polyvinyl alcohol (range in a quantity required to complete 100%). In certain embodiments, Freshening Composition Formula BY is formulated as a gel.

Freshening composition formula AB comprises: 95.328% by weight purified water (range 90%-99%); 1.0% by weight cetyl hydroxyethylcellulose (range 0.25%-10%); 2.0% by weight carbomer (range 0.1%-3%); 0.139% by weight lactic acid (range 0.01%-0.5%); 0.683% by weight sodium lactate (range 0.05%-1%); 0.05% by weight *Salvia sclarea* (range 0.025%-2.5%); 0.2% by weight sodium chloride (range 0.1%-1%); 0.04% by weight xylose (range 0.025%-2.5%); 0.16% by weight sodium hydroxide (range 0.001%-1%); optionally 0.232% by weight phenethyl alcohol (range 0.1%-1%); and optionally 0.168% by weight caprylyl glycol (range 0.1%-1%).

In certain embodiments, topical, isotonic, biome-friendly freshening compositions of the present disclosure comprise xylose at a concentration ranging from about 0.01% to about 2.5% by weight and a *Salvia* extract at a concentration ranging from about 0.01% to about 2.5% by weight, and wherein the composition has a pH ranging from about 3.5 to about 6.8 and is optionally formulated as a gel. The pH of the freshening compositions may be matched to the life-specific of menstrual cycle specific stage of the subject, e.g., about pH 4.5 to about 6.8 for menopausal female subjects; about pH 3.5 to about 5.5 for reproductive aged female subjects that are not in the ovulatory phase; or about pH 4.5 to about 6.5 for pregnant subjects. In some embodiments, xylose is in an amount ranging from about 0.02% to about 0.5% by weight and *Salvia* extract is at a concentration ranging from about 0.01% to about 0.2% by weight. In some embodiments, the *Salvia* extract is *Salvia sclarea*, *Salvia hispanica*, *Salvia plebeia*, or combinations thereof.

The freshening compositions may further comprise a non-irritating viscosity increasing agent at a concentration ranging from about 0.1% to about 25% by weight. In certain embodiments, the non-irritating viscosity-increasing agent is a cellulose ester (e.g., methylcellulose, ethylcellulose, ethyl methyl cellulose, hydroxyethyl cellulose, hydroxypropyl cellulose, hydroxyethyl methyl cellulose, hyroxypropyl methyl cellulose (hypromellose), ethyl hydroxyethyl cellulose, carboxymethyl cellulose), carbomer, polyoxazoline, or any combination thereof. In some embodiments, the non-irritating viscosity-increasing agent is a carbomer, such as homopolymer type B at a total concentration ranging from about 0.1% to about 3% by weight. In some embodiments, the non-irritating viscosity-increasing agent is a polyoxazoline, such as poly(2-methyl-2-oxazoline) at a total concentration ranging from about 5% to about 10%.

The freshening compositions may further comprise a surfactant at a total concentration ranging from about 0.25% to about 10% by weight. In certain embodiments, the surfactant is cetyl hydroxyethylcellulose, polyvinyl alcohol, or both. In some embodiments, the surfactant is a cetyl hydroxyethylcellulose at a total concentration ranging from about 0.25% to about 5% by weight. In other embodiments, the surfactant is a polyvinyl alcohol at a total concentration ranging from about 1% to about 3% by weight. The freshening compositions may also include a paraben-free preservative at a total concentration ranging from about 0.005% to 5% by weight. In certain embodiments, the paraben-free preservative is a phenethyl alcohol, caprylyl glycol, oleuropein, acemannan, carvacrol, an ascorbate, cranberry extract, or any combination thereof. In some embodiments, the paraben-free preservative is a phenethyl alcohol and caprylyl glycol together at a total concentration ranging from about 0.02% to about 1.5% by weight. In other embodiments, the paraben-free preservative is a phenethyl alcohol, caprylyl glycol and a sodium ascorbate, together at a total concentration ranging from about 0.5% to about 2% by weight. In yet other embodiments, the paraben-free preservative is a cranberry extract at a total concentration ranging from about 0.01% to about 2.5% by weight.

The freshening compositions may further comprise a buffering agent at a total concentration ranging from about 0.05% to about 2.5% by weight. In certain embodiments, the buffering agent is lactic acid, sodium lactate, ascorbic acid, sodium ascorbate, sodium phosphate, acetic acid, sodium acetate, citric acid, or any combination thereof. In some embodiments, the buffering agent is lactic acid and sodium lactate together at a total concentration ranging from about 0.4% to about 1% by weight. In other embodiments, the buffering agent is ascorbic acid and sodium ascorbate at a total concentration ranging from about 0.5% to about 2% by weight.

The freshening compositions may also comprise an osmolality adjuster, such as sodium chloride, potassium chloride, or both, at a total concentration ranging from about 0.1% to about 1% by weight.

The freshening compositions may further comprise at least one pH modifying agent, such as an acidifying agent, an alkalizing agent, or both, at a total concentration ranging from about 0.001% to about 2% by weight. In some embodiments, the alkalizing agent is ammonia, ammonium carbonate, diethanolamine, monoethanolamine, potassium hydroxide, potassium phosphate dibasic, sodium bicarbonate, sodium borate, sodium carbonate, sodium hydroxide, sodium lactate, sodium phosphate dibasic, trolamine, or any combination thereof. In a specific embodiment, the alkalizing agent is sodium hydroxide at a total concentration ranging from about 0.01% to about 1% by weight.

The freshening compositions may also comprise a solvent. In a specific embodiment, the solvent is water and the composition comprises from about 90% to about 99% water.

An exemplary topical, isotonic, biome-friendly freshening composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is poly(2-methyl-2-oxazoline) at a total concentration ranging from about 1% to about 10% by weight; a surfactant, wherein the surfactant is polyvinyl alcohol and cetyl hydroxyethylcellulose together at a total concentration ranging from about 1% to about 9% by weight; a buffering agent, wherein the buffering agent is lactic acid and sodium lactate together at a total concentration ranging from about 0.5% to about 1% by weight; an osmolality adjuster, wherein the osmolality adjuster is sodium chloride at a total concentration ranging from about 0.1% to about 0.7% by weight; a pH modifier, wherein the pH modifier is sodium hydroxide at a concentration ranging from about 0.001% to about 1% by weight; and a solvent, wherein the solvent is water at a concentration ranging from about 90% to about 98% by weight, and wherein the composition has a pH ranging from about 3.5 to about 6.8. The freshening composition can be formulated as a gel.

Another exemplary topical, isotonic, biome-friendly freshening composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is poly(2-methyl-2-oxazoline) at a total concentration ranging from about 5% to about 10% by weight; a buffering agent, wherein the buffering agent is lactic acid and sodium lactate together at a total concentration ranging from about 0.5% to about 1% by weight; an osmolality adjuster, wherein the osmolality adjuster is sodium chloride at a total concentration ranging from about 0.1% to about 0.7% by weight; a solvent, wherein the solvent is water at a concentration ranging from about 88% to about 98% by weight; a pH modifier, wherein the pH modifier is sodium hydroxide at a concentration ranging from about 0.001% to about 1%; and optionally, a paraben-free preservative, wherein the paraben-free preservative is preferably a phenethyl alcohol and caprylyl glycol together at a total concentration ranging from about 0.2% to about 0.7% by weight, and wherein the composition has a pH ranging from about 3.5 to about 6.8. The freshening composition can be formulated as a gel.

Yet another example of a topical, isotonic, biome-friendly freshening composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is carbomer homopolymer type B at a total concentration ranging from about 0.2% to about 3% by weight; a surfactant, wherein the surfactant is cetyl hydroxyethylcellulose at a total concentration ranging from about 0.5% to about 1.5% by weight; a buffering agent, wherein the buffering agent is lactic acid and sodium lactate together at a total concentration ranging from about 0.4% to about 1% by weight; an osmolality adjuster, wherein the osmolality adjuster is sodium chloride at a total concentration ranging from about 0.1% to about 0.7% by weight; a solvent, wherein the solvent is water at a concentration ranging from about 90% to about 98% by weight; a pH modifier, wherein the pH modifier is sodium hydroxide at a concentration ranging from about 0.001% to about 1% by weight; and optionally, a paraben-free preservative, wherein the paraben-free preservative is preferably a phenethyl alcohol and caprylyl glycol together at a total concentration ranging from about 0.2% to about 0.7% by weight, and wherein the composition has a pH ranging from about 3.5 to about 6.8. The freshening composition can be formulated as a gel.

Another exemplary topical, isotonic, biome-friendly freshening composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is carbomer homopolymer type B at a total concentration ranging from about 0.1% to about 3% by weight; a surfactant, wherein the surfactant is cetyl hydroxyethylcellulose at a total concentration ranging from about 0.5% to about 1.5% by weight; a buffering agent, wherein the buffering agent is ascorbic acid and sodium ascorbate together at a total concentration ranging from about 0.5% to about 1.2% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; and optionally, a paraben-free preservative, wherein the paraben-free preservative is preferably a phenethyl alcohol and caprylyl glycol together at a total concentration ranging from about 0.2% to about 0.7% by weight, and wherein the composition has a pH ranging from about 3.5 to about 6.8. The freshening composition can be formulated as a gel.

Yet another exemplary topical, isotonic, biome-friendly freshening composition comprises xylose at a concentration ranging from about 0.01% to about 2.5% by weight or about 0.02% to about 0.5% by weight and *Salvia sclarea* at a concentration ranging from about 0.025% to about 0.075% by weight, and the composition further comprises: a non-irritating viscosity-increasing agent, wherein the non-irritating viscosity-increasing agent is carbomer homopolymer type B at a total concentration ranging from about 1% to about 3% by weight; a surfactant, wherein the surfactant is polyvinyl alcohol at a total concentration ranging from about 1% to about 3% by weight; a buffering agent, wherein the buffering agent is lactic acid and sodium lactate together at a total concentration ranging from about 0.5% to about 1% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; and a pH modifier, wherein the pH modifier is sodium hydroxide at a concentration ranging from about 0.001% to about 1% by weight, and wherein the composition has a pH ranging from about 3.5 to about 6.8. The freshening composition can be formulated as a gel.

Another exemplary topical, isotonic, biome-friendly freshening composition comprises xylose at a concentration ranging from about 0.01% to about 2.5% by weight or about 0.02% to about 0.5% by weight and *Salvia plebeia* at a concentration ranging from about 0.025% to about 0.25% by weight, and the composition further comprises: a non-irritating viscosity-increasing agent, wherein the non-irritating viscosity-increasing agent is poly(2-methyl-2-oxazoline) at a total concentration ranging from about 5% to about 17% by weight; an osmolality adjuster, wherein the osmolality adjuster is sodium chloride at a total concentration ranging from about 0.1% to about 0.7% by weight; a solvent, wherein the solvent is water at a concentration ranging from about 80% to about 95% by weight; and a pH modifier, wherein the pH modifier is sodium hydroxide at a concentration ranging from about 0.001% to about 1% by weight, and optionally, a paraben-free preservative, wherein the paraben-free preservative is preferably cranberry extract at a total concentration from about 0.01% to about 0.5%, wherein the composition has a pH ranging from about 3.5 to about 6.8. The freshening composition can be formulated as a gel.

Another exemplary topical, isotonic, biome-friendly freshening composition comprises xylose at a concentration ranging from about 0.01% to about 2.5% by weight or about 0.02% to about 0.5% by weight and *Salvia plebeia* at a concentration ranging from about 0.025% to about 0.25% by weight, and the composition further comprises: a non-irritating viscosity-increasing agent, wherein the non-irritating viscosity-increasing agent is hypromellose and carbomer homopolymer type B together at a total concentration ranging from about 1.0% to about 2% by weight, and wherein the ratio of hypromellose to carbomer homopolymer type B in the composition is about 4.5:1; a surfactant, wherein the surfactant is polyvinyl alcohol at a total concentration ranging from about 0.8% to about 3% by weight; a buffering agent, wherein the buffering agent is monobasic sodium phosphate and sodium citrate at a total concentration ranging from about 0.5% to about 1.5% by weight; an osmolality adjuster, wherein the osmolality adjuster is sodium chloride at a total concentration ranging from about 0.1% to about 0.7% by weight; a solvent, wherein the solvent is water at a concentration ranging from about 95% to about 98% by weight; and optionally, a paraben-free preservative, wherein the paraben-free preservative is preferably caprylyl glycol at a total concentration from about 0.1% to about 0.5%, wherein the composition has a pH ranging from about 3.5 to about 6.8. The freshening composition can be formulated as a gel.

(6) Vaginal Tightening Compositions

In yet another aspect of the present disclosure, vaginal tightening compositions are provided. Compositions (e.g., gels) that create a sensation of greater friction during intercourse are desired by many women and couples, especially after childbirth and aging. In addition, several cultures perceive a benefit of "dry sex" with minimal lubrication of the vaginal canal. Common ingredients in available products for tightening the vagina contain highly drying and irritating compounds, including talc, alum, and witch hazel. Many women "wash" the vagina out prior to intercourse with water and washcloths to reduce normal arousal fluids and perceived "excess" lubrication. These compounds and practices dry and increase microtrauma in the vaginal vault, which can increase STD transmission risks. The vaginal tightening compositions (e.g., bioadhesive vaginal gels or films) provided herein create a sense of greater friction in the vagina. The vaginal tightening compositions coat and protect the vagina, but also allow for the sensation of friction during intercourse.

The vaginal tightening compositions are pH matched to the vulvar and vaginal pH of the subject, e.g., for a reproductive aged woman (about pH 3.5 to about 5.5), an ovulatory phase woman (about 6.8 to about 7.8), pregnant woman (about pH 4.5 to about 6.5), or postmenopausal woman (around about 4.0 to about 6.8). In certain embodiments, the vaginal tightening compositions comprise a poly (2-oxazoline). Thus, for example, any of the LRT compositions disclosed herein that further comprise poly(2-oxazoline) may be used as vaginal tightening compositions. A poly(2-oxazoline) may be poly(2-alkyl-2-oxazoline) or poly(2-aryl-2-oxazoline), or both. In some embodiments, a poly(2-alkyl-2-oxazoline) may be poly(2-methyl-2-oxazoline), poly(2-ethyl-2-oxazoline), poly(2-isopropyl-2-oxazoline), or any combination thereof. In some embodiments, a poly(2-aryl-2-oxazoline) is poly(2-phenyl-2-oxazoline). Poly(2-oxazoline) is a low viscosity, hydrophilic, biocompatible polymer that provides firm bioadhesion to the vaginal wall, thereby protecting the LRT from micro trauma, while at the same time providing friction of the penis against the bioadhesive coating.

Vaginal tightening compositions of the present disclosure can be formulated as a semi-solid, gel, ointment, liquid, lotion, jelly, film, suspension, emulsion, mucilage, foam, cream, paste, or aerosol.

Vaginal tightening compositions of the present disclosure can be used for perineal massage, contraception, anti-microbial, fertility enhancement, sexual lubrication, vaginal hydration, sexual arousal, vaginal tightening, vaginal freshening, vaginal homeostasis, as a drug carrier base, or any combination thereof.

In certain embodiments, the vaginal tightening compositions are used in methods for increasing friction during sexual intercourse, comprising administering the vaginal tightening composition intravaginally, to the penis, to condoms, or to other devices (e.g., sex toys). In some embodiments, the vaginal tightening composition is administered within 24 hours, 12 hours, 6 hours, 2 hours, 1 hour, 30 minutes, 15 minutes, 5 minutes, just prior to, or during sexual intercourse.

Exemplary formulations of vaginal tightening compositions and % ranges of each component as contemplated in the present disclosure are set forth as follows.

Vaginal tightening composition formula 1 comprises: 89.1% by weight purified water; 0.1% by weight *Salvia plebeia*; 0.406% by weight phenethyl alcohol; 0.294% by weight caprylyl glycol; 0.5% by weight sodium chloride; 0.4% by weight xylose; 9.1% by weight poly(2-methyl-oxazoline) 25 kDa; 0.01% by weight sodium hydroxide. In certain embodiments, vaginal tightening composition formula A is formulated as a gel.

Vaginal tightening composition formula 2 comprises: 83.5% by weight purified water; 0.1% by weight *Salvia plebeia*; 0.406% by weight phenethyl alcohol; 0.294% by weight caprylyl glycol; 0.5% by weight sodium chloride; 0.4% by weight xylose; 14.7% by weight poly(2-ethyl-2-oxazoline) 70 kDa; 0.01% by weight sodium hydroxide. In certain embodiments, vaginal tightening composition formula B is formulated as a gel.

(7) Drug Carrier Base Compositions

In yet another aspect of the present disclosure, the compositions provided herein (e.g., fertility compositions, contraceptive compositions, perineal massage compositions, menopause compositions, freshening compositions) may be used as a drug carrier base. For example, the compositions may be combined with over the counter or prescription drugs to treat medical conditions of the female lower reproductive tract. Common topical yeast treatments include 5 or 6 inactive ingredients that compromise LRT homeostasis and function. The irritation and burning that accompany these yeast infection treatments can actually lead to more LRT pathology and symptoms. The same is true for hormone replacement therapy medications and a variety of other "therapies." For example, a leading vaginal estrogen product contains cornstarch as a primary ingredient, which causes irritation in many women, as well as an unsightly white discharge.

The drug carrier base compositions of the present disclosure preserve LRT homeostasis, and the "inactive" ingredients in the composition are truly inactive. Drug carrier base compositions of the present disclosure can be formulated as a semi-solid, gel, ointment, liquid, lotion, jelly, film, suspension, emulsion, mucilage, foam, cream, paste, or aerosol. In certain embodiments, the drug carrier base compositions are formulated as a bioadhesive formulation (e.g., gel or film) so that the medication dose is retained inside the vagina, reducing loss of dosing and mess for female subject.

Drug carrier base compositions of the present disclosure can be used for perineal massage, contraception, anti-microbial, fertility enhancement, sexual lubrication, vaginal hydration, sexual arousal, vaginal tightening, vaginal freshening, vaginal homeostasis, as a drug carrier base, or any combination thereof.

Examples of conditions that may be treated include yeast infections, bacterial infections, viral infections, hormone imbalances, infertility, and menopausal symptoms. In certain embodiments, the compositions of the present disclosure may be a drug carrier base for a topical pain relieving agent (topical analgesic), an anti-microbial (e.g., antibiotic, anti-viral agent, anti-fungal agent, or a combination thereof), an agent for treating or preventing a hormone imbalance, or an agent for treating or preventing infertility, or a combination thereof.

In certain embodiments, a topical pain relieving agent that is contained in a drug carrier base composition is lidocaine, benzocaine, novocaine, diphenhydramine, or pramoxine.

In certain embodiments, an anti-microbial agent is an anti-fungal agent selected from butoconazole nitrate, clotrimazole, miconazole nitrate, terconazole, tioconazole, econazole nitrate, efinaconazole, ketoconazole, luliconazole, naftifine hydrochloride, oxiconazole nitrate, sertaconazole nitrate, sulconazole nitrate, tavaborole, terbinafine, acyclovir, tenovir, zidovudine, stavudine, metronidazole, or a combination thereof.

Other examples of therapeutic agents include hormones (e.g., estradiol, estriol, estropipate, testosterone, progesterone, DHEA or a combination thereof), contraceptive agents (e.g., that impair sperm function, thicken cervical mucus, or both), growth factors (e.g., vascular endothelial growth factor), and vasodilators (e.g., L-arginine, niacin, nicotinamide, alprostadil, phosphodiesterase inhibitor).

In certain embodiments, the compositions disclosed herein (e.g., fertility compositions, contraceptive compositions, perineal massage compositions, menopause compositions, freshening compositions) further comprise factors that maintain, improve, or enhance VMB (e.g., Lactobacilli) function and health, such as amylase, glycogen, D-lactic acid, L-lactic acid, a prebiotic (e.g., acemannan or galactoarabinan), or a combination thereof.

In certain embodiments, the compositions disclosed herein further comprise at least one vaginal probiotic bacterial species or strain (e.g., *Lactobacillus* species).

B. In Vitro and In Vivo Activity (1) Sperm Function Assays

Formulations and compositions of this disclosure can be evaluated for their effect on sperm survival and function through the use of assays or models known in the art, such as sperm motility assays (e.g., subjective or computer assisted), sperm viability studies, in vitro fertilization and embryo development animal models, membrane integrity of sperm, survival time in culture, cervical mucus penetration, lipid peroxidation, capacitation, zona recognition, acrosome reaction and sperm-oocyte fusion, and sperm chromatin testing (reviewed in, e.g., Vasan, *Indian J. Urol.* 27:41, 2011; Oehninger et al., *Fertil. Steril.* 102:1528, 2014; Mortimer et al., 2013, Hum. Reprod. Update 19 (Suppl 1):i1-i45). Additional testing can include post-coital testing to evaluate sperm presence in the cervical canal, and even pregnancy outcomes in an animal model or among women in a clinical trial.

Sperm motility is one function that may be used to assess sperm function and thus fertilization potential. Motility of sperm is expressed as the total percent of motile sperm, the total percent of progressively motile sperm (swimming forward), or the speed of sperm that are progressively motile. These measurements may be made by a variety of assays, but are conveniently assayed in one of two ways. Either a subjective visual determination is made using a phase contrast microscope when the sperm are placed in a hemocytometer or on a microscope slide, or a computer assisted semen analyzer is used. Under phase contrast microscopy, motile and total sperm counts are made and speed is assessed as fast, medium or slow. A more specific of sperm motility is motility grade, where the motility of sperm is divided into four different grades (Cooper et al., 2010, Human Reprod. Update 16:231-45). Grade A refers to sperm with progressive motility that are the strongest and swim fastest in a straight line. Grade B refers to sperm with non-linear motility; that move forward but tend to travel in a more curved or crooked motion. Grade C sperm have non-progressive motility in that they do not move forward despite tail movement. Grade D sperm are immotile. Using a computer assisted semen analyzer (such as IVOS Hamilton Thorne, Beverly, Mass.), the motility characteristics of individual sperm cells in a sample are objectively determined (1998, Hum. Reprod. 13:142-5). Briefly, a sperm sample is placed onto a slide or chamber designed for the analyzer. The analyzer tracks individual sperm cells and determines motility and velocity of the sperm. Data is expressed as percent motile, and measurements are obtained for path velocity and track speed as well.

Sperm viability can be measured using several different methods. By way of example, two of these methods are staining with membrane exclusion stains and measurement of ATP levels. Briefly, a sample of sperm is incubated with a viable dye, such as Hoechst 33258 or eosin-nigrosin stain. Cells are placed in a hemocytometer and examined microscopically. Dead sperm with disrupted membranes stain with these dyes. The number of cells that are unstained is divided by the total number of cells counted to give the percent live cells. ATP levels in a sperm sample are measured by lysing the sperm and incubating the lysate with luciferase, an enzyme obtained from fireflies, which fluoresces in the presence of ATP. The fluorescence is measured in a luminometer. The amount of fluorescence in the sample is compared to the amount of fluorescence in a standard curve allowing a determination of the number of live sperm present in the sample. Membrane integrity of sperm is typically assayed by a hypo-osmotic swell test which measures the ability of sperm to pump water or salts if exposed to non-isotonic environments. Briefly, in the hypo-osmotic swell test, sperm are suspended in a solution of 75 mM fructose and 25 mM sodium citrate, which is a hypo-osmotic (150 mOsm) solution. Sperm with intact, healthy membranes pump salt out of the cell causing the membranes to shrink as the cell grows smaller. The sperm tail curls inside this tighter membrane. Thus, sperm with curled tail are counted as live, healthy sperm with normal membranes. When compared to the total number of sperm present, a percent of functional sperm may be established.

The degree of membrane integrity is preferably determined by lipid peroxidation (LPO) measurements, which assess sperm membrane damage generated by free radicals released during handling. Lipid membrane peroxidation is assayed by incubating sperm with ferrous sulfate and ascorbic acid for one hour in a 37° C. water bath. Proteins are precipitated with ice-cold trichloroacetic acid. The supernatant is collected by centrifugation and reacted by boiling with thiobarbituric acid and NaOH. The resultant malondialdehyde (MDA) formation is quantified by measuring absorbance at 534 nm as compared to an MDA standard (Bell et al., *J. Andrology* 14:472-478, 1993). LPO is expressed as nM MDA/$10^8$ sperm. A composition disclosed herein has a stabilizing effect on sperm if exposure results in decreased LPO production.

The stability of chromatin DNA is assayed using the sperm chromatin structure assay (SCSA). Sperm cells are very sensitive to oxidative stress resulting in sperm chromatin (DNA) damage (Whittington et al., 1999, Int. J. Andrology 22:236-242; Pasqualotto et al., 2000, Fertility and Sterility 73:459-464; Kodama et al., 1997, Fertility and Sterility 68:519-524). This damage can be profound in sperm cells because they contain little to no mechanisms to repair DNA damage after it occurs. Substantial scientific data over the last decade has shown that sperm chromatin damage can result in severe disruptions in fertility and adverse consequences for offspring (World Health Organization. WHO Laboratory Manual for the Examination and Processing of Human Semen. $5^{th}$ ed. Switzerland: World Health Organization, 2010). This assay is based on the metachromatic staining of single and double stranded DNA by acridine orange stain (Evenson et al., 1999, Human Reprod. 14:1039-1049; Evenson et al., 2002, J. Andrology 23:25-43). Excitation with an argon laser causes acridine orange intercalated in double-stranded DNA to emit a green fluorescence, whereas red fluorescence is emitted by single strand DNA. The extent of DNA denaturation in a sample is expressed as a and calculated by the formula $\alpha=red/(red+green)$. The endpoint measurement is DNA Fragmentation Index (DFI). A DFI of <15% DFI indicates excellent to good sperm DNA integrity. Fresh sperm samples are incubated for a period of time in the presence of a test composition, flash frozen, and subsequently assayed for DNA breakage (see, e.g., Evenson et al., 2002., J. Androl. 23:25-43).

In vitro fertilization rates are determined by measuring the percent fertilization of oocytes in vitro in an animal model such as bovine or murine model. For example, maturing bovine oocytes are cultured in vitro in M199 medium plus 7.5% fetal calf serum and 50 µg/ml luteinizing hormone for 22 hours. Following culture for 4 hours, the sperm are chemically capacitated by adding 10 IU of heparin and incubated with bovine oocytes for 24 hours. At the end of the incubation, oocytes are stained with an aceto-orcein stain or equivalent to determine the percent oocytes fertilized. Alternatively, fertilized oocytes may be left in culture for 2 days, during which division occurs and the number of cleaving embryos (i.e., 2 or more cells) is counted.

Survival time in culture of sperm (time to loss of motility) is another convenient method of establishing sperm function. This parameter correlates well with actual fertility of a given male. Briefly, an aliquot of sperm is placed in culture medium, such as Tyrode's medium, pH 7.4 and incubated at 37° C., 5% $CO_2$, in a humidified atmosphere. At timed intervals, for example every 2 hours, the percentage of motile sperm in the culture is determined by visual analysis using an inverted microscope or with a computer assisted sperm analyzer. As an endpoint, a sperm sample is considered no longer viable when less than 5% of the cells have progressive motility.

Another parameter of sperm function is the ability to of sperm to swim up into a column of cervical mucus or substitute (reviewed in Ola et al., *Hum. Reprod.* 18:1037-1046, 2003). This cervical mucus penetration test can be done either in vitro or in vivo. Sperm are placed at one end of the track and the distance that sperm have penetrated into the mucus after a given time period is determined. Cervical mucus penetration studies offer valuable biocompatibility data for devices that are used for reproductive purposes. The bovine cervical mucus penetration study is an excellent in vitro assay to evaluate sperm penetration into cervical mucus. Bergman et al. (1981, Fertility and Sterility 36:363-367) found excellent correlation between sperm penetration into frozen bovine cervical mucus and fresh human cervical mucus (r=0.98) due to the similarity of human and bovine cervical mucus rheological and biophysical make-up (Bergman et al., *Fertil. Steril.* 36:363-367, 1981; Keel et al., *Arch. Androl.* 44:109-115, 2000). Human cervical mucus is produced in small volumes, has variable quality in a clinical setting, and is difficult to access. In cattle, large quantities of estrus mucus are produced, making access straightforward. Additionally, cows are selected for high fertility, so cervical mucus quality is more consistent. Mucus from several cows can be pooled, frozen, and subsequently used across an entire experiment, thereby decreasing variability in the assay. De Geyter et al. (*Hum. Reprod.* 3:948-954, 1988) found better correlation between human IVF outcomes and sperm penetration in bovine cervical mucus as compared to human cervical mucus, using the endpoints of vanguard sperm penetration and sperm density at fixed distances. Sharara et al. (1995, Human Reproduction 10:1481-1485) found that sperm penetration into human or bovine cervical mucus correlated with IVF outcomes at a similar rate (r=0.66). Keel and Schalue (*Arch. Androl.* 44:109-115, 2000) performed a large experiment with 1,400 human ejaculates to observe the relationship between ejaculate quality and bovine cervical mucus penetration test (BCMPT) outcomes. They found that sperm motility correlated well with penetration in the BCMPT (r=0.448) in a linear relationship. However, approximately 30% of the samples with normal semen characteristics had abnormal BCMPT. This indicated that the BCMPT was evaluating something unique that sperm motion characteristics alone could not detect (Sharara et al., Hum. Reprod. 10:1481-1485, 1995). Also, cryopreserved bull sperm with higher pregnancy rates in cows had a higher penetration rate into bovine cervical mucus than sperm from less fertile bulls (Tas et al., Anim. Reprod. Sci. 101:18-27, 2007).

Alternatively, sperm penetration of mucus may be measured in vivo in women. At various times post-coitus, a sample of cervical mucus is removed and examined microscopically for the number of sperm present in the sample. In the post-coital test, improved sperm function is established if more sperm with faster velocity are seen in the mucus sample after exposure to a composition of the present disclosure versus a sample of mucus from the patient after exposure to a control lubricant.

Other assays of sperm function potential include the sperm penetration and hemizona assays. In the sperm penetration assay, the ability of sperm to penetrate into an oocyte is measured. Briefly, commercially available zona free hamster oocytes are used (EmbryoTech Laboratories, Haverhill, Mass.). Hamster oocytes are suitable in this assay for sperm of any species. Capacitated sperm, such as those cultured with bovine serum albumin for 18 hours, are incubated for 3 hours with the hamster oocytes. Following incubation, oocytes are stained with acetolacmoid or equivalent stain and the number of sperm penetrating each oocyte is counted microscopically. A hemizona assay measures the ability of sperm to undergo capacitation and bind to an oocyte. Briefly, in this assay, live normal sperm are incubated in media with bovine serum albumin, which triggers capacitation. Sperm are then incubated with dead oocytes which are surrounded by the zona pellucida, an acellular coating of oocytes. Capacitated sperm bind to the zona and the number of sperm binding is counted microscopically.

In certain embodiments, a composition of the present disclosure are non-toxic to sperm if following exposure to a 10% solution of the composition, sperm retain at least 80% motility as compared to sperm exposed to a control medium.

(2) Evaluating Oocyte or Embryo Quality

Compositions of the present disclosure may be evaluated for their effect on oocyte survival and function using a variety of methods known in the art. The effect of a test composition on oocyte quality may be determined using an oocyte expansion assay. The mammalian pre-ovulatory follicle contains a mature oocyte that is enclosed by the somatic cumulus cells forming the cumulus cell-oocyte complex (COC). Within this complex, the cumulus cells are tightly connected to each other and to the oocyte via cell adhesion complexes and gap junctions. In response to the ovulatory luteinizing hormone (LH) surge, cumulus cells expand and produce a complex extracellular matrix, which is essential for ovulation, fertilization, and subsequent embryonic development. This highly coordinated process is called "cumulus expansion." An in vitro cumulus expansion assay tests the ability of mouse oocytes to expand following exposure to a composition. For example, mouse oocytes are incubated in medium with or without 50 µg/ml luteinizing hormone for 22 hours. Normal oocytes will have >3-5 layers of expanded cumulus. Normal cumulus cell expansion is required for oocytes maturation and fertilization.

The effect of a test composition on oocyte quality may also be assessed by oocyte maturation status. Staining techniques for staging nuclear maturation of oocytes include 1% aceto-orcein staining and anti-lamin A/C and 4',6-diamidino-2-phenylindole technique, which may be used to determine the percentage of oocytes that progress to metaphase II stage following exposure to a test composition. Oocytes entering metaphase II stage have completed meiosis 1 to become a haploid oocyte and commenced meiosis 2, arresting at metaphase until fertilization occurs. Only oocytes that are in the metaphase II stage are capable of being fertilized.

The effect of a composition disclosed herein on embryonic quality may be determined using morphological evaluations in an animal model (e.g., bovine, rodent), including observing for normal cleavage or divisional of the embryo in culture (Lindner and Wright, Theriogenology 20:407, 1983); normal formation of a blastocysts cavity at an appropriate time in culture; counting the number and health of cells found in the embryo using Hoeschst 33342 stain (Pursel et al., Theriogenology 24:687); establishment of pregnancy following transfer to a female subject; birth of a normal offspring following transfer to a female subject.

A mouse embryo assay (MEA) is a common system to assess toxicity of materials used in assisted reproductive techniques. In brief, a one-cell embryo is obtained and exposed to a 10% solution of the test composition diluted in M2 mouse embryo culture media for a period of time (e.g., 30 minutes). The embryos are then transferred to appropriate culture medium and cultured for 96 hours. The number 1-cell embryos that transitioned to 2-cell embryos within 24 hours and the number of 1-cell embryos that transitioned to expanded blastocyst stage within 96 hours (blastocyst rate) are also determined. In certain embodiments, a test composition is non-toxic to embryos if the blastocyst rate of the group exposed to the test composition is at least 80% of the blastocyst rate of the control group within 96 hours following exposure to the test composition.

(3) Evaluating Vaginal Flora

The vaginal microbiota (VMB) is a key component of regulating LRT homeostasis. Demonstration that a topical product administered to the LRT does not significantly harm *Lactobacillus* colonies and related beneficial organisms is critical to maintaining or enhancing LRT function. To assess the impact of a topical composition on the VMB, testing of normal vaginal flora is performed using methods known in the art.

The effect of any composition disclosed herein on vaginal microbiota (e.g., *Lactobacillus* species) may be determined using the minimal microbicidal concentration method (MMC), the concentration required to reduce the viability of a culture by 99.99%, as described in Dezzutti et al. (*PLoS One* 7:e48328, 2012). Briefly, *Lactobacillus* suspensions are prepared by selecting isolated colonies from fresh overnight culture plates and suspending the test organisms in saline to a cell density of $2\times10^8$ bacteria/ml. Test and control compositions are mixed with an equal volume of the bacterial suspensions at room temperature and plated for colony forming units (CFUs). The number of CFUs is taken from the dilution plate containing 50 to 300 colonies. Samples are taken at time 0 and various time points post-exposure. Samples yielding 10 or fewer CFUs (representing a 99.99% kill) are considered sensitive to killing. All results are compared to the control (positive or negative), which have the same excipient vehicle but lack the active ingredients of the test composition(s) or contain a known microbicide in the same excipient vehicle. In vitro methods of testing the effects of compositions on planktonic *Lactobacillus* growth, vaginal epithelial cell viability, *Lactobacillus*-vaginal epithelial cell interactions have been described in Fashemi et al. (2013, Microb. Ecol. Health Dis. 24:19703).

Other methods that may be used to assess changes in vaginal microbiota following exposure to a LRT composition of this disclosure include 16S rRNA gene sequencing (see, e.g., Romero et al., Microbiome 2:4, 2014; Macklaim et al., *Microb. Ecol. Health Dis.* 26:27799, 2015), species specific quantitative PCR (Zozaya-Hinchliffe et al., *J. Clin. Microbiol.* 48:1812, 2010), and phylogenetic microarrays (Paliy and Agans, *FEMS Microbiol. Ecol.* 79:2, 2012).

In certain embodiments, the compositions of the present disclosure reduce normal vaginal microbiota population (e.g., *L. crispatus, L. gassseri, L. jensenii, L. acidophilus*, or any combination thereof) by no more than about 35%, about 30%, about 25%, about 20%, about 15%, about 10%, or about 5% when exposed to a concentration of the composition that is to be used in vivo on a female subject. In further embodiments, compositions of the present disclosure do not reduce normal vaginal microbiota of a female subject by more than about 35%, about 30%, about 25%, about 20%, about 15%, about 10%, or about 5% when an effective amount of a composition of this disclosure is used to contact the LRT of a female subject, wherein the amount of the composition used to contact the LRT of a female subject causes less than a $1\times\log_{10}$ reduction in growth of about one to about five *Lactobacillus* species in the minimal microbicidal concentration (MMC) assay of Dezzutti et al. (2012). In other embodiments, compositions of the present disclosure do not reduce the vaginal microbiota of a female subject more than about 35%, about 30%, about 25%, about 20%, about 15%, about 10%, or about 5% following administration of an effective amount of the composition to the lower reproductive tract as compared to the vaginal microbiota of the female subject prior to administration of the composition, wherein a species specific quantitative PCR measure of about one to about five *Lactobacillus* species present in the vaginal microbiota of the subject before and after contact with a composition of this disclosure is determined by the method of Zozaya-Hinchliffe et al. (2010).

(4) Irritation and Inflammation Assessment

The irritation and inflammation can be assessed in vitro or in vivo using human or animal vaginal-ectocervical tissue explants; vaginal, cervical or vulvar cell monolayers; skin cell monolayers; slug mucosal irritation assays; sperm toxicity assays; or other equivalent methods.

For example, the slug mucosal irritation assay (SMI) is a sensitive system to detect even mild mucosal irritation potency (Adriaens et al., *Sex. Transm. Dis.* 35:512, 2008). The SMI assay uses slugs (*Arlon lusitanicus*) as the test organism. The body wall of slugs consists of a mucosal surface comprising mucus secreting cells covering a subepithelial connective tissue. Slugs that are placed on an irritant substance will actively produce mucus as a protective mechanism from noxious agents. Additionally, tissue damage of the slug's surface results in the release of proteins and enzymes. The protein concentration in the collected samples is determined with a protein quantitation kit. A composition of this disclosure is considered non-irritating if it does not cause an increased production of mucus, or an increased release of proteins and enzymes as compared to a negative control.

Human, organotypic vaginal-ectocervical tissue model produced from normal human-derived vaginal-ectocervical epithelial cells may also be used to assess irritation of topically applied products, as can monolayers of cervical or vaginal epithelium (Ayehunie et al., *Toxicology* 279:130, 2011; Ayehunie et al., 2007, Toxicology 279:130-8; Trifonova et al., 2006, Antimicrob. Agents Chemother. 50:4005-4010; Fichorova et al., 2011, mBio 2:e00168-11). Release of markers of cell damage (e.g., increase in CD4, IL-1β (3, CXCL8, CCL2, CCL21, EMP1; decrease in BPI) and production of inflammatory mediators, such as IL-1, IL-8, TLR4, may be used as markers of irritation and pro-inflammation (see, also Fichorova et al., 2015, Toxicol. Appl. Pharmacol. 285:198-206; Doncel et al., 2004, J. Acquir. Immune Defic. Syndr. 37(Suppl. 3):S174-180; Fichorova et al., 2004, Biol. Reprod. 71:761-769; Moench et al., 2010, BMC Infect. Dis. 10:331). Biomarkers of epithelial integrity and immune function have been validated in multiple clinical studies of vaginal product safety (Mauck et al., 2013, AIDS Res. Hum. Retroviruses 29:1475-86; Fichorova et al., mBio, 2015, 6:e00221-15; Fichorova et al., 2011, Cytokine 55:134-140; Mauck et al., 2008, J. Acquir. Immune Defic. Syndr. 49:243-50; Morrison et al., 2014, J.

Acquir. Immune Defic. Syndr. 66:109-117; Schwartz et al., 2006, Contraception 74:133-40; Keller et al., 2003, J. Antimicr. Chemother. 51:1099-1102). A composition of this disclosure is considered non-irritating and non-inflammatory if it does not cause release of markers of cell damage or increased expression of pro-inflammatory mediators above that are caused by a negative control (e.g., synthetic TLR2/6 ligand).

Compositions as disclosed herein may also be tested for their effects in vaginal infection susceptibility models, such as a mouse genital herpes transmission model (see, e.g., Moench et al., 2010, BMC Infect. Dis. 10:331). Increased susceptibility to infection transmission may be caused by vaginal epithelial cell toxicities due to exposure to toxic excipients.

Effects of topical compositions on tissue viability using tissue models (e.g. human explants or cell monolayers) may also be assessed using the MTT colorimetric assay technique. The MTT assay is a colorimetric assay for assessing cell metabolic activity. NAD(P)H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. The MTT assay may be used to measure a composition's cytotoxicity or effect on cell viability (Ayehunie et al., 2011).

In addition, oxidative stress and antioxidant potential of the tissues can be determined by common methods, such as a TBARS assay to evaluate the impact of various embodiments on tissue health. Because reactive oxygen species (ROS) have extremely short half-lives, they are difficult to measure directly. Instead, several products of the damage produced by oxidative stress, such as thiobarbituric acid reactive substances (TBARS), can be measured. TBARS are formed as a byproduct of lipid peroxidation (i.e., as degradation products of fat), which can be detected by the TBARS assay using thiobarbituric acid as a reagent.

The in vivo rabbit vaginal irritation (RVI) model may also be used to assess the irritation and inflammatory characteristics of a formulation (Eckstein et al., J. Reprod. Fertil. 20:85, 1969). This model is based on macroscopic observations of erythema, edema and ulceration and histopathologic analysis of the tissues collected after exposure of the animals to the test materials. A non-irritating and safe composition of this disclosure would show no negative macroscopic or histopathologic effects as compared to a control vehicle. An expanded RVI model having a quantitative nuclease protection assay (qNPA) to quantify mRNA levels of 25 genes representing leukocyte differentiation markers, toll-like receptors (TLR), cytokines, chemokines, epithelial repair, microbicidal and vascular markers has also been described (see, Fichorova et al., 2015, Toxicol. Appl. Pharmacol. 285:198-206).

In another example, in vivo coloscopic exams of women following use of LRT compositions can be used to identify signs of inflammation or irritation. User surveys can also be used for scoring of symptoms of the same (Van Damme et al., Lancet 360:971, 2002; Bunge et al., J. Acquir. Immune Defic. Syndr. 60:337, 2012).

Sensitization tests may be used evaluate the potential of a composition of this disclosure to cause a sensitizing effect or allergenic reaction in a female subject over an extended period of exposure. Exemplary tests include Guinea pig tests, such as the Magnusson-Kligman guinea pig maximization test (J. Invest. Dermatol. 52:268, 1969), the occluded patch test of Buehler (Arch. Dermatol. 91:171, 1965), and the open epicutaneous test (Kero et al., Contact Dermatitis 6:341, 1980).

In yet another example, a murine local lymph node assay (LLNA) is another method for the identification of skin sensitizing chemicals. In contrast to guinea pig tests, this assay relies on measurement of events induced during the induction phase of skin sensitization, specifically lymphocyte proliferation in the draining lymph nodes which is a hallmark of a skin sensitization response, rather than the elicitation phase (Kimber et al., Contact Dermatitis 21:215, 1989; Basketter et al., Food Chem. Toxicol. 34: 985, 1996).

The human repeat-insult patch test (HRIPT) may be performed as a confirmatory test in the safety evaluation of skin sensitizers. Sensitization is a process by which humans develop increased allergic responses to a substance over time through repeated exposure to that substance. It is different from irritation because it involves an immune response. Skin sensitization reactions are usually characterized by erythema coupled with one or more of various dermal sequelae, such as edema, papules, vesicles, bullae, and/or pruritis (McNamee et al., Regul. Toxicol. Pharmacol. 52:24, 2008).

Irritating topical products may trigger the release of pro-inflammatory cytokines (e.g., TLR, IL-1, IL-6, IL-8, TNF-α, IFN-γ, IL-17) and inflammasomes (e.g., NLRP3 and NLRC4). Cytokines and inflammasomes can be measured using an enzyme-linked immunosorbent assay (ELISA), quantitative PCR, or other molecular assay. A product is considered non-inflammatory if it does not cause increased expression of pro-inflammatory cytokines or inflammasomes (Rabeony et al., Eur. J. Immunol. 45:2847, 2015).

In certain embodiments, the compositions of the present disclosure do not induce irritation or inflammation potential in the lower reproductive tract of a female subject greater than about 0.5%, about 1%, about 2.5%, about 5%, about 10%, about 15%, about 20%, about 25%, or about 30% as compared to an untreated control subject, preferably as measured using the slug test of Adriaens et al. (2008).

EXAMPLES

Example 1

Effect on Sperm Viability of Isotonic Composition of Salvia Extract

An isotonic, pH neutral (pH 7) solution comprising 10% Salvia hispanica (in oil format) was evaluated in a 24 hour sperm survival assay as previously described (see, Vargas et al., Fertil. Steril. 95:835, 2011). The isotonic solution comprising Salvia hispanica extract caused a significant decrease in levels of lipid peroxidation (LPO) damage as compared to that seen for sperm treated with control medium or with canola oil or almond oil (see Table 3). Oxidative stress results in lipid peroxidation of the sperm membrane, resulting in membrane dysfunction and impairment of sperm motility (Gil-Villa et al., Fertil. Sterol. 94:1465, 2010).

However, the isotonic solution comprising Salvia hispanica oil surprisingly caused significant sperm toxicity over the 24 hr incubation (FIG. 1). A Sperm Toxicity Index of <0.75 (meaning treated sperm survive on average less than 75% as compared to controls) is deemed as cytotoxic. The isotonic solution comprising Salvia hispanica oil exerted a profoundly significant (*p=0.0001) decrease in sperm motility over the sperm motility observed for control medium or with other natural plant products, i.e canola oil or almond oil, even though peroxidative damage to the sperm was mitigated with the *Salvia* (Table 3).

Taken together, these data suggest that *Salvia hispanica* has a toxic effect on sperm that is separate from any cellular oxidative damage, which would also trigger inflammation in the female LRT. This sperm toxicity effect may be useful in embodiments aimed at supporting homeostasis of the LRT during the non-ovulatory stage of a woman's cycle, when secretions are innately hostile to sperm function (e.g., contraceptive compositions).

TABLE 3

Lipid Peroxidation Levels in Sperm Post-Treatment

| Treatment | LPO products (ng/ml) |
| --- | --- |
| Control | 168 |
| *Salvia hispanica* Oil | 103* |
| Canola Oil | 150 |
| Almond Oil | 174 |

Example 2

Effect of *Salvia Sclarea* Extract on Mucosal Irritation Potential

Figure 2:
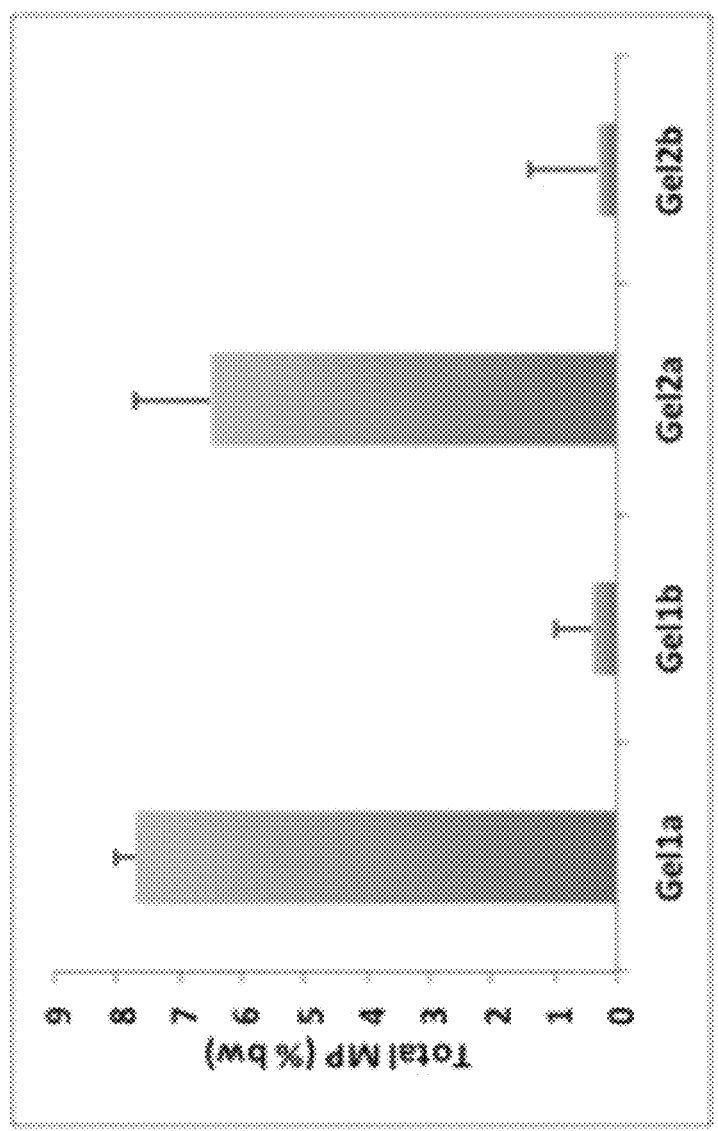
FIG. 2 is a bar graph depicting mucosal irritation potential as measured using slug mucosal irritation index for Fertility Gel 1a and Freshening Gel 2a, isotonic solutions containing xylose, as compared with Fertility Gel 1b (also referred to as Fertility Gel Formula AB) and Freshening Gel 2b (also referred to as Freshening Gel Formula AB), in which *Salvia sclarea* extract has been added.

The mucosal irritation potential of various embodiments of isotonic solutions that support LRT homeostasis was measured using a slug mucosal irritation (SMI) assay as described in Adriaens and Remon, 2008, Sex. Transm. Dis. 35:512-6. In brief, the SMI assay uses slugs (*Arlon lusitanicus*) as a test organism. The body wall of slugs comprises a mucosal surface including mucus secreting cells covering a sub-epithelial connective tissue. Slugs that are placed on an irritant substance will actively produce mucus as a protective mechanism from noxious agents. Additionally, tissue damage of the slug's surface results in the release of proteins and enzymes. The protein concentration in the collected samples is determined with a protein quantitation kit. A product is considered non-irritating if it does not cause increase production of mucus, and release of proteins and enzymes above that caused by a negative control. Fertility Gel 1a and Freshening Gel 2a are isotonic gels containing xylose. These both caused "mild" irritation as measured by SMI. Unexpectedly, adding a *Salvia sclarea* extract to each gel formulation helped decrease mucus production to make a "non-irritating" embodiments for Fertility Gel Formula AB (also referred to as Gel 1b) and Freshening Gel Formula AB (also referred to as Gel 2b) (FIG. 2).

Studies of Mucosal Irritation Potential in the Slug Mucosal Index (SMI), supports the methods and compositions disclosed herein for creating isotonic, non-irritating products that support LRT homeostasis.

Example 3 pH Balancing and Freshening Gel

An embodiment for a pH balancing and freshening composition is provided in herein as Freshening Gel Formula AB (also referred to as Gel 2b).

Figure 3:
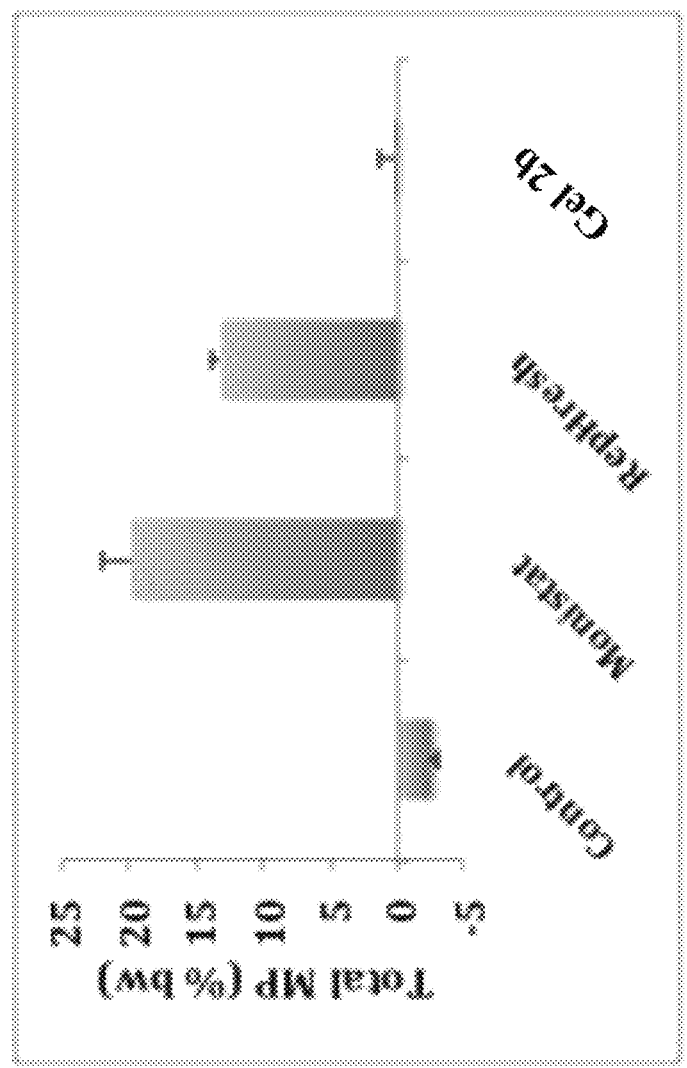
FIG. 3 is a bar graph depicting the mucosal irritation potential as measured by mucus production using the slug mucosal irritation index for Freshening Gel 2b, a pH balancing and freshening gel, as compared with MONISTAT™ and REPHRESH™.

Other freshening compositions, preferably formulated as a gel, that contain ingredients reported to be toxic to vaginal mucosal cells and vaginal microbiota caused moderate to severe irritation potential in the SMI (RepHresh and Monistat) (FIG. 3). Surprisingly, Freshening Gel 2b caused no mucosal irritation potential (FIG. 3), even though the isotonic product is pH matched to the low acidity of the non-ovulating vagina (i.e., pH 4.5). The control was an iso-osmotic, preservative-free hydroxyethylcellulose gel.

Figure 4:
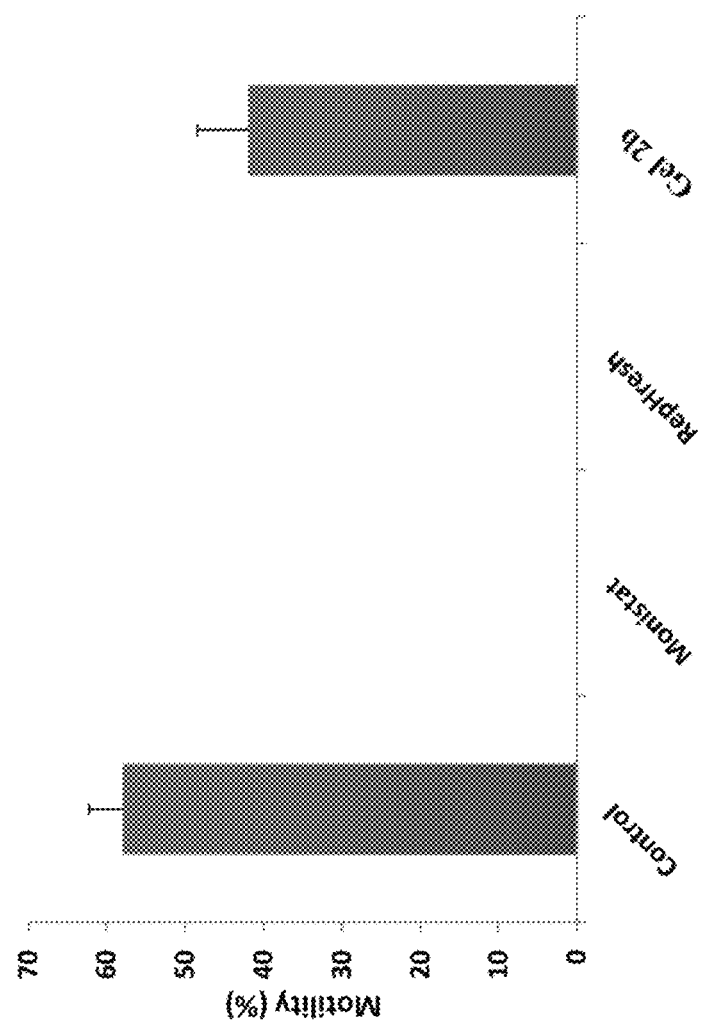
FIG. 4 is a bar graph depicting the effect of Freshening Gel 2b on sperm motility, as compared with MONISTAT™ and REPHRESH™.

Unexpectedly, the other products tested caused a complete loss of sperm motility on contact as measured by the toxicology screen, sperm survival assay (described in Vargas et al. Fertil. Steril., 2011, 95:835-6), whereas sperm motility was preserved on contact with the Gel 2b product (FIG. 4). The control in this experiment was buffered sperm culture medium.

Gel 2b is assayed for detrimental effects on vaginal microbiota species as compared with RepHresh® gel and MONISTAT®. *Lactobacillus* species that are indigenous to the healthy human vaginal microbiome (*L. crispatus, L. gasseri*, and *L. jensenii*) are incubated with Gel 2b, RepHresh®, or MONISTAT® to evaluate the effect of the gels on the vaginal microbes as described in Fashemi et al., 2013, Microbial Ecology in Health & Disease 24:19703. In brief, *Lactobacillus crispata* isolated from vaginal swab samples from healthy women is used to prepare bacterial suspensions. A bacterial suspension is incubated with 10% concentration of test composition for 24 hours, serially diluted, and plated on agar plates to obtain colony forming units. Control sample is incubated with media only. The gel formulations are also evaluated for effect on *G. vaginalis*, a bacterium that is implicated in the genesis of bacterial biofilms and bacterial vaginosis. The test gels are then ranked according to impact on *L. crispata* cfu.

Freshening Gel 2b undergoes safety evaluation using a human organotypic model (Ayehunie et al., *Toxicology* 279: 130, 2011; Klausner et al., 2007, Toxicology 279:130-8; Trifonova et al., 2006, Antimicrob. Agents Chemother. 50:4005-4010; Mauck et al., AIDS Res. Hum. Retroviruses, 2013, 29:1475-1486). A three-dimensional organotypic vaginal-ectocervical (VEC) tissue model is constructed in vitro using normal VEC epithelial cells and is well stratified, containing differentiated basal, suprabasal, intermediate, and superficial cell layers similar to in vivo tissue. The organotypic model is assessed following exposure to a test composition (Gel 2b, RepHresh®, or MONISTAT®) for signs of cytotoxicity or irritation as compared to a control sample comprising hydroxyethylcellulose). Biomarkers of cytotoxicity or irritation include: (1) decreased epithelial viability over a period of 24 hours; (2) decreased epithelium-associated *Lactobacillus* colony-forming units; (3) increased epithelial disruption biomarkers (e.g., IL-1α, IL-1β); (4) increased pro-inflammatory markers (e.g., ratio of IL-1(α+β) to IL-1RA; IL-8).

Example 4

Endotoxin Level of D-Xylose

Analysis of plant derived products found an unexpected high level of endotoxin in most Aloe Vera products. Many lubricants and other LRT products contain aloe vera, which could serve as an inflammatory trigger in LRT products. In contrast, xylose from a natural raspberry source (d-Xylose source 1) as used in the current embodiments has a very low endotoxin level, supporting LRT homeostasis (Table 4).

TABLE 4

Endotoxin Level of D-Xylose

| Product | Endotoxin Level |
|---|---|
| Aloe Vera Powder source 1 | 209 EU/mg |
| Aloe Vera Powder source 2 | 25 EU/mg |
| D-Xylose source 1 | <0.07 EU/mg |

Bacterial endotoxin levels in Fertility Gel 1b (Fertility Composition Formula AB) and Freshening Gel 2b (Freshening Composition Formula AB) were assessed following the protocol set forth in the United States Pharmacopeia and The National Formulary (USP-NF), Chapter 85. Bacterial endotoxin levels in Gel 1b and Gel 2b were demonstrated to be low (Table 5).

TABLE 5

Endotoxin Level of Exemplary Fertility Gel 1b and Freshness Gel 2b

| Test Gel | Endotoxin Level |
|---|---|
| Fertility Gel 1b | <1 EU/ml |
| Freshening Gel 2b | <1 EU/ml |

Example 5

Fertility Compositions

Figure 5:
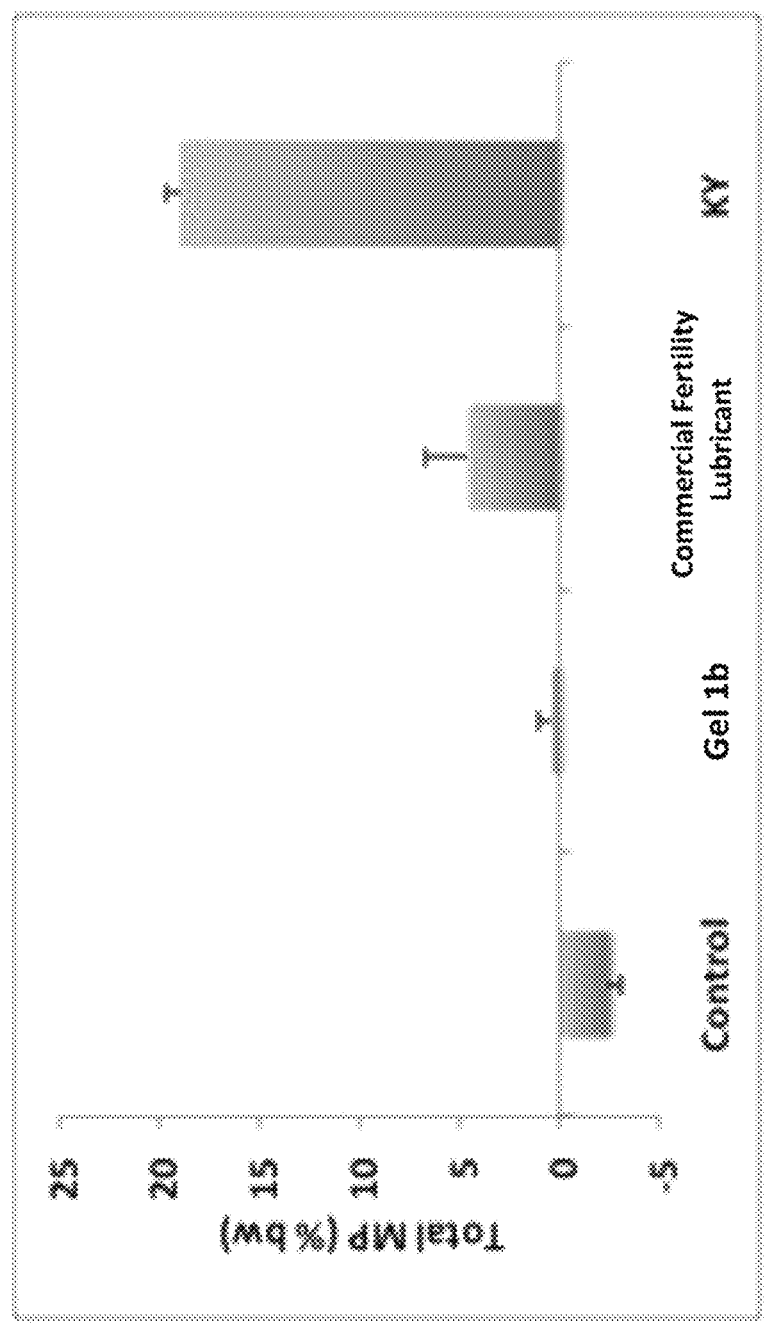
FIG. 5 is a bar graph depicting the mucosal irritation potential as measured using slug mucosal irritation index for Fertility Gel 1b, a formulation for enhanced sperm function during ovulatory stage of the female menstrual cycle as compared to a paraben-containing commercial fertility gel and KY Jelly®.

Products for enhanced sperm function and vaginal homeostasis during the ovulatory stage of the cycle are disclosed. An isotonic, pH neutral Fertility Gel 1b (Fertility Composition Formula AB) containing xylose and *Salvia sclarea* extract resulted in significantly lower lipid peroxidation of sperm plasma membranes following the experiment described in Gil-Villa et al. (Fertil. Steril. 94:1465, 2010) after 1 hour of incubation as compared to a paraben-containing commercial fertility product containing methylparaben and glycerol (Table 6). Additionally, the Fertility Gel 1b (Fertility Composition Formula AB) formulation resulted in no mucosal irritation potential, whereas the paraben and glycerin-containing commercial fertility product caused some increase in irritation potential, and surprisingly KY Jelly caused severe irritation (FIG. 5).

TABLE 6

Lipid Peroxidation of sperm after 1 hr. incubation

| Fertility Gel 1b | 5.5 ng/ml +/− 1.0 |
|---|---|
| Commercial Fertility Gel | 7.5 ng/ml +/− 2.1 |

Means differ at P = 0.05

An additive antioxidant effect of *Salvia* embodiments is observed on sperm lipid peroxidation in culture after 3 hours. Fertility Gel 1a is an embodiment with xylose. Fertility Gel 1b (Fertility Composition Formula AB) is an embodiment with xylose and *salvia*. Lipid peroxidation levels were significantly lower when both xylose and *salvia* were present (Table 7, p≤0.005).

TABLE 7

Lipid Peroxidation of sperm after 3 hours incubation

| Fertility Gel 1a | 42 ng/ml +/− 6 |
|---|---|
| Fertility Gel 1b | 39 ng/ml +/− 8 |

Fertility Gel 1b (Fertility Composition Formula AB) was also assessed for its effect on sperm motility and DNA damage (Table 8). Normal sperm quality samples and low quality sperm samples (low sperm count) were incubated for 30 minutes with a 10% solution of the Fertility Gel 1b or control medium (human Fallopian tube fluid).

TABLE 8

Sperm Motility and DNA Damage after 30 min incubation with Gel 1b

| Sample | Sperm Quality | Total Motile count | % DNA Damage |
|---|---|---|---|
| Control Medium | Normal | 43 +/− 17 | 9 +/− 5 |
| Fertility Gel 1b | Normal | 43 +/− 16 | 9 +/− 4 |
| Control Medium | Low Quality | 5 +/− 1.5 | 11 +/− 4 |
| Fertility Gel 1b | Low Quality | 5 +/− 1 | 10 +/− 3 |

The effect of Fertility Gel 1b on the ability of cryopreserved bull sperm to penetrate estrus cow cervical mucus following 30 minute exposure to a 10% solution was evaluated using a cervical mucus penetration assay (Table 9).

TABLE 9

Bovine Cervical Mucus Penetration Assay

| Sample | Vanguard Sperm Distance | # Sperm at 3 cm |
|---|---|---|
| Control Medium (TALP) | 5.5 cm +/− 1 | 12 +/− 3 |
| 10% Fertility Gel 1b | 5.8 cm +/− 2 | 16 +/− 2 |

Means differ between control and treated for both Vanguard sperm and sperm numbers at 3 cm (paired t-test, p < 0.05)

Taken together, Fertility Gel 1b provides: sperm antioxidant support with less oxidative damage to post-ejaculatory sperm, decreased mucosal irritation potential, superior cervical mucus penetration, and is non-detrimental to sperm motility or DNA quality.

Fertility Gel 1b (Fertility Composition Formula AB) was also evaluated for its effect on embryonic quality using a 1-cell mouse embryonic assay (MEA). The MEA is used as a regulatory special control for class II assisted reproduction and fertility devices and is a surrogate indicator of potential toxicity of materials used in fertility interventions that contact gametes and/or embryos (Gardner et al. 2005, Seminars in Reprod. Med. 23:319-324; Van den Bergh et al., 1996, J. Assisted Reprod. Genet. 13:733-738). In brief, one-cell mouse embryos were obtained and exposed to a 10% solution of the test composition diluted in M2 mouse embryo culture media for 30 minutes. The embryos were then transferred to appropriate culture medium and cultured for 96 hours. The number 1-cell embryos that transitioned to 2-cell embryos within 24 hours and the number of 1-cell embryos that transitioned to expanded blastocyst stage within 96 hours (blastocyst rate) were also determined. As shown in Table 10, Fertility Gel 1b test composition is non-toxic to embryos with a blastocyst rate that is greater than 80% of the control group.

TABLE 10

Mouse Embryo Assay for Fertility Gel 1b

| Sample | # 2-Cell Embryos at 24 hrs | Blastocyst Rate at 96 hrs |
|---|---|---|
| Gel 1b | 15/15 | 15/15 |
| Control | 20/21 | 21/21 |

An isotonic, pH neutral Fertility Gel 1c (also referred to herein as Fertility Gel Formula AB') was assessed for its effect on human sperm motility. The effect of a 10% solution of Fertility Gel 1c on sperm motility parameters was determined on semen collected from healthy, human male donors with both normal sperm counts (normospermia, n=10) and low total motile sperm counts (oligoasthenozoospermic, n=10) from a local sperm bank. Normospermia was defined as total motile sperm counts of >20 million/ml and oligoasthenozoospermia (OAT) was defined as total motile sperm concentrations of <15 million/ml. Each specimen was produced by masturbation without lubricant into a sterile plastic container after a recommended abstinence period of 48-96 hours. Specimens were allowed to liquefy and then processed within 30 minutes. Each sperm sample was diluted 1:4 with HTF media+10% human serum albumin, divided into two 900 µl aliquots, and placed into tissue culture wells. Gel 1c was added to one aliquot to achieve final concentrations of 10% V/V. The second aliquot served as the control. Specimens were incubated for 30 minutes at 37° C. and 5% $CO_2$ in 95% humidity.

Figure 6:
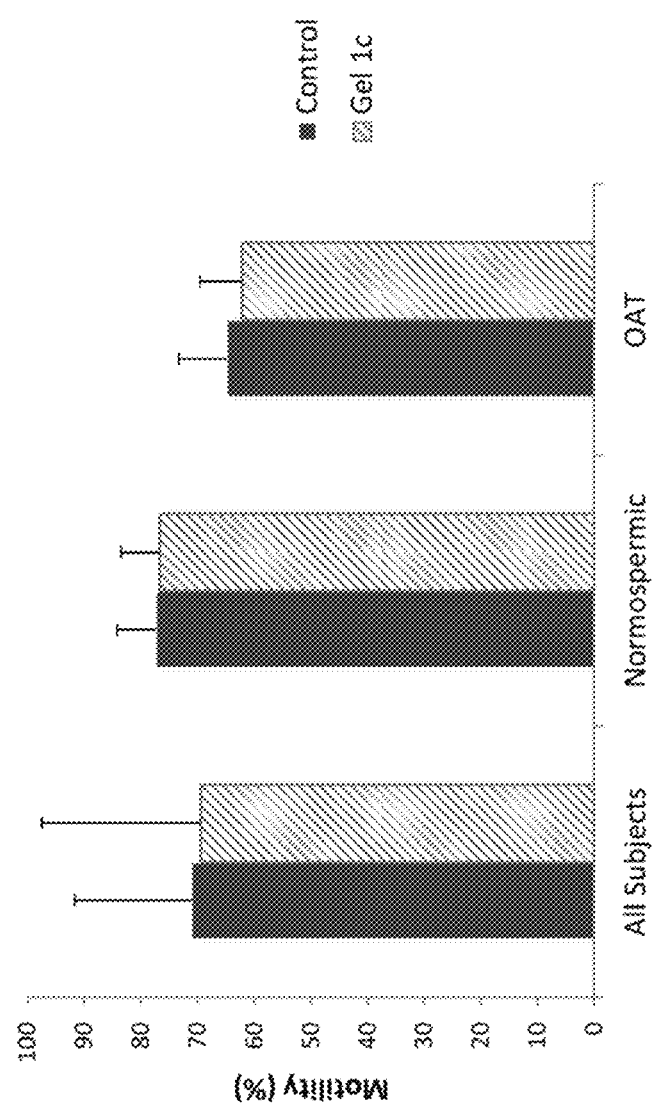
FIG. 6 is a bar graph depicting percent sperm motility of semen samples incubated for 30 minutes with 10% solution of Fertility Gel 1c as compared to a control.
Figure 7:
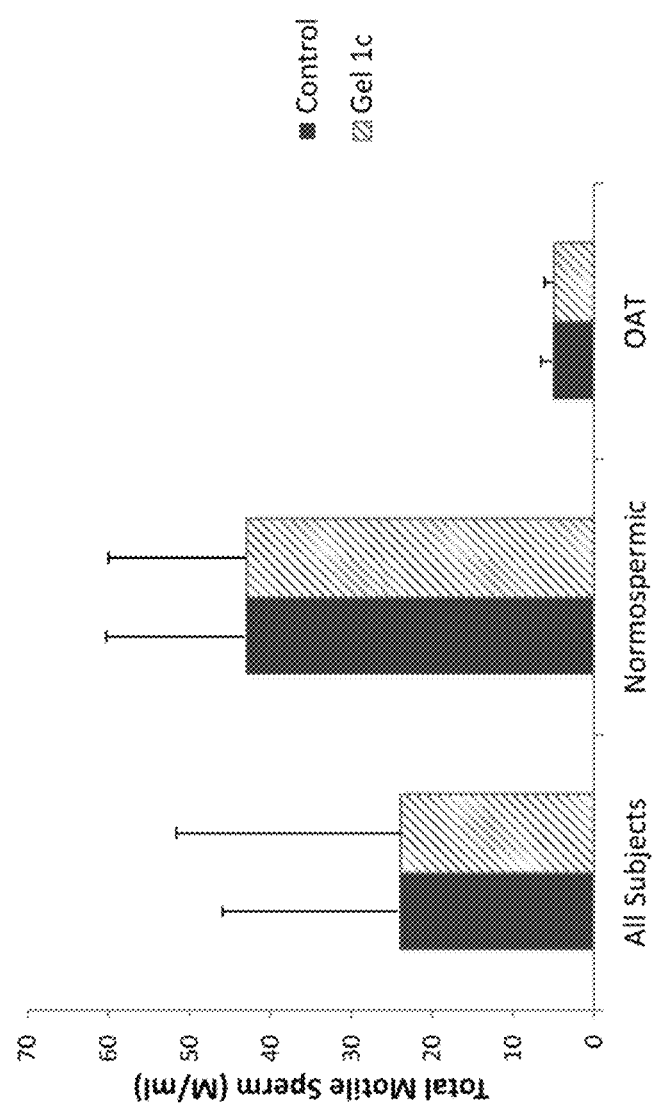
FIG. 7 is a bar graph depicting total motile sperm concentration of semen samples incubated for 30 minutes with 10% solution of Fertility Gel 1c as compared to a control.

The percentages of progressively motile sperm were determined manually in the following manner: 10 µl samples were placed on pre-warmed slides, and covered with a coverslip. Evaluations were performed according to WHO guidelines using an inverted phase contrast microscope. Progressively motile sperm were those regarded as a+b forms as indicated by WHO guidelines. Total motile concentration was calculated as the product of total sperm count and percent progressively motile sperm divided by 100. Normospermic and OAT semen samples exposed to 10% Gel 1c for 30 minutes did not differ from control with respect to percent motility (FIG. 6) or total motile concentration (FIG. 7). Thus, for normal and OAT samples, Gel 1c treatment did not harm sperm motility and total motile sperm concentrations.

The impact of Fertility Gel 1b (Fertility Formula AB) on sperm genetic material was assessed using a human sperm chromatin structure assay (SCSA). This assay is based on the metachromatic staining of single and double stranded DNA by acridine orange stain (Evenson et al., 1999, Human Reprod. 14:1039-1049; Evenson et al., 2002, J. Andrology 23:25-43). Excitation with an argon laser causes acridine orange intercalated in double-stranded DNA to emit a green fluorescence, whereas red fluorescence is emitted by single strand DNA. The extent of DNA denaturation in a sample is expressed as a and calculated by the formula $\alpha = red/(red+green)$. The endpoint measurement is DNA Fragmentation Index (DFI).

Semen samples were obtained from healthy male donors with normospermia (n=5) and mild oligoasthenozoospermia (n=5) at a local sperm bank. Normospermia was defined as total motile count >20 million/ml and oligoasthenozoospermia (OAT) was defined as total motile sperm concentration <15 million/ml. Each specimen was produced by masturbation without Gel 1b lubricant into a sterile plastic container after a recommended abstinence period of 48-96 hours. Specimens were allowed to liquefy and then processed within 30 minutes. Specimens were allowed to liquefy and then processed within 30 minutes. Specimens were allowed to liquefy and then processed within 30 minutes. Each sperm sample was diluted 1:4 with HTF media+10% human serum albumin, divided into two 900 µl aliquots, and placed into tissue culture wells. Gel 1b was added to one aliquot to achieve final concentrations of 10% V/V. The second aliquot served as the control. Specimens were incubated for 30 minutes at 37° C. and 5% $CO_2$ in 95% humidity. After 30 minutes of incubation, portions of each treatment were removed and placed in vials for flash freezing in liquid nitrogen. These were then tested using the Sperm Chromatin Structure Assay as described.

Figure 8:
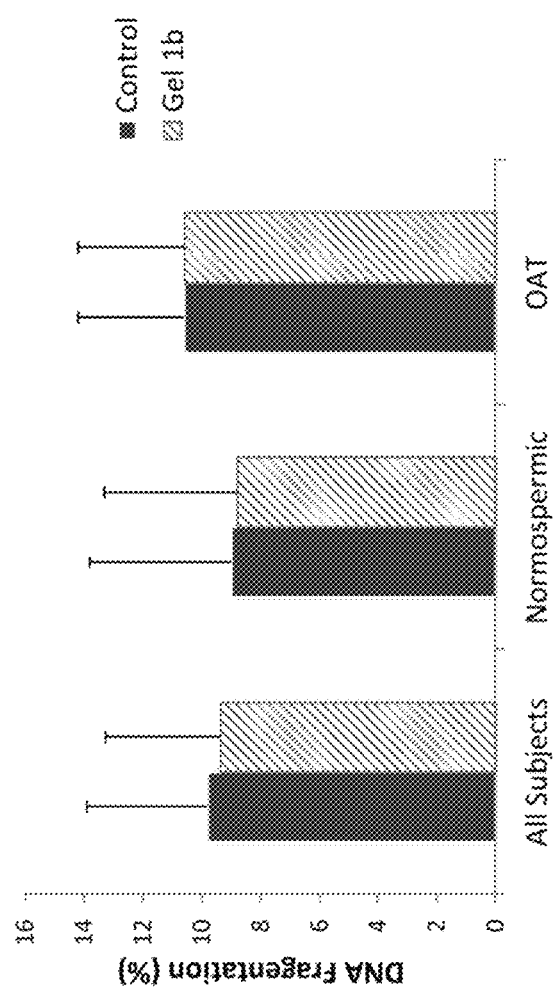
FIG. 8 is a bar graph depicting % DNA fragmentation of sperm chromatin from semen samples incubated with Fertility Gel 1b as measured by the sperm chromatin structure assay (SCSA).

The mean DFI (+/-sd) for normospermic, and OAT samples, was under 15% and did not differ between treated and control sperm (FIG. 8). A DFI of <15% DFI indicates excellent to good sperm DNA integrity. In normal and OAT human sperm samples, Fertility Gel 1b had no detrimental effect on DNA fragmentation or human sperm chromatin quality.

Fertility Gel 1c (Fertility Formula AB') was assessed via the Bovine Cervical Mucus Penetration Test to determine whether it had any detrimental effect on sperm penetration into cervical mucus. Cervical mucus was collected and pooled from 10 cows. Cervical mucus was frozen in aliquots of 3 mls and stored at -20° C. until use. Frozen mucus was thawed at room temperature for 30 minutes before use. Commercial cryopreserved sperm from 2 bulls was pooled and used in all replicates. Semen straws (0.5 mL) were thawed and sperm concentration adjusted to 10 million spermatozoa per ml using a commercial bovine semen-freezing medium. Flattened capillary tubes (0.3×3.0×100 mm) were filled with cervical mucus, sealed at one end and placed in 0.5 mL of the sperm suspension in each of two treatments: (1) Control (extender alone, lubricant free), and (2) Extender with 10% Gel 1c. Each treatment was repeated 10 times. Parameters evaluated after incubation at 37° C. for 30 minutes were: (1) distance travelled by vanguard sperm (cm); (2) density of spermatozoa at 2 cm and 3 cm; and (3) percent progressively motile sperm at 30 minutes. Table 11 summarizes the results of the bovine cervical mucus penetration test. Sperm treated with Fertility Gel 1c showed significantly higher rates of penetration into 3 cm of the mucus columns than did the control sperm (p=0.0261).

TABLE 11

Mean ± SEM for cervical mucus penetration variables according to treatment

| Treatment | N | Progressive Motility (%) | Vanguard sperm (cm) | Density at 2 cm | Density at 3 cm |
| --- | --- | --- | --- | --- | --- |
| Control | 10 | 40.5 ± 2.38 | 5.64 ± 0.20 | 27.9 ± 1.10 | 14.4 ± 0.87 |
| Gel 1c | 10 | 42.0 ± 1.53 | 5.81 ± 0.17 | 29.7 ± 0.56 | 16.6 ± 0.64* |

*p < 0.05 compared to control

The Fertility Gel 1c did not interfere with sperm motility in this system. Fertility Gel 1c also did not inhibit cervical mucus penetration as determined by both the vanguard sperm distance, and sperm density at set distances in cervical mucus columns incubated with bull sperm. Indeed, Fertility Gel 1c significantly improved sperm penetration into the furthest column distance (p<0.05).

Example 6

Slipperiness of Fertility Gel

A focus group was used to obtain quantitative measures of the degree of "lubricity" or "slipperiness" perceived for the Fertility Gel 1c (Fertility Formula AB') versus a commercially available, paraben-containing fertility product.

The two gel products were applied onto two different 4-cm circular sites on the non-dominant forearms of participants (n=20). The order of the gel, and the circular site to which it was applied, were determined randomly based on a computer generated randomization table. Each treatment was replicated twice.

Fingers and circular sites were wiped with a baby-wipe and paper towel. The focus group leader dispensed 0.1 ml of each sample into the center of the circular site previously drawn on the forearm. The sample was rubbed in a circle using the index finger at a rate of 2 rps for 15 seconds and followed with another 45 seconds. A metronome was set at 120 bpm and played to standardize the manipulation rate.

At time points 15 seconds and 60 seconds, slipperiness was evaluated using a 10 cm visual analog scale (VAS) (FIG. 9A). The two ends of the visual analog scale were anchored by the phrases "not slippery" and "very slippery." The focus group participant was asked to make a single line perpendicular to the VAS at the point of their slipperiness assessment between the two anchors. The degree of slipperiness was determined by measuring the distance (cm) of the participants mark on the visual analog scale from the left ("Not slippery") baseline.

FIG. 9B demonstrates that the Fertility Gel 1c was at least as slippery or lubricious as the commercial fertility gel at both 15 seconds (7.4 cm vs 7.2 cm, respectively) and 60 seconds (5.7 cm vs 5.4 cm, respectively). Thus, Fertility Gel 1c was as lubricious as a commercial paraben-containing fertility product.

Example 7

Menopause Lubricant Gels

Compositions directed at alleviating post-menopausal vaginal dryness and discomfort are described.

Menopausal Formula AB Gel was evaluated for irritation potential compared with other commercially available lubricants using the slug mucosal irritation (SMI) assay as described in Example 2. As shown in Table 12, Menopausal Formula AB Gel showed no irritation potential or tissue damage.

TABLE 12

SMI Assay for Menopausal Formula AB Gel

| Sample | Irritation Potential | Tissue Damage |
|---|---|---|
| Menopausal Formula AB Gel | None | No |
| KY Jelly | Severe | No |
| Replens | Moderate | No |
| Astroglide | Severe | Yes |

Menopausal Formula AB Gel is assayed for detrimental effects on suspensions vaginal microbiota species as described in Example 3.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Application No. 62/323,516 filed Apr. 15, 2016 and U.S. application Ser. No. 15/207,307 filed Jul. 11, 2016, are incorporated herein by reference, in their entirety. Aspects of embodiments can be modified, if necessary, to employ concepts of various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A topical composition, comprising: xylose at a total concentration ranging from about 0.01% to about 1% by weight; a *Salvia* extract at a total concentration ranging from about 0.01% to about 1% by weight; a surfactant at a total concentration ranging from about 0.25% to about 10% by weight; a buffering agent at a total concentration ranging from about 0.05% to about 2.5% by weight; a pH modifying agent at a total concentration ranging from about 0.001% to about 2% by weight; an osmolality adjuster at a total concentration ranging from about 0.1% to about 1% by weight; and water at a total concentration ranging from about 60% to about 99% by weight; wherein the composition has a pH ranging from about 3.0 to about 8.0, and wherein the composition is in the form of a semi-solid, gel, ointment, lotion, jelly, film, suspension emulsion, mucilage, foam, cream, paste or aerosol.

2. The composition of claim 1, further comprising a non-irritating viscosity increasing agent at a total concentration ranging from about 0.1% to about 25% by weight.

3. The composition of claim 2, wherein the non-irritating viscosity-increasing agent is a cellulose ether, a carbomer, a polyoxazoline, or any combination thereof.

4. The composition of claim 3, wherein the non-irritating viscosity-increasing agent is: (a) a carbomer, wherein the carbomer is carbomer homopolymer type B at a total concentration ranging from about 0.1% to about 3% by weight; or (b) a polyoxazoline, wherein the polyoxazoline is poly (2-methyl-2-oxazoline) at a total concentration ranging from about 5% to about 10% by weight.

5. The composition of claim 1, wherein the surfactant is a cetyl hydroxyethylcellulose, polyvinyl alcohol, or both.

6. The composition of claim 5, wherein the surfactant is: (a) a cetyl hydroxyethylcellulose at a total concentration ranging from about 0.25% to about 5% by weight; or (b) a polyvinyl alcohol at a total concentration ranging from about 1% to about 3% by weight.

7. The composition of claim 1, further comprising a paraben-free preservative at a total concentration ranging from about 0.005% to 5% by weight.

8. The composition of claim 7, wherein the paraben-free preservative is a phenethyl alcohol, caprylyl glycol, oleuropein, acemannan, carvacrol, an ascorbate, cranberry extract, or any combination thereof.

9. The composition of claim 1, further comprising a paraben-free preservative, wherein the paraben-free preservative is: (a) a phenethyl alcohol and caprylyl glycol together at a total concentration ranging from about 0.02% to about 1.5% by weight; (b) a phenethyl alcohol, caprylyl glycol and a sodium ascorbate, together at a total concentration ranging from about 0.5% to about 2% by weight; or (c) a cranberry extract at a total concentration ranging from about 0.01% to about 2.5% by weight.

10. The composition of claim 1, wherein the buffering agent is lactic acid, sodium lactate, ascorbic acid, sodium ascorbate, sodium phosphate, acetic acid, sodium acetate, citric acid, or any combination thereof.

11. The composition of claim 10, wherein the buffering agent is (a) lactic acid and sodium lactate together at a total concentration ranging from about 0.4% to about 1% by weight or (b) ascorbic acid and sodium ascorbate at a total concentration ranging from about 0.5% to about 2% by weight.

12. The composition of claim 1, wherein the osmolality adjuster is sodium chloride, potassium chloride, or both.

13. The composition of claim 1, wherein the pH modifying agent is ammonia, ammonium carbonate, diethanolamine, monoethanolamine, potassium hydroxide, potassium phosphate dibasic, sodium bicarbonate, sodium borate, sodium carbonate, sodium hydroxide, sodium lactate, sodium phosphate dibasic, trolamine, or any combination thereof.

14. The composition of claim 13, wherein the pH modifying agent is sodium hydroxide at a total concentration ranging from about 0.001% to about 1% by weight.

15. The composition of claim 1, wherein the *Salvia* extract is obtained from *Salvia sclarea, Salvia hispanica, Salvia plebeia*, or combinations thereof.

16. The composition of claim 15, wherein: the *Salvia* extract comprises a *Salvia sclarea* extract, wherein the *Salvia sclarea* extract is at a concentration ranging from about 0.025% to about 0.075% by weight; the non-irritating viscosity-increasing agent comprises poly(2-methyl-2-oxazoline) at a concentration ranging from about 1% to about 10% by weight; the surfactant comprises polyvinyl alcohol and cetyl hydroxyethylcellulose together at a total concentration ranging from about 1% to about 9% by weight; the buffering agent comprises lactic acid and sodium lactate together at a total concentration ranging from about 0.5% to about 1% by weight; the osmolality adjuster comprises sodium chloride at a concentration ranging from about 0.1% to about 0.7% by weight; the pH modifying agent comprises sodium hydroxide at a concentration ranging from about 0.001% to about 1% by weight; and the water is at a concentration ranging from about 75% to about 98% by weight.

17. The composition of claim 15, wherein: the *Salvia* extract comprises a *Salvia sclarea* extract, wherein the *Salvia sclarea* extract is at a concentration ranging from about 0.025% to about 0.075% by weight; the non-irritating viscosity-increasing agent comprises poly(2-methyl-2-oxazoline) at a concentration ranging from about 5% to about 10% by weight; the buffering agent comprises lactic acid and sodium lactate together at a total concentration ranging from about 0.5% to about 1% by weight; the osmolality adjuster comprises sodium chloride at a total concentration ranging from about 0.1% to about 0.7% by weight; the water is at a concentration ranging from about 85% to about 98% by weight; the pH modifying agent comprises sodium hydroxide at a concentration ranging from about 0.001% to about 1% by weight; and the composition further comprises a paraben-free preservative comprising, phenethyl alcohol and caprylyl glycol together at a total concentration ranging from about 0.2% to about 0.7% by weight.

18. The composition of claim 15, wherein: the *Salvia* extract comprises a *Salvia sclarea* extract, wherein the *Salvia sclarea* extract is at a concentration ranging from about 0.025% to about 0.075% by weight; the non-irritating viscosity-increasing agent comprises carbomer homopolymer type B at a total concentration ranging from about 0.1% to about 3% by weight; the surfactant comprises cetyl hydroxyethylcellulose at a total concentration ranging from about 0.5% to about 1.5% by weight; the buffering agent comprises lactic acid and sodium lactate together at a total concentration ranging from about 0.4% to about 1% by weight; the osmolality adjuster comprises sodium chloride at a total concentration ranging from about 0.1% to about 0.7% by weight; the water is at a concentration ranging from about 90% to about 98% by weight; the pH modifying agent comprises sodium hydroxide at a concentration ranging from about 0.001% to about 1% by weight; and the composition further comprises a paraben-free preservative comprising phenethyl alcohol and caprylyl glycol together at a total concentration ranging from about 0.2% to about 0.7% by weight.

19. The composition of claim 15, wherein: the *Salvia* extract comprises a *Salvia sclarea* extract, wherein the *Salvia sclarea* extract is at a concentration ranging from about 0.025% to about 0.075% by weight; the non-irritating viscosity-increasing agent comprises carbomer homopolymer type B at a total concentration ranging from about 0.1% to about 3% by weight; the surfactant comprises cetyl hydroxyethylcellulose at a total concentration ranging from about 0.5% to about 1.5% by weight; the buffering agent comprises ascorbic acid and sodium ascorbate together at a total concentration ranging from about 0.5% to about 1.2% by weight; the osmolality adjuster comprises sodium chloride at a total concentration ranging from about 0.1% to about 0.7% by weight; the water is at a concentration ranging from about 90% to about 98% by weight; and the composition further comprises a paraben-free preservative comprising phenethyl alcohol and caprylyl glycol together at a total concentration ranging from about 0.2% to about 0.7% by weight.

20. The composition of claim 15, wherein: the *Salvia* extract comprises *Salvia sclarea* extract, wherein the *Salvia sclarea* extract is at a concentration ranging from about 0.025% to about 0.075% by weight; the non-irritating viscosity-increasing agent comprises carbomer homopolymer type B at a total concentration ranging from about 1% to about 3% by weight; the surfactant comprises polyvinyl alcohol at a total concentration ranging from about 1% to about 3% by weight; the buffering agent comprises lactic acid and sodium lactate together at a total concentration ranging from about 0.5% to about 1% by weight; the osmolality adjuster comprises sodium chloride at a total concentration ranging from about 0.1% to about 0.7% by weight; the water is at a concentration ranging from about 90% to about 98% by weight; and the pH modifying agent comprises sodium hydroxide at a concentration ranging from about 0.001% to about 1% by weight.

21. The composition of claim 18, wherein the paraben-free preservative comprises a solution of phenethyl alcohol and caprylyl glycol together at a total concentration ranging from about 0.2% to about 0.7% by weight, wherein the solution comprises phenethyl alcohol in an amount of 56%-60% and caprylyl glycol in an amount of 40%-44%.

22. The composition of claim 19, wherein the paraben-free preservative comprises a solution of phenethyl alcohol and caprylyl glycol together at a total concentration ranging from about 0.2% to about 0.7% by weight, wherein the solution comprises phenethyl alcohol in an amount of 56%-60% and caprylyl glycol in an amount of 40%-44%.

23. The composition of claim 18, wherein the composition has a pH of about 3.5 to about 5.5.

24. The composition of claim 19, wherein the composition has a pH of about 3.5 to about 5.5.

25. A method for enhancing ecosystem homeostasis of the lower reproductive tract, comprising topically applying an effective amount of the composition of claim 1 to the lower reproductive tract of a human female subject.

26. The method of claim 25, wherein the microbiota of the human female subject is not reduced greater than 25% following topical application of the composition to the lower reproductive tract as compared to an untreated control human female subject or prior to topical application of the composition to the lower reproductive tract.

27. The method of claim 25, wherein the composition is applied to an external genital organ or the human female subject.

28. A method for increasing hydration of the lower reproductive tract, comprising topically applying an effective amount of the composition of claim 1 to the lower reproductive tract of a human female subject.

29. The method of claim 28, wherein the microbiota of the human female subject is not reduced greater than 25% following topical application of the composition to the lower reproductive tract as compared to an untreated control human female subject or prior to topical application of the composition to the lower reproductive tract.

30. A method of cleansing the lower reproductive tract or controlling unwanted odor of the lower reproductive tract comprising topically applying an effective amount of the composition of claim 1 to the lower reproductive tract of a human female subject.

31. The method of claim 30, wherein the vaginal microbiota of the human female subject is not reduced greater than 25% following topical application of the composition to the lower reproductive tract as compared to an untreated control human female subject or prior to topical application of the composition to the lower reproductive tract.

32. The method of claim 30, wherein the composition is applied to an external genital organ or the human female subject.

33. A method for increasing the hydration of an external genital organ, comprising topically applying an effective amount of the composition of claim 1 to the external genital organ of a human female subject.

34. The method of claim 33, wherein the microbiota of the human female subject is not reduced greater than 25% following topical application of the composition to the external genital organ as compared to an untreated control human female subject or prior to application of the composition to the external genital organ.

* * * * *

UNITED STATES PATENT AND TRADEMARK OFFICE
CERTIFICATE OF CORRECTION

PATENT NO. : 11,419,909 B2
APPLICATION NO. : 16/436504
DATED : August 23, 2022
INVENTOR(S) : Joanna E. Ellington and G. Dennis Clifton It is certified that error appears in the above-identified patent and that said Letters Patent is hereby corrected as shown below:

In the Claims

Column 67, Claim 15, Line 1, "The composition of claim 1," should read --The composition of claim 2,--.

Signed and Sealed this
Twenty-eighth Day of March, 2023

Katherine Kelly Vidal
*Director of the United States Patent and Trademark Office*